US008158599B2

(12) United States Patent
Harden et al.

(10) Patent No.: US 8,158,599 B2
(45) **Date of Patent: *Apr. 17, 2012**

(54) CHIMERIC ADENOVIRUSES FOR USE IN CANCER TREATMENT

(75) Inventors: Paul Harden, Brentwood, CA (US); Terry Hermiston, Corte Madera, CA (US); Irene Kuhn, Richmond, CA (US)

(73) Assignee: PsiOxus Therapeutics Limited, London (GB)

(*) Notice: Subject to any disclaimer, the term of this patent is extended or adjusted under 35 U.S.C. 154(b) by 135 days.

This patent is subject to a terminal disclaimer.

(21) Appl. No.: 12/413,748

(22) Filed: Mar. 30, 2009

(65) Prior Publication Data

US 2009/0227000 A1 Sep. 10, 2009

Related U.S. Application Data

(62) Division of application No. 11/136,912, filed on May 24, 2005, now Pat. No. 7,510,868.

(60) Provisional application No. 60/574,851, filed on May 26, 2004.

(51) Int. Cl.
*A61K 48/00* (2006.01)
*C12N 15/00* (2006.01)

(52) U.S. Cl. ....................................... 514/44; 435/320.1

(58) Field of Classification Search ........................ None
See application file for complete search history.

(56) References Cited

U.S. PATENT DOCUMENTS

| | | | |
|---|---|---|---|
| 5,677,178 | A | 10/1997 | McCormick et al. |
| 5,972,706 | A | 10/1999 | McCormick et al. |
| 7,510,868 | B2 | 3/2009 | Harden et al. |
| 2002/0019051 | A1 | 2/2002 | Lusky et al. |
| 2003/0017138 | A1 | 1/2003 | Havenga et al. |
| 2004/0136958 | A1 | 7/2004 | Wadell et al. |
| 2004/0151696 | A1 | 8/2004 | Johnson et al. |

FOREIGN PATENT DOCUMENTS

| | | |
|---|---|---|
| SE | 0100035-5 | 1/2001 |
| WO | WO 02/053759 | 7/2002 |
| WO | WO 02/053759 A1 | 7/2002 |

OTHER PUBLICATIONS

Jolly, D. et al. "Viral vector systems for gene therapy."*Cancer Gene Therapy*. vol. 1. No. 1, 51-64. (1994).

Heise et al. "Onyx-015, an E1B gene-attenuated adenovirus, causes tumor-specific cytolysis and antitumoral efficacy that can be augmented by standard chemotherapeutic agents." *Nat. Med*. vol. 3. No. 6. 639-645. (1997).

Mei et al. " Comparative analysis of the genome organization of human adenovirus 11, a member of the human adenovirus species B, and the commonly used human adenovirus 5 vector, a member of species C." *J. Gen. Virology*. vol. 84, 2061-2071. (2003).

Grill et al. "The organotypic multicellular spheroid is a relevant three-dimensional model to study adenovirus replication and penetration in human tumors in vitro." *Mol. Therapy*. vol. 6. No. 5, 609-614. (2002).

Lai et al. "Adenovirus and adeno-associated virus vectors." *DNA Cell Bio*. vol. 21. No. 12, 895-913. (2002).

Stone et al. "The complete nucleotide sequence, genome organization, and origin of human adenovirus type 11." *Virology*. vol. 309, 152-165. (2003).

Yan et al. "Developing novel oncolytic adenoviruses through bioselection."*J. Virol*. vol. 77 No. 4, 2640-2650. (2003).

Stevenson et al. "Selective targeting of human cells by a chimeric adenovirus vector containing a modified fiber protein." *J. Virol*. vo1. 71. No. 6, 4782-4790. (1997).

Hermiston et al., "Armed Therapeutic Viruses: Strategies and Challenges to Arming Oncolytic Viruses With Therapeutic Genes." *Cancer Gene Therapy*, (2002) vol. 9, pp. 1022-1035.

Hermiston et al., "The Discovery and Development of Selectively Replicating Adenoviruses as Anticancer Agents." *Tumor Targeting*, (2000) vol. 4, pp. 218-224.

Puthupparampil et al., "Tumor Growth Inhibition from Tumor Targeted Delivery of Diphtheria Toxin Gene." *Molecular Therapy*, (2005) vol. 11, Supplement No. 1, p. A124.

Casimiro et al., "Comparative Immunogenicity in Rhesus Monkeys of DNA Plasmid, Recombinant Vaccinia Virus, and Replication-Defective Adenovirus Vectors Expressing a Human Immunodeficiency Virus Type 1 *gag* Gene," *J. Virol. 77*, 6305-13, 2003.

*Primary Examiner* — Bao Li

(74) *Attorney, Agent, or Firm* — Banner & Witcoff, Ltd.

(57) ABSTRACT

The present invention relates to oncolytic adenoviruses having therapeutic applications. Recombinant chimeric adenoviruses, and methods to produce them are provided. The chimeric adenoviruses of the invention comprise nucleic acid sequences derived from adenoviral serotypes classified within the subgroups B through F and demonstrate an enhanced therapeutic index.

8 Claims, 9 Drawing Sheets

Starting Pool of Virus
Panc-1 bioselected pool
HT-29 bioselected pool
PC-3 bioselected pool
MDA231 bioselected pool
10
15
20
Retention Time (minutes)
Ad5 (260od)

A.
HT-29 Cells
Day 4 P.I.
% Control
MOI (Vp/cell)
B.
MDA231 Cells
Day 6 P.I.
% Control
MOI (Vp/cell)
C.
Panc-1 Cells
Day 5 P.I.
% Control
MOI (Vp/cell)
D.
PC-3 Cells
Day 7 P.I.
% Control
MOI (Vp/cell)

HT-29 Cells
Day 5 P.I.
DU145 Cells
Day 5 P.I.
MDA231 Cells
Day 8 P.I.
OVCAR-3 Cells
Day 7 P.I.
Panc-1 Cells
Day 6 P.I.
PC-3 Cells
Day 5 P.I.
% Control
MOI (Vp/cell)

HUVEC Cells
Day 6 P.I.
HS-27 Cells
Day 15 P.I.
SAEC Cells
Day 6 P.I.
% Control
MOI (Vp/cell)

A.
HT-29 Cells
Day 5 P.I.
B.
HUVEC Cells
Day 6 P.I.
% Control
MOI (Vp/cell)
0.01
0.10
1.00
10.00
100.00
0
20
40
60
80
100
120

CHIMERIC ADENOVIRUSES FOR USE IN CANCER TREATMENT

This application is a division of Ser. No. 11/136,912 filed May 24, 2005, which claims the benefit of Ser. No. 60/574,851, filed on May 26, 2004. Each of these applications is incorporated herein by reference in its entirety.

FIELD OF THE INVENTION

The invention described herein relates generally to the field of molecular biology, and more specifically to oncolytic adenoviruses having therapeutic applications.

BACKGROUND OF THE INVENTION

Cancer is a leading cause of death in the United States and elsewhere. Depending on the type of cancer, it is typically treated with surgery, chemotherapy, and/or radiation. These treatments often fail, and it is clear that new therapies are necessary, to be used alone or in combination with classical techniques.

One approach has been the use of adenoviruses, either alone or as vectors able to deliver anti-cancer therapeutic proteins to tumor cells. Adenoviruses are non-enveloped icosohedral double-stranded DNA viruses with a linear genome of approximately 36 kilobase pairs. Each end of the viral genome has a short sequence known as the inverted terminal repeat (or ITR), which is required for viral replication. All human adenovirus genomes examined to date have the same general organization; that is, the genes encoding specific functions are located at the same position on the viral genome. The viral genome contains five early transcription units (E1A, E1B, E2, E3, and E4), two delayed early units (IX and Iva2), and one late unit (major late) that is processed to generate five families of late mRNAs (L1-L5). Proteins encoded by the early genes are involved in replication, whereas the late genes encode viral structural proteins. Portions of the viral genome can be readily substituted with DNA of foreign origin and recombinant adenoviruses are structurally stable, properties that make these viruses potentially useful for gene therapy (see Jolly, D. (1994) *Cancer Gene Therapy* 1:51-64).

Currently, the research efforts to produce clinically useful adenoviral therapy have focused on the adenoviral serotype, Ad5. The genetics of this human adenovirus are well-characterized and systems are well described for its molecular manipulation. High capacity production methods have been developed to support clinical applications, and some clinical experience with the agent is available. See, Jolly, D. (1994) *Cancer Gene Therapy* 1:51-64. Research related to the use of human adenoviruses (Ad) in cancer treatment has focused on the development of Ad5-based adenoviruses that have a higher potency in, or are preferentially targeted to, specific tumor cell types and there exists a need for generation of more potent oncolytic viruses if adenoviral therapy is to find practical application in a clinical setting.

Ad5 is only one of 51 currently known adenoviral serotypes, which are classified into subgroups A-F, based on various attributes including their hemagglutination properties ((see, Shenk, "Adenoviridae: The Viruses and Their Replication," in Fields Virology, Vol. 2, Fourth Edition, Knipe, ea., Lippincott, Williams & Wilkins, pp. 2265-2267 (2001)). These serotypes differ at a variety of levels, e.g. pathology in humans and rodents, cell receptors used for attachment, but these differences have been largely ignored as potential means to develop more potent oncolytic adenoviruses (with the exception of fiber alterations, see Stevenson et al. (1997) *J. Virol.* 71:4782-4790; Krasnykh et al. (1996) *J. Virol.* 70:6839-6846; Wickham et al. (1997) *J. Virol.* 71:8221-8229; Legrand et al. (2002) *Curr. Gene Ther.* 2:323-329; Barnett et al. (2002) Biochim. Biophys. Acta 1-3:1-14; US Patent Application 2003/0017138).

Exploitation of differences among adenoviral serotypes may provide a source of more effective adenoviral-based therapeutics, using novel adenoviruses with increased selectivity and potency. There is a need for such improved adenoviral-based therapies.

SUMMARY OF THE INVENTION

The present invention provides novel chimeric adenoviruses, or variants or derivatives thereof, useful for viral-based therapy. In particular, the invention provides for chimeric adenoviruses, or variants or derivatives thereof, having a genome comprising an E2B region wherein said E2B region comprises a nucleic acid sequence derived from a first adenoviral serotype and a nucleic acid sequence derived from a second adenoviral serotype;

wherein said first and second adenoviral serotypes are each selected from the adenoviral subgroups B, C, D, E, or F and are distinct from each other; and wherein said chimeric adenovirus is oncolytic and demonstrates an enhanced therapeutic index for a tumor cell.

In one embodiment, the chimeric adenovirus further comprises regions encoding fiber, hexon, and penton proteins, wherein the nucleic acids encoding said proteins are all from the same adenoviral serotype. In another embodiment, the chimeric adenovirus of the invention comprises a modified E3 or E4 region.

In another embodiment, the chimeric adenovirus demonstrates an enhanced therapeutic index in a colon, breast, pancreas, lung, prostate, ovarian or hemopoietic tumor cell. In a particularly preferred embodiment, the chimeric adenovirus displays an enhanced therapeutic index in colon tumor cells.

In a preferred embodiment, the E2B region of the chimeric adenovirus comprises SEQ ID NO: 3. In a particularly preferred embodiment, the chimeric adenovirus comprises SEQ ID NO: 1.

The present invention provides for a recombinant chimeric adenovirus, or a variant or derivative thereof, having a genome comprising an E2B region wherein said E2B region comprises a nucleic acid sequences derived from a first adenoviral serotype and a nucleic acid second derived from a second adenoviral serotype;

wherein said first and second adenoviral serotypes are each selected from the adenoviral subgroups B, C, D, E, or F and are distinct from each other;

wherein said chimeric adenovirus is oncolytic and demonstrates an enhanced therapeutic index for a tumor cell; and wherein said chimeric adenovirus has been rendered replication deficient through deletion of one or more adenoviral regions encoding proteins involved in adenoviral replication selected from the group consisting of E1, E2, E3 or E4.

In one embodiment, the chimeric adenovirus of the invention further comprises a heterologous gene that encodes a therapeutic protein, wherein said heterologous gene is expressed within a cell infected with said adenovirus. In a preferred embodiment, the therapeutic protein is selected from the group consisting of cytokines and chemokines, antibodies, pro-drug converting enzymes, and immunoregulatory proteins.

The present invention provides methods for using the chimeric adenoviruses of the invention for therapeutic purposes. In one embodiment, the chimeric adenoviruses can be used to inhibit the growth of cancer cells. In a particular embodiment, a chimeric adenovirus comprising SEQ ID NO: 1 is useful for inhibiting the growth of colon cancer cells.

In another embodiment, the adenoviruses of the invention are useful as vectors to deliver therapeutic proteins to cells.

The present invention provides a method for production of the chimeric adenoviruses of the invention, wherein the method comprises a) pooling of adenoviral serotypes representing adenoviral subgroups B-F, thereby creating an adenoviral mixture;
b) passaging the pooled adenoviral mixture from step (a) on an actively growing culture of tumor cells at a particle per cell ratio high enough to encourage recombination between serotypes, but not so high as to produce premature cell death;
c) harvesting the supernatant from step (b);
d) infecting a quiescent culture of tumor cells with the supernatant harvested in step (c);
e) harvesting the cell culture supernatant from step (d) prior to any sign of CPE;
f) infecting a quiescent culture of tumor cells with the supernatant harvested in step (e); and
g) isolating the chimeric adenovirus from the supernatant harvested in step (f) by plaque purification.

DETAILED DESCRIPTION OF THE INVENTION

Figure 1A:
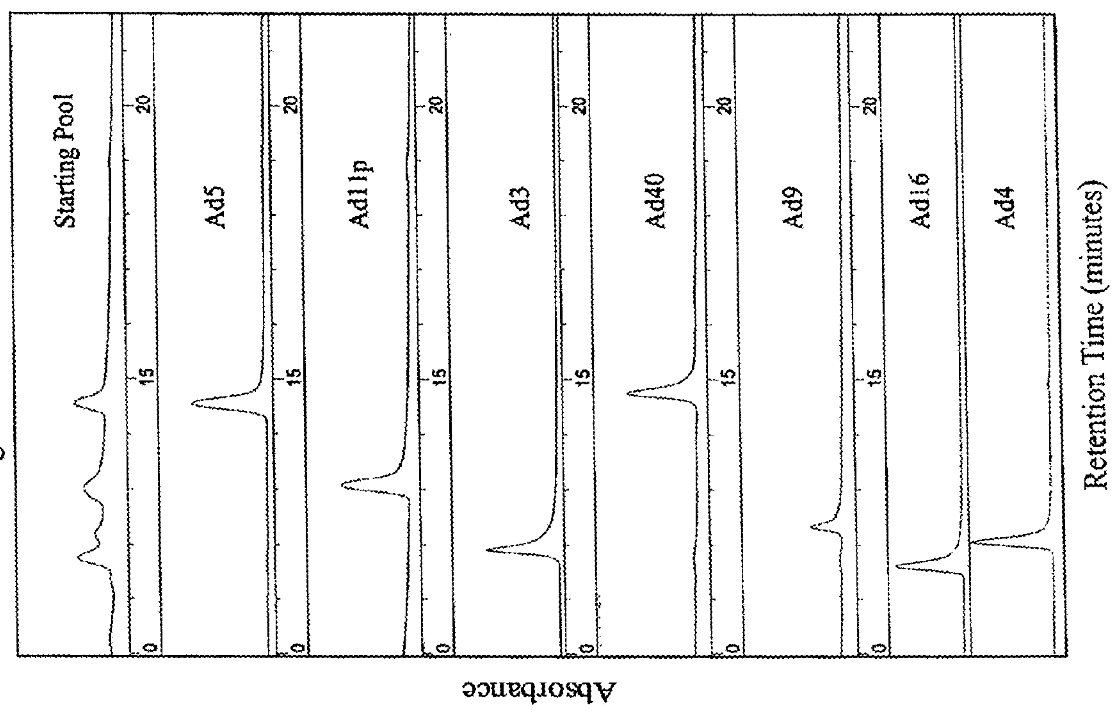
FIG. 1. Ad retention time profiles on a TMAE HPLC column. A) Retention profiles for the individual Ad serotypes that were used to generate the original starting viral pool. B) Retention profiles of the passage 20 pools derived from HT-29, Panc-1, MDA-231, and PC-3 cell lines, respectively.

All publications, including patents and patent applications, mentioned in this specification are herein incorporated by reference to the same extent as if each individual publication was specifically and individually indicated to be incorporated by reference in its entirety.

DEFINITIONS

Unless defined otherwise, all technical and scientific terms used herein have the same meaning as commonly understood by one of ordinary skill in the art to which this invention belongs. Generally, the nomenclature used herein and the laboratory procedures described below are those well known and commonly employed in the art.

As used herein, the term "adenovirus", "serotype" or "adenoviral serotype" refers to any of the 51 human adenoviral serotypes currently known, or isolated in the future. See, for example, Strauss, "Adenovirus infections in humans," in The Adenoviruses, Ginsberg, ea., Plenum Press, New York, N.Y., pp. 451-596 (1984). These serotypes are classified in the subgroups A-F (see, Shenk, "Adenoviridae: The Viruses and Their Replication," in Fields Virology, Vol. 2, Fourth Edition, Knipe, ea., Lippincott Williams & Wilkins, pp. 2265-2267 (2001), as shown in Table 1.

TABLE 1

| SubGroup | Adenoviral Serotype |
|---|---|
| A | 12, 18, 31 |
| B | 3, 7, 11, 14, 16, 21, 34, 35, 51 |
| C | 1, 2, 5, 6 |
| D | 8-10, 13, 15, 17, 19, 20, 22-30, 32, 33, 36-39, 42-49, 50 |
| E | 4 |
| F | 40, 41 |

As used herein, "chimeric adenovirus" refers to an adenovirus whose nucleic acid sequence is comprised of the nucleic acid sequences of at least two of the adenoviral serotypes described above.

As used herein, "parent adenoviral serotype" refers to the adenoviral serotype which represents the serotype from which the majority of the genome of the chimeric adenovirus is derived.

As used herein, the term "homologous recombination" refers to two nucleic acid molecules, each having homologous sequences, where the two nucleic acid molecules cross over or undergo recombination in the region of homology.

As used herein, the term "potency" refers to the lytic potential of a virus and represents its ability to replicate, lyse, and spread. For the purposes of the instant invention, potency is a value which compares the cytolytic activity of a given adenovirus of the invention to that of Ad5 in the same cell line, i.e. potency=$IC_{50}$ of AdX/$IC_{50}$ of Ad5, where X is the particular adenoviral serotype being examined and wherein the potency of Ad5 is given a value of 1.

As used herein, the term "oncolytic virus" refers to a virus that preferentially kills cancer cells as compared with normal cells.

As used herein, the term "therapeutic index" or "therapeutic window" refers to a number indicating the oncolytic potential of a given adenovirus and is determined by dividing the potency of the adenovirus in a cancer cell line by the potency of the same adenovirus in a normal (i.e. non-cancerous) cell line.

As used herein, the term "modified" refers to a molecule with a nucleotide or amino acid sequence differing from a naturally-occurring, e.g. a wild-type nucleotide or amino acid sequence. A modified molecule can retain the function or activity of a wild-type molecule, i.e. a modified adenovirus may retain its oncolytic activity. Modifications include mutations to nucleic acids as described below.

As used herein, "mutation" with reference to a polynucleotide or polypeptide, refers to a naturally-occurring, synthetic, recombinant, or chemical change or difference to the primary, secondary, or tertiary structure of a polynucleotide or polypeptide, as compared to a reference polynucleotide or polypeptide, respectively (e.g., as compared to a wild-type polynucleotide or polypeptide). Mutations include such changes as, for example, deletions, insertions, or substitutions. Polynucleotides and polypeptides having such mutations can be isolated or generated using methods well known in the art.

As used herein, "deletion" is defined as a change in either polynucleotide or amino acid sequences in which one or more polynucleotides or amino acid residues, respectively, are absent.

As used herein, "insertion" or "addition" is that change in a polynucleotide or amino acid sequence which has resulted in the addition of one or more polynucleotides or amino acid residues, respectively, as compared to the naturally occurring polynucleotide or amino acid sequence.

As used herein, "substitution" results from the replacement of one or more polynucleotides or amino acids by different polynucleotides or amino acids, respectively.

As used herein, the term "adenoviral derivative" refers to an adenovirus of the invention that has been modified such that an addition, deletion or substitution has been made to or in the viral genome, such that the resulting adenoviral derivative exhibits a potency and/or therapeutic index greater than that of the parent adenovirus, or in some other way is more therapeutically useful (i.e., less immunogenic, improved clearance profile). For example, a derivative of an adenovirus of the invention may have a deletion in one of the early genes of the viral genome, including, but not limited to, the E1A or E2B region of the viral genome.

As used herein, "variant" with reference to a polynucleotide or polypeptide, refers to a polynucleotide or polypeptide that may vary in primary, secondary, or tertiary structure, as compared to a reference polynucleotide or polypeptide, respectively (e.g., as compared to a wild-type polynucleotide or polypeptide). For example, the amino acid or nucleic acid sequence may contain a mutation or modification that differs from a reference amino acid or nucleic acid sequence. In some embodiments, an adenoviral variant may be a different isoform or polymorphism. Variants can be naturally-occurring, synthetic, recombinant, or chemically modified polynucleotides or polypeptides isolated or generated using methods well known in the art. Changes in the polynucleotide sequence of the variant may be silent. That is, they may not alter the amino acids encoded by the polynucleotide. Where alterations are limited to silent changes of this type, a variant will encode a polypeptide with the same amino acid sequence as the reference. Alternatively, such changes in the polynucleotide sequence of the variant may alter the amino acid sequence of a polypeptide encoded by the reference polynucleotide, resulting in conservative or non-conservative amino acid changes, as described below. Such polynucleotide changes may result in amino acid substitutions, additions, deletions, fusions and truncations in the polypeptide encoded by the reference sequence. Various codon substitutions, such as the silent changes that produce various restriction sites, may be introduced to optimize cloning into a plasmid or viral vector or expression in a particular prokaryotic or eukaryotic system.

As used herein, an "adenoviral variant" refers to an adenovirus whose polynucleotide sequence differs from a reference polynucleotide, e.g. a wild-type adenovirus, as described above. The differences are limited so that the polynucleotide sequences of the parent and the variant are similar overall and, in most regions, identical. As used herein, a first nucleotide or amino acid sequence is said to be "similar" to a second sequence when a comparison of the two sequences shows that they have few sequence differences (i.e., the first and second sequences are nearly identical). As used herein, the polynucleotide sequence differences present between the adenoviral variant and the reference adenovirus do not result in a difference in the potency and/or therapeutic index.

As used herein, the term "conservative" refers to substitution of an amino acid residue for a different amino acid residue that has similar chemical properties. Conservative amino acid substitutions include replacement of a leucine with an isoleucine or valine, an aspartate with a glutamate, or a threonine with a serine. Insertions or deletions are typically in the range of about 1 to 5 amino acids.

As used herein, the term "nonconservative" refers to substituting an amino acid residue for a different amino acid residue that has different chemical properties. The nonconservative substitutions include, but are not limited to aspartic acid (D) being replaced with glycine (G); asparagine (N) being replaced with lysine (K); or alanine (A) being replaced with arginine (R).

The single-letter codes for amino acid residues include the following: A=alanine, R=arginine, N=asparagine, D=aspartic acid, C=cysteine, Q=Glutamine, E=Glutamic acid, G=glycine, H=histidine, I=isoleucine, L=leucine, K=lysine, M=methionine, F=phenylalanine, P=proline, S=serine, T=threonine, W=tryptophan, Y=tyrosine, V=valine.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, *Proteins-Structure and Molecular Properties,* 2nd Ed., W.H. Freeman and Company, New York, 1993. Many detailed reviews are available on this subject, such as, for example, those provided by Wold, F., in *Post-translational Covalent Modification of Proteins*, B. C. Johnson, Ed., Academic Press, New York, pp 1-12, 1983; Seifter et al., *Meth. Enzymol.* 182: 626-646, 1990 and Rattan et al., *Protein Synthesis: Posttranslational Modifications and Aging*, Ann. N.Y. Acad. Sci. 663: 48-82, 1992.

It will be appreciated, as is well known and as noted above, that polypeptides are not always entirely linear. For instance, polypeptides may be branched as a result of ubiquitination, and they may be circular, with or without branching, generally as a result of posttranslational events, including natural processing events and events brought about by human manipulation which do not occur naturally. Circular, branched and branched circular polypeptides may be synthesized by non-translational natural processes and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

As used herein, the following terms are used to describe the sequence relationships between two or more polynucleotide or amino acid sequences: “reference sequence”, “comparison window/”, “sequence identity”, “percentage of sequence identity”, “substantial identity”, “similarity”, and “homologous”. A “reference sequence” is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a “comparison window” to identify and compare local regions of sequence similarity. A “comparison window”, as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted, for example, by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), VectorNTI from Informatix, Geneworks, or MacVector software packages), or by inspection, and the best alignment (i.e., resulting in the highest percentage of homology over the comparison window) generated by the various methods is selected.

As used herein, the term “sequence identity” means that two polynucleotide or amino acid sequences are identical (i.e., on a nucleotide-by-nucleotide or residue-by-residue basis) over the comparison window. The term “percentage of sequence identity” is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence. The term "similarity", when used to describe a polypeptide, is determined by comparing the amino acid sequence and the conserved amino acid substitutes of one polypeptide to the sequence of a second polypeptide. The term "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

As used herein, "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and more preferably at least about 98 to 99% of the nucleotides.

As used herein, "polymerase chain reaction" or "PCR" refers to a procedure wherein specific pieces of DNA are amplified as described in U.S. Pat. No. 4,683,195. Generally, sequence information from the ends of the polypeptide fragment of interest or beyond needs to be available, such that oligonucleotide primers can be designed; these primers will point towards one another, and will be identical or similar in sequence to opposite strands of the template to be amplified. The 5' terminal nucleotides of the two primers will coincide with the ends of the amplified material. PCR can be used to amplify specific DNA sequences from total genomic DNA, cDNA transcribed from total cellular RNA, plasmid sequences, etc. (See generally Mullis et al., *Cold Spring Harbor Symp. Quant. Biol.,* 51: 263, 1987; Erlich, ed., *PCR Technology*, Stockton Press, NY, 1989).

As used herein, "stringency" typically occurs in a range from about $T_m$ (melting temperature)-5° C. (5° below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. As herein used, the term "stringent conditions" means hybridization will occur only if there is at least 95% and preferably at least 97% identity between the sequences.

As used herein, "hybridization" as used herein, shall include "any process by which a polynucleotide strand joins with a complementary strand through base pairing" (Coombs, J., *Dictionary of Biotechnology*, Stockton Press, New York, N.Y., 1994).

As used herein, the term "therapeutically effective dose" or "effective amount" refers to that amount of adenovirus which ameliorates the symptoms or conditions of a disease. A dose is considered a therapeutically effective dose in the treatment of cancer or its metastasis when tumor or metastatic growth is slowed or stopped, or the tumor or metastasis is found to shrink in size, so as to lead to an extension in life-span for the subject.

Adenoviruses of the Invention

The present invention provides chimeric adenoviruses, or variants or derivatives thereof, having a genome in which the nucleotide sequence of the E2B region of the chimeric adenovirus comprises nucleic acid sequences derived from at least two adenoviral serotypes, which serotypes are each selected from the adenoviral subgroups B, C, D, E and F and are distinct from each other. A chimeric adenovirus of the invention is oncolytic and demonstrates an enhanced therapeutic index for a tumor cell.

Isolation of Chimeric Adenoviruses

The chimeric adenoviruses of the invention, or variants or derivatives thereof, can be produced using modification of a technique referred to as "bioselection", in which an adenovirus with desired properties, such as enhanced oncogenicity or cell type specificity, is generated through the use of genetic selection under controlled conditions (Yan et al. (2003) *J. Virol.* 77:2640-2650).

In the present invention, a mixture of adenoviruses of differing serotypes is pooled and is passaged, preferably at least twice, on a subconfluent culture of tumor cells at a particle per cell ratio high enough to encourage recombination between serotypes, but not so high as to produce premature cell death. A preferred particle per cell ratio is approximately 500 particles per cell, and is easily determined by one skilled in the art. As used herein, a "subconfluent culture" of cells refers to a monolayer or suspension culture in which the cells are actively growing. For cells grown as a monolayer, an example would be a culture where approximately 50% to 80% of the area available for cell growth is covered with cells. Preferred is a culture where approximately 75% of the growth area is covered with cells.

In a preferred embodiment, the adenoviral mixture is one that includes adenoviral serotypes representative of the adenoviral subgroups B, C, D, E and F. Group A adenoviruses are not included in the mixture as they are associated with tumor formation in rodents. Preferred tumor cell lines useful in the bioselection process include, but are not limited to, those derived from breast, colon, pancreas, lung and prostate. Some examples of solid tumor cell lines useful for the "bioselective" passaging of the adenoviral mixture include, but are not limited to, MDA231, HT29, PAN-1 and PC-3 cells. Hemopoietic cell lines include, but are not limited to, the Raji and Daudi B-lymphoid cells, K562 erythroblastoid cells, U937 myeloid cells, and HSB2 T-lymphoid cells.

Adenoviruses produced during these initial passages are used to infect quiescent tumor cells at a particle to cell ratio low enough to permit the infection of a cell by no more than one adenovirus. After up to 20 passages under these conditions, the supernatant from the last passage is harvested prior to visible cytopathic effect (CPE, see Fields Virology, Vol. 2, Fourth Edition, Knipe, ea., Lippincott Williams & Wilkins, pp. 135-136) to increase selection of highly potent viruses. The harvested supernatant can be concentrated by techniques well known to those skilled in the art. A preferred method for attaining quiescent cells, i.e. ones in which active cell growth has stopped, in a monolayer culture is to allow the culture to grow for 3 days following confluence, where confluence means that the entire area available for cell growth is occupied (covered with cells). Similarly, suspension cultures can be grown to densities characterized by the absence of active cell growth.

The serotype profile of the concentrated supernatant, which contains the bioselected adenoviral pool, can be examined by measuring the retention times of the harvested viral pool on an anion exchange column, where different adenoviral serotypes are known to have characteristic retention times (Blanche et al. (2000) *Gene Therapy* 7:1055-1062); see Example 3, FIGS. 1A and B. Adenoviruses of the invention can be isolated from the concentrated supernatant by dilution and plaque purification, or other techniques well know in the art, and grown for further characterization. Techniques well known in the art are used to determine the sequence of the isolated chimeric adenoviruses (see Example 5).

Figure 7:
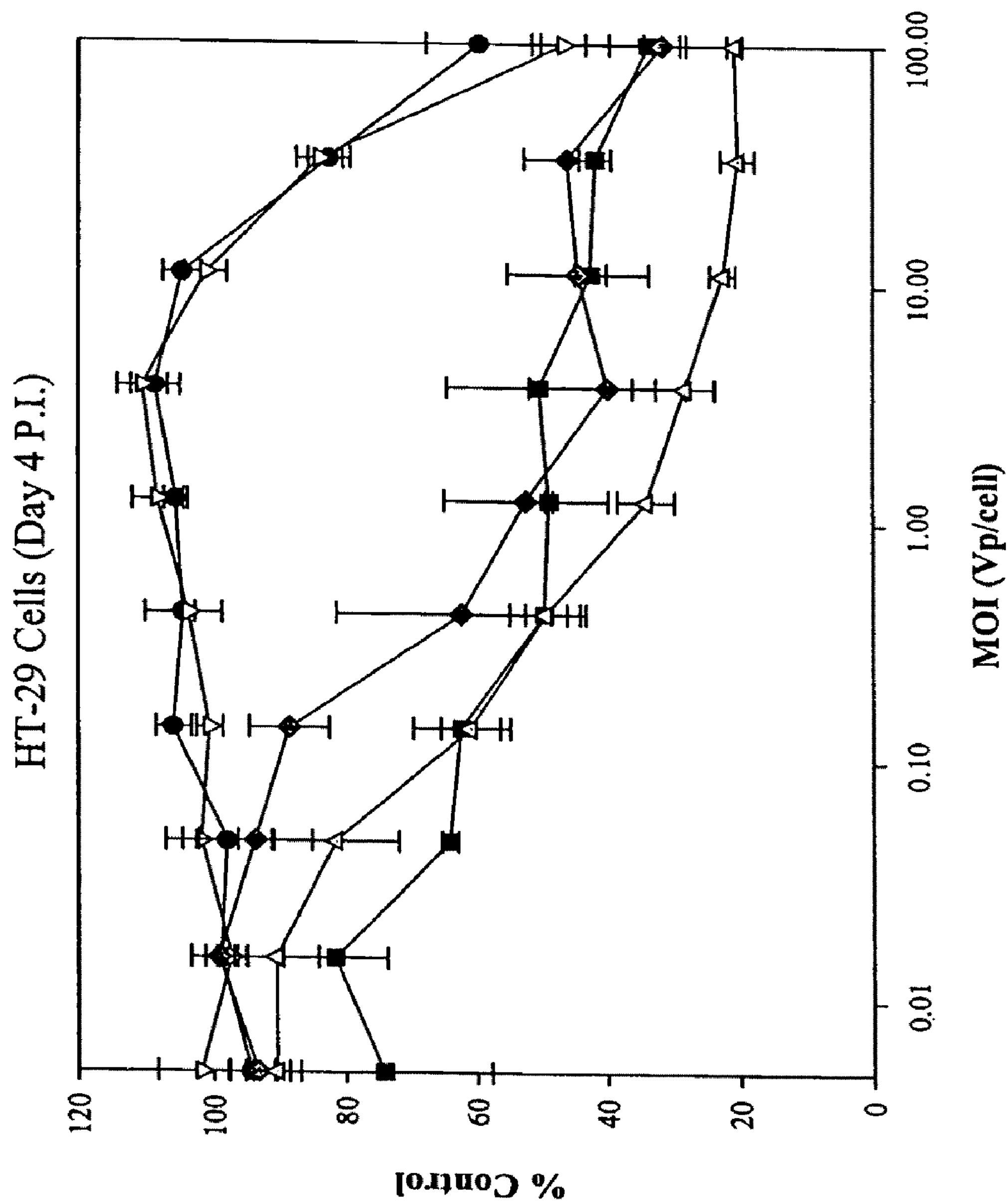
FIG. 7. Cytolytic activity of Recombinant Viruses. Recombinant viruses representing four viral populations (Adp11, ColoAd1, left end Ad11p/right end ColoAd1(ColoAd1.1) and left end ColoAd1/right end Ad11p (ColoAd1.2)) were constructed as described in Example 6. Cytolytic activity of each population in HT29 cells was determined as previously described. (Figure Legend: —•—Ad5; —□—Ad11p; —■—ColoAd1; —▲—ColoAd1.1; —υ—ColoAd1.2).

An example of a chimeric adenovirus of the invention is the chimeric adenovirus ColoAd1, which was isolated using HT29 colon cells in the bioselection process. ColoAd1 has the nucleic acid sequence of SEQ ID NO: 1. The majority of the nucleotide sequence of ColoAd1 is identical to the nucleotide sequence of the Ad11 serotype (SEQ ID NO: 2) (Stone et al. (2003) *Virology* 309:152-165; Mei et al. (2003) *J. Gen. Virology* 84:2061-2071). There are two deletions in the ColoAd1 nucleotide sequence as compared with Ad11, one 2444 base pairs in length within the E3 transcription unit region of the genome (base pairs 27979 to 30423 of SEQ ID NO: 2) and a second, smaller deletion, 25 base pairs in length (base pairs 33164 to 33189 of SEQ ID NO: 2), within the E4orf4 gene. The E2B transcription unit region (SEQ ID NO: 3) of ColoAd1, which encodes the adenoviral proteins DNA polymerase and terminal protein, is located between base pairs 5067 and 10354 of SEQ ID NO: 1, and is an area of homologous recombination between the Ad11 and Ad3 serotypes. Within this region of ColoAd1, there are 198 base pairchanges, as compared with the sequence of Ad11 (SEQ ID NO: 1). The changes result in stretches of nucleotides within the E2B region of ColoAd1 which are homologous to the sequence within a portion of the E2B region of Ad3 (SEQ ID NO: 8), with the longest stretch of homology between ColoAd1 and Ad3 being 414 bp in length. The E2B region of ColoAd1 (SEQ ID NO: 3) confers enhanced potency to the ColoAd1 adenovirus as compared to unmodified Ad11 adenovirus (see Example 6; FIG. 7). In other embodiments, a chimeric adenovirus of the invention can comprise nucleic acid sequences from more than two adenoviral serotypes.

Figure 3A:
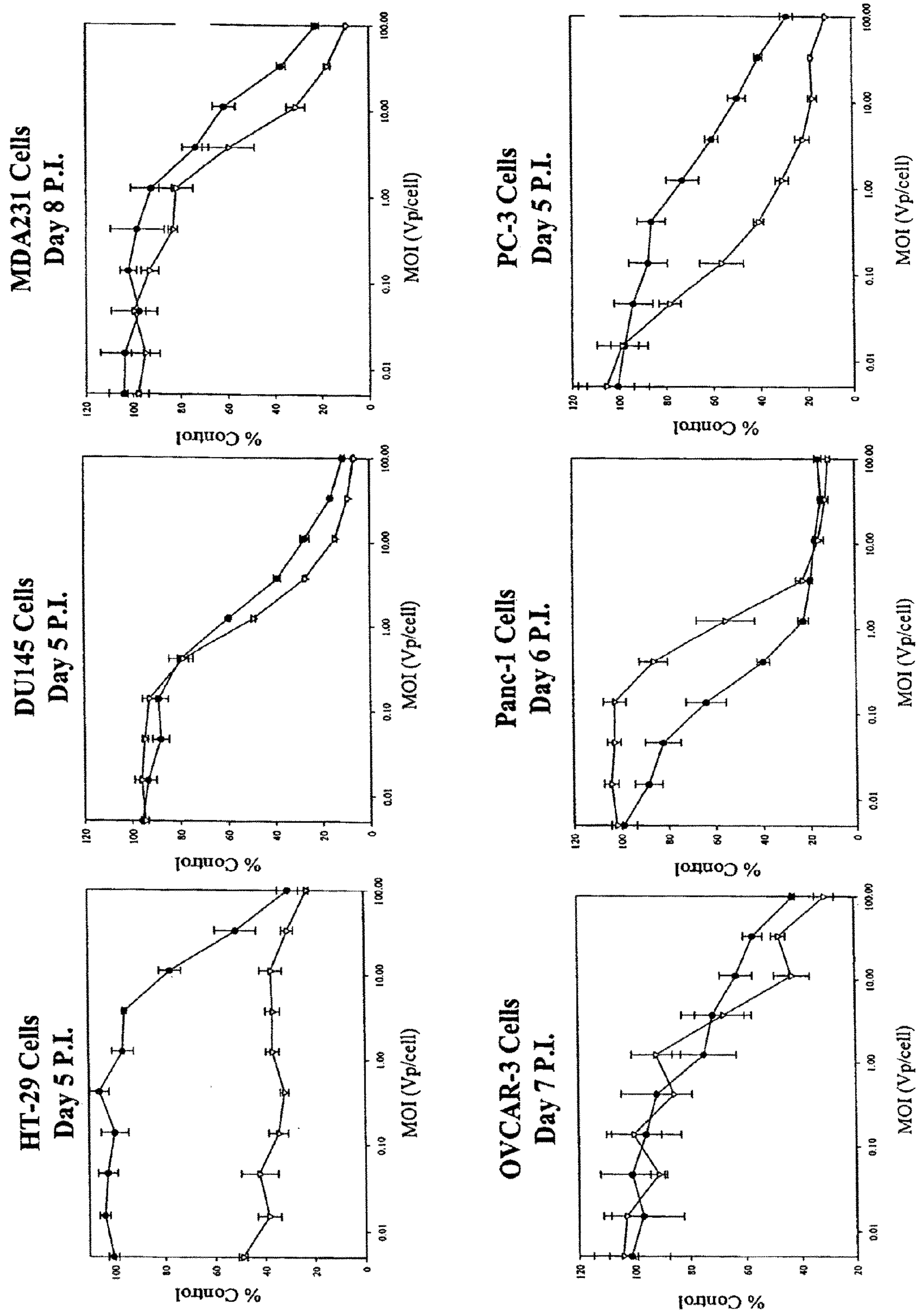
FIG. 3. Cytolytic activity of ColoAd1 and Ad5 on human tumor cell lines. An MTS assay was performed on A) a broad panel of human tumor cell lines and B) on a panel of human colon cancer cell lines to determine its potential potency specificity. The MTS assay was performed on differing days dependent upon the cell line. Each panel is a representative experiment that has been repeated at least three times. Each data point in the panel represents an assay done in quadruplicate and the results are expressed as the means+/−SD (Figure Legend: —•—Ad5; —□—ColoAd1).
Figure 3B:
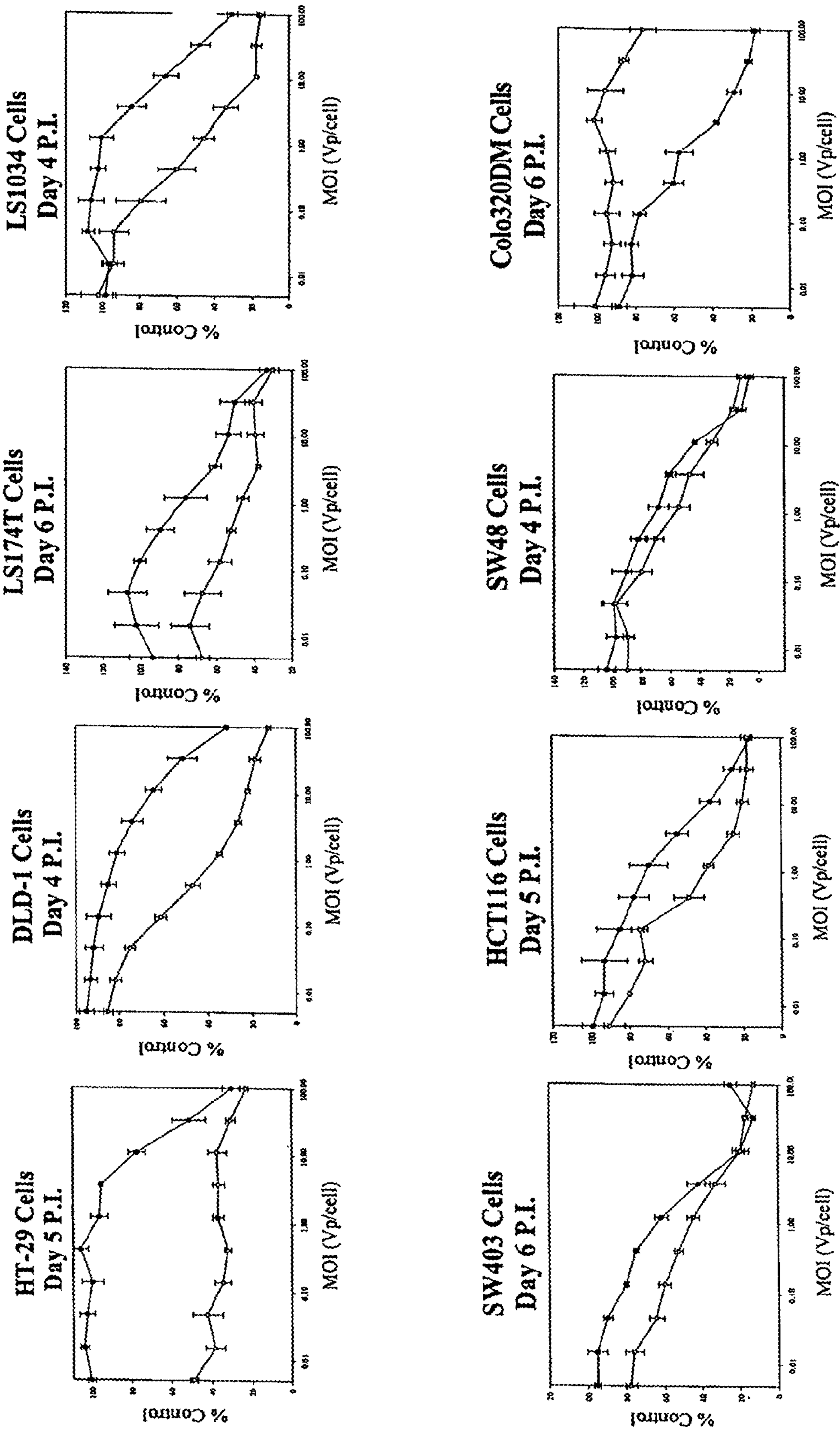

A chimeric adenovirus of the invention, or a variant or derivative thereof, can be evaluated for its selectivity in a specific tumor type by examination of its lytic potential in a panel of tumor cells derived from the same tissue upon which the adenoviral pool was initially passaged. For example, the chimeric adenovirus ColoAd1 (SEQ ID NO: 1), which was initially derived from an adenoviral pool passaged on HT-29 colon tumor cell lines, was reexamined both in HT-29 cells and in a panel of other colon-derived tumor cells lines, including DLD-1, LS174T, LS1034, SW403, HCT116, SW48, and Colo320DM (see FIG. 3B). Any available colon tumor cell lines would be equally useful for such an evaluation. Isolated adenoviral clones from adenoviral pools selected on other tumor cell types can be similarly tested in a suitable tumor cell panel, including, but not limited to, prostate cell lines (e.g. DU145 and PC-3 cell lines); pancreatic cell lines (e.g. the Panc-1 cell line); breast tumor cell lines (e.g. the MDA231 cell line) and ovarian cell lines (e.g. the OVCAR-3 cell line). Other available tumor cell lines are equally useful in isolating and identifying adenoviruses of the invention.

Figure 6:
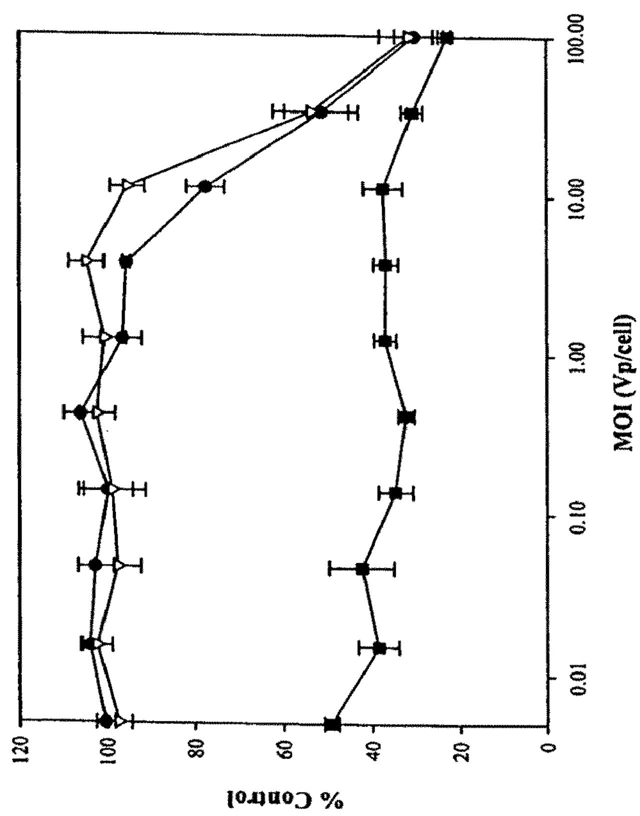
FIG. 6. Cytolytic activity of ColoAd1, Ad11p and Ad5 on a normal epithelial cell line (SAEC) and a human colon cancer cell line (HT-29). Each panel is a representative experiment that has been repeated at least three times. Each data point in the panel represents an assay done in quadruplicate and the results are expressed as the means+/−SD (Figure Legend: —•—Ad5; —□—Ad11p; —■—ColoAd1).
Figure 6:
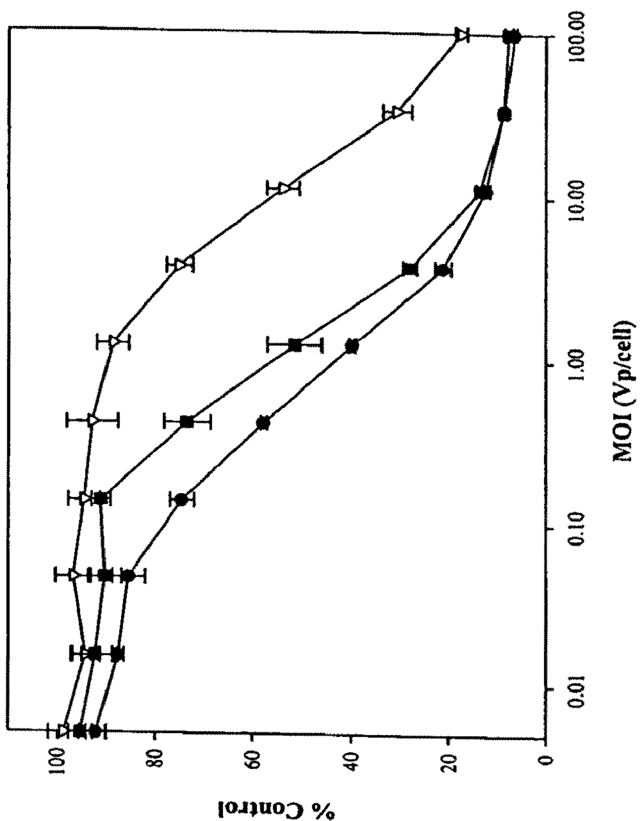

The chimeric adenoviruses of the invention have an enhanced therapeutic index as compared with the adenoviral serotypes from which it is derived. (see FIG. 6, which compares the cytolytic activity of the chimeric adenovirus ColoAd1 with Ad11p).

The invention also encompasses chimeric adenoviruses that are constructed using recombinant techniques well-known to those skilled in the art. Such chimeric adenoviruses comprise a region of nucleotide sequence derived from one adenoviral serotype which is incorporated by recombinant techniques into the genome of a second adenoviral serotype. The incorporated sequence confers a property, e.g. tumor specificity or enhanced potency, to the parental adenoviral serotype. For example, the E2B region of ColoAd1 (SEQ ID NO: 3) can be incorporated into the genome of Ad35 or Ad9.

Adenoviral Derivatives

The invention also encompasses a chimeric adenovirus of the invention that is modified to provide other therapeutically useful chimeric adenoviruses. Modifications include, but are not limited to, those described below.

One modification is production of derivatives of the chimeric adenovirus of the invention substantially lacking the ability to bind p53, as a result of a mutation in the adenoviral gene that encodes the E1B-55K protein. Such viruses generally have some, or all, of the E1B-55K region deleted. (see U.S. Pat. No. 5,677,178). U.S. Pat. No. 6,080,578 describes, among other things, Ad5 mutants that have deletions in the region of the E1B-55K protein that is responsible for binding p53. Another preferred modification to the chimeric adenoviruses of the instant invention are mutations in the E1A region, as described in U.S. Pat. Nos. 5,801,029 and 5,972,706. These types of modifications provide derivatives of the chimeric adenoviruses of the invention with greater selectivity for tumor cells.

Another example of a modification encompassed by the invention is a chimeric adenovirus which exhibits an enhanced degree of tissue specificity due to placement of viral replication under the control of a tissue specific promoter as described in U.S. Pat. No. 5,998,205. Replication of a chimeric adenovirus of the invention can also be put under the control of an E2F responsive element as described in U.S. patent application Ser. No. 09/714,409. This modification affords a viral replication control mechanism based on the presence of E2F, resulting in enhanced tumor tissue specificity, and is distinct from the control realized by a tissue specific promoter. In both of these embodiments, the tissue specific promoter and the E2F, responsive element are operably linked to an adenoviral gene that is essential for the replication of the adenovirus.

Another modification encompassed by the invention is use of a chimeric adenovirus of the invention, e.g. ColoAd1, as the backbone for production of novel replication-deficient adenoviral vectors. As described in Lai et al. ((2002) *DNA Cell Bio.* 21:895-913), adenoviral vectors which are replication deficient can be used to deliver and express therapeutic genes. Both first generation (in which the E1 and E3-regions are deleted) and second generation (in which the E4 region is additionally deleted) adenoviral vectors derived from the chimeric adenoviruses of the invention are provided herein. Such vectors are easily produced using techniques well known to those skilled in the art (see Imperiale and Kochanek (2004) *Curr. Top. Microbiol. Immunol.* 273:335-357; Vogels et al. (2003) *J. Virol.* 77:8263-8271).

A further modification encompassed by the invention is the insertion of a heterologous gene, useful as a marker or reporter for tracking the efficiency of viral infection. One embodiment of this type of modification is insertion of the thymidine kinase (TK) gene. The expression of TK within infected cells can be used to track the level of virus remaining in cells following viral infection, using radiolabeled substrates of the TK reaction (Sangro et al. (2002) *Mol. Imaging Biol.* 4:27-33).

Methods for the construction of the modified chimeric adenoviruses are generally known in the art. See, Mittal, S. K. (1993) *Virus Res.* 28:67-90 and Hermiston, T. et al. (1999) Methods in Molecular Medicine Adenovirus Methods and Protocols, W. S. M. Wold, ed, Humana Press. Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., Molecular Cloning: A Laboratory Manual, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation described below are those well known and commonly employed in the art.

Determination of Therapeutic Potential

Chimeric adenoviruses of the invention, or variants or derivatives thereof, can be evaluated for their therapeutic utility by examination of their lytic potential in tumor cells derived from tissues of interest as therapeutic targets. Tumor cell lines useful for testing such adenoviruses include, but are not limited to, colon cell lines, including but not limited to, DLD-1, HCT116, HT29, LS1034 and SW48 cell lines; prostate cell lines, including but not limited to, DU145 and PC-3 cell lines; pancreatic cell lines, including but not limited to, the Panc-1 cell line; breast tumor cell lines, including but not limited to, the MDA231 cell line and ovarian cell lines, including but not limited to, the OVCAR-3 cell line. Hemopoietic cell lines include, but are not limited to, the Raji and Daudi B-lymphoid cells, K562 erythroblastoid cells, U937 myeloid cells, and HSB2 T-lymphoid cells. Any other tumor cell lines that are available can be used in evaluating and identifying adenoviruses of the invention for use in the treatment of neoplasia.

Figure 2:
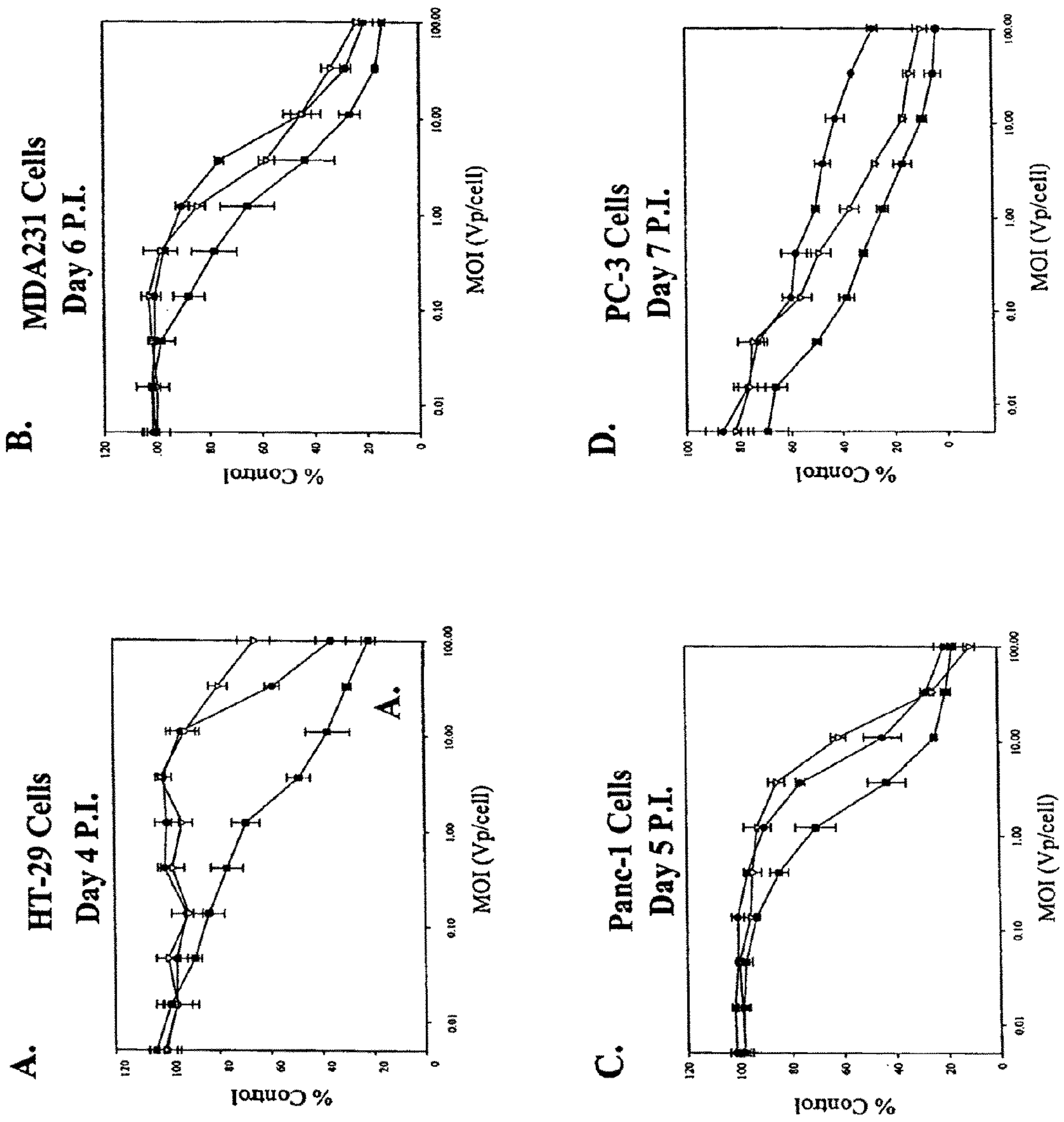
FIG. 2. Cytolytic activity of the individual virus pools. A) HT-29, B) MDA-231, C) Panc-1 and D) PC-3 cells were infected with their respective viral pools at VP per cell ratios from 100 to 0.01. MTS assays were performed on differing days post infection (as indicated) dependent upon the cell line. Each data point in the panel represents an assay done in quadruplicate and the results are expressed as the means+/−SD. The panel depicts one representative experiment and all viral pools were assayed at least three independent times on the target tumor cell line (Figure Legend: —•—Ad5; —□—initial viral pool; —■—specific cell derived pool, passage 20).

The cytolytic activity of adenoviruses of the invention can be determined in representative tumor cell lines and the data converted to a measurement of potency, with an adenovirus belonging to subgroup C, preferably Ad5, being used as a standard (i.e. given a potency of 1). A preferred method for determining cytolytic activity is an MTS assay (see Example 4, FIG. 2).

Figure 4:
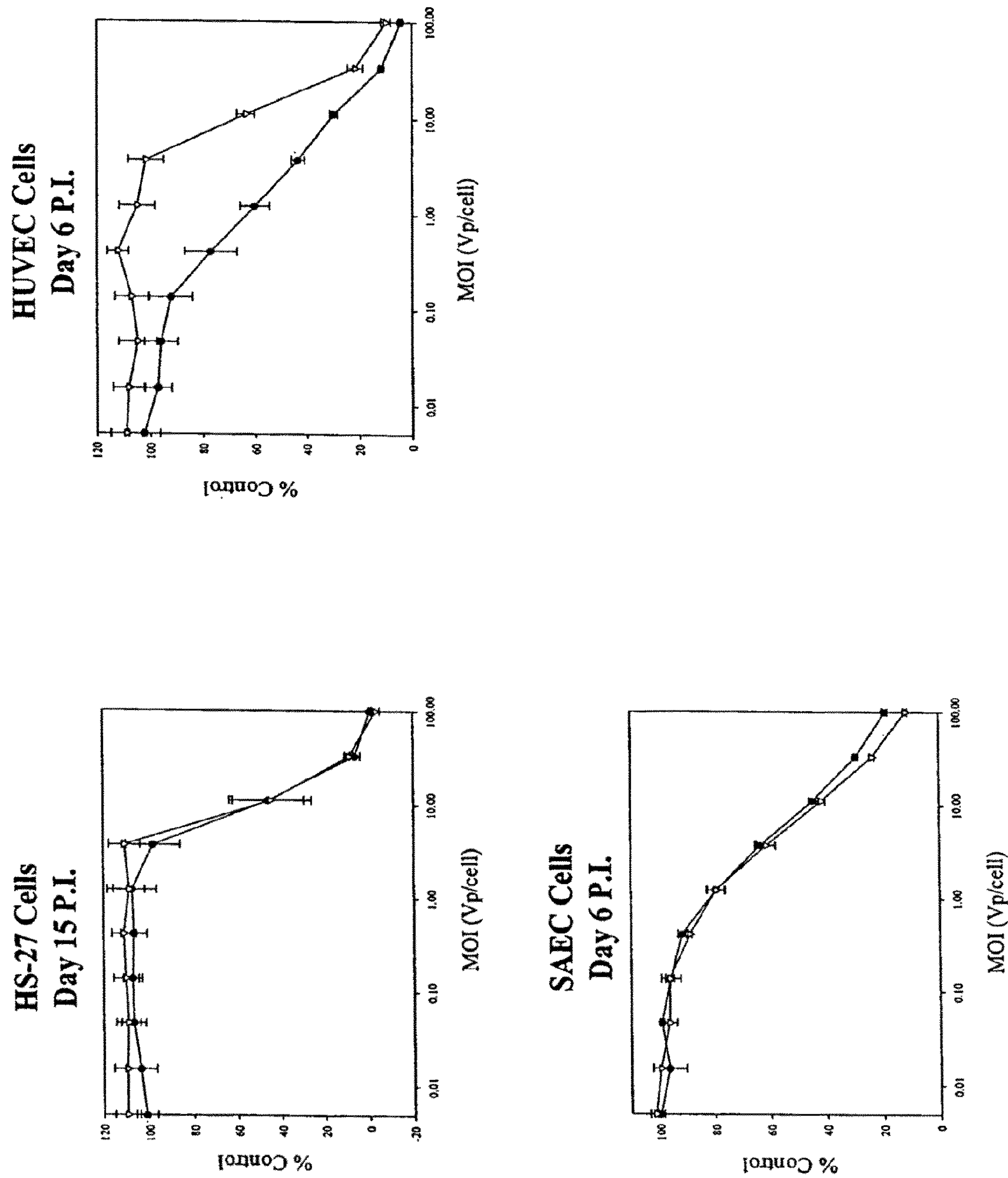
FIG. 4. Cytolytic activity of ColoAd1 and Ad5 on a panel of normal cells. HS-27, HUVEC and SAEC cells (primary fibroblast, endothelial, and epithelial cells, respectively) were infected with ColoAd1 and Ad5 at VP per cell ratios from 100 to 0.01. MTS assay was performed on differing days post infection dependent upon the cell and each panel is a representative experiment that has been repeated at least three times. Each data point in the panel represents an assay done in quadruplicate and the results are expressed as the means+/−SD (Figure Legend: —•—Ad5; —□—ColoAd1).
Figure 5:
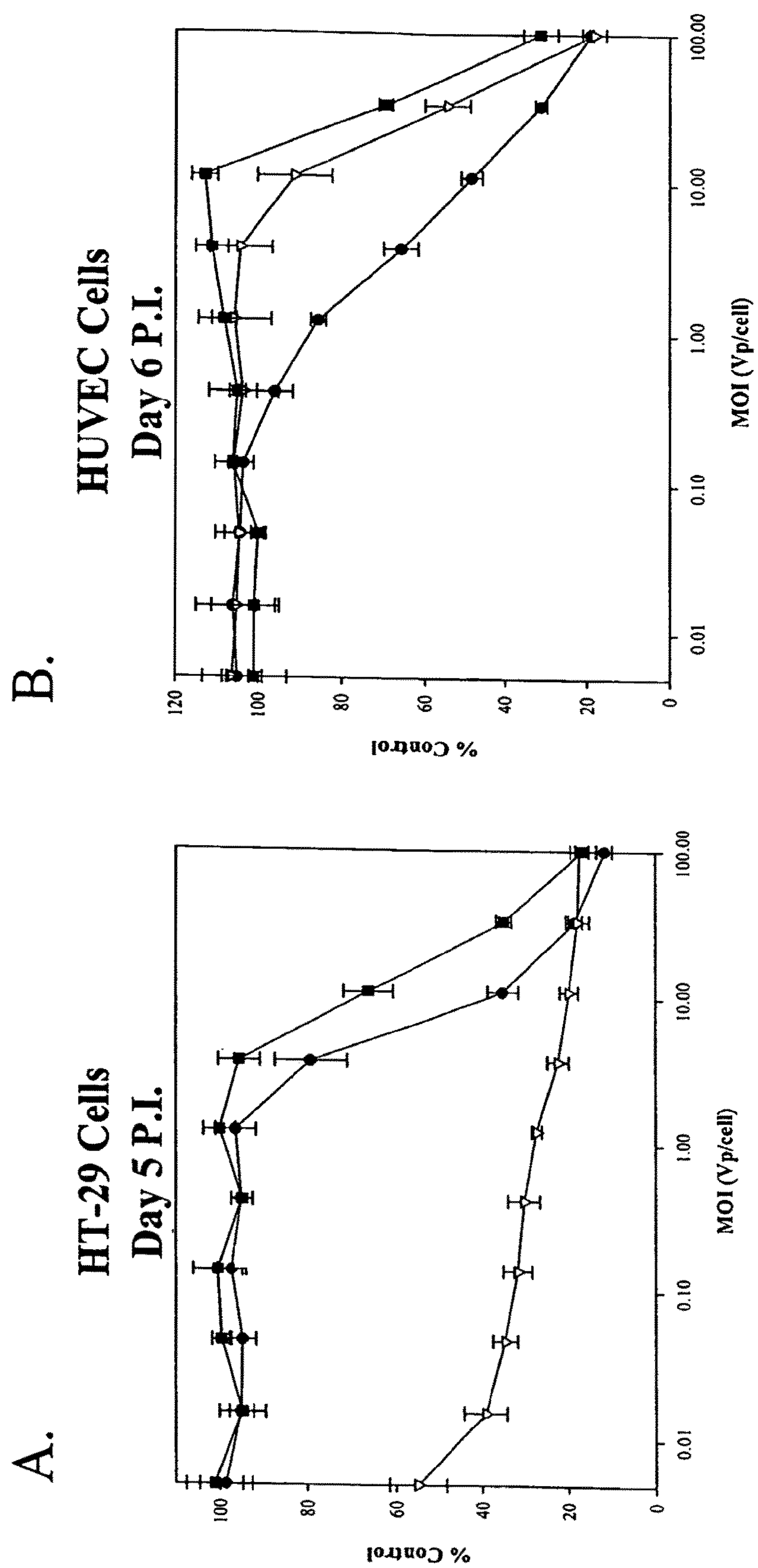
FIG. 5. Cytolytic activity of ColoAd1, Ad5 and ONYX-015 on primary normal endothelial cells (HUVEC) and a colon tumor cell line (HT-29). Each panel is a representative experiment that has been repeated at least three times. Each data point in the panel represents an assay done in quadruplicate and the results are expressed as the means+/−SD (Figure Legend: —•—Ad5; —□—ColoAd1; —■—Onyx-015).

The therapeutic index of an adenovirus of the invention in a particular tumor cell line can be calculated by comparison of the potency of the given adenovirus in a tumor cell line with the potency of that same adenovirus in a non-cancerous cell line. Preferred non-cancerous cell lines are SAEC cells, which are epithelial in origin, and HUVEC cells which are endothelial in origin (see FIG. 4). These two cell types represent normal cells from which organs and vasculature, respectively, are derived, and are representative of likely sites of toxicity during adenoviral therapy, depending on the mode of delivery of the adenovirus. However, practice of the invention is not limited to the use of these cells, and other non-cancerous cell lines (e.g. B cells, T cells, macrophages, monocytes, fibroblasts) may also be used.

The chimeric adenoviruses of the invention can be further evaluated for their ability to target neoplastic cell growth (i.e. cancer) by their capacity to reduce tumorigenesis or neoplastic cell burden in nude mice harboring a transplant of neoplastic cells, as compared to untreated mice harboring an equivalent neoplastic cell burden (see Example 7).

Evaluation of the adenoviruses of the invention can also be performed using primary human tumor explants (Lam et al. (2003) *Cancer Gene Therapy*; Grill et al. (2003) *Mol. Therapy* 6:609-614), which provide test conditions present in tumors that cannot normally be produced using the tumor xenograft studies.

Therapeutic Utility

The present invention provides for the use of chimeric adenoviruses of the invention for the inhibition of tumor cell growth, as well as for the use of adenoviral vectors derived from these chimeric adenoviruses to deliver therapeutic proteins useful in the treatment of neoplasia and other disease states.

Pharmaceutical Compositions and Administration

The present invention also relates to pharmaceutical compositions which comprise the chimeric adenoviruses of the invention, including variants and derivatives thereof, formulated for therapeutic administration to a patient. For therapeutic use, a sterile composition containing a pharmacologically effective dosage of adenovirus is administered to a human patient or veterinary non-human patient for treatment, for example, of a neoplastic condition. Generally, the composition will comprise about $10^{11}$ or more adenovirus particles in an aqueous suspension. A pharmaceutically acceptable carrier or excipient is often employed in such sterile compositions. A variety of aqueous solutions can be used, e.g. water, buffered water, 0.4% saline, 0.3%-glycine and the like. These solutions are sterile and generally free of particulate matter other than the desired adenoviral vector. The compositions may contain pharmaceutically acceptable auxiliary substances as required to approximate physiological conditions such as pH adjusting and buffering agents, toxicity adjusting agents and the like, e.g. sodium acetate, sodium chloride, potassium chloride, calcium chloride, sodium lactate, etc. Excipients which enhance infection of cells by adenovirus may be included. (see U.S. Pat. No. 6,392,069)

Adenoviruses of the invention may also be delivered to neoplastic cells by liposome or immunoliposome delivery; such delivery may be selectively targeted to neoplastic cells on the basis of a cell surface property present on the neoplastic cell population (e.g., the presence of a cell surface protein which binds an immunoglobulin in an immunoliposome). Typically, an aqueous suspension containing the virions are encapsulated in liposomes or immunoliposomes. For example, a suspension of adenovirus virions can be encapsulated in micelles to form immunoliposomes by conventional methods (U.S. Pat. No. 5,043,164, U.S. Pat. No. 4,957,735, U.S. Pat. No. 4,925,661; Connor and Huang, (1985) *J. Cell Biol.* 101: 581; Lasic D. D. (1992) *Nature* 355: 279; Novel Drug Delivery (eds. Prescott and Nimmo, Wiley, N.Y., 1989); Reddy et al. (1992) *J. Immunol* 148:1585). Immunoliposomes comprising an antibody that binds specifically to a cancer cell antigen (e.g., CALLA, CEA) present on the cancer cells of the individual may be used to target virions to those cells (Fisher (2001) *Gene Therapy* 8:341-348).

To further increase the efficacy of the adenoviruses of the invention, they may be modified to exhibit enhanced tropism for particular tumor cell types. For example, as shown in PCT/US98/04964, a protein on the exterior coat of an adenovirus may be modified to display a chemical agent, preferably a polypeptide, that binds to a receptor present on tumor cells to a greater degree than normal cells. (See also, U.S. Pat. Nos. 5,770,442 and 5,712,136). The polypeptide can be an antibody, and preferably is a single chain antibody.

Adenoviral Therapy

The adenoviruses of the invention, or pharmaceutical compositions thereof, can be administered for therapeutic treatment of neoplastic disease or cancer. In therapeutic applications, compositions are administered to a patient already affected by the particular neoplastic disease, in an amount sufficient to cure or at least partially arrest the condition and its complications. An amount adequate to accomplish this is defined as a "therapeutically effective dose" or "efficacious dose". Amounts effective for this use will depend upon the severity of the condition, the general state of the patient, and the route of administration.

For example, but not by way of limitation, a human patient or non-human mammal having a solid or haemotologic neoplastic disease, (e.g. pancreatic, colon, ovarian, lung, or breast carcinoma, leukemia or multiple myeloma) may be treated by administering a therapeutically effective dosage of an appropriate adenovirus of the invention, i.e. one which has been shown to have an improved therapeutic index for that tissue type. For example, a preferred chimeric adenovirus for the treatment of colon cancer would be the adenovirus ColoAd1 (SEQ ID NO: 1). Suspensions of infectious adenovirus particles may be delivered to neoplastic tissue by various routes, including intravenous, intraperitoneal, intramuscular, subdermal, and topical. An adenovirus suspension containing about $10^3$ to $10^{12}$ or more virion particles per ml may be administered by infusion (e.g., into the peritoneal cavity for treating ovarian cancer, into the portal vein for treating hepatocarcinoma or liver metastases from other non-hepatic primary tumors) or other suitable route, including direct injection into a tumor mass (e.g. a breast tumor), enema (e.g., colon cancer), or catheter (e.g., bladder cancer). Other routes of administration may be suitable for carcinomas of other origins, i.e. inhalation as a mist (e.g., for pulmonary delivery to treat bronchogenic carcinoma, small-cell lung carcinoma. non-small cell lung carcinoma, lung adenocarcinoma. or laryngeal cancer) or direct application to a tumor site (e.g., bronchogenic carcinoma, nasopharyngeal carcinoma, laryngeal carcinoma, cervical carcinoma).

Adenoviral therapy using the adenoviruses of the instant invention may be combined with other antineoplastic protocols, such as conventional chemotherapy or x-ray therapy to treat a particular cancer. Treatment can be concurrent or sequential. A preferred chemotherapeutic agent is cisplatin, and the preferred dose may be chosen by the practitioner based on the nature of the cancer to be treated, and other factors routinely considered in administering cisplatin. Preferably, cisplatin will be administered intravenously at a dose of 50-120 mg/m$^2$ over 3-6 hours. More preferably it is administered intravenously at a dose of 80 mg/m$^2$ over 4 hours. A second preferred chemotherapeutic agent is 5-fluorouracil, which is often administered in combination with cisplatin. The preferred dose of 5-fluorouracil is 800-1200 mg/m$^2$ per day for 5 consecutive days.

Adenoviral therapy using the adenoviruses of the instant invention as adenoviral vectors may also be combined with other genes known to be useful in viral based therapy. See U.S. Pat. No. 5,648,478. In such cases, the chimeric adenovirus further comprises a heterologous gene that encodes a therapeutic protein, incorporated within the viral genome, such that the heterologous gene is expressed within an infected cell. A therapeutic protein, as used herein, refers to a protein that would be expected to provide some therapeutic benefit when expressed in a given cell.

In one embodiment, the heterologous gene is a pro-drug activator gene, such as cytosine deaminase (CD) (See, U.S. Pat. Nos. 5,631,236; 5,358,866; and 5,677,178). In other embodiments, the heterologous gene is a known inducer of cell-death, e.g. apoptin or adenoviral death protein (ADP), or a fusion protein, e.g. fusogenic membrane glycoprotein (Danen-Van Oorschot et al. (1997) *Proc. Nat. Acad. Sci.* 94:5843-5847; Tollefson et al. (1996) *J. Virol.* 70:2296-2306; Fu et al. (2003) *Mol. Therapy* 7: 48-754, 2003; Ahmed et al. (2003) *Gene Therapy* 10:1663-1671, Galanis et al. (2001) *Human Gene Therapy* 12(7): 811-821).

Further examples of heterologous genes, or fragments thereof, include those that encode immunomodulatory proteins, such as cytokines or chemokines. Examples include interleukin 2, U.S. Pat. Nos. 4,738,927 or 5,641,665; interleukin 7, U.S. Pat. Nos. 4,965,195 or 5,328,988; and interleukin 12, U.S. Pat. No. 5,457,038; tumor necrosis factor alpha, U.S. Pat. Nos. 4,677,063 or 5,773,582; interferon gamma, U.S. Pat. Nos. 4,727,138 or 4,762,791; or GM CSF, U.S. Pat. Nos. 5,393,870 or 5,391,485, Mackensen et al. (1997) *Cytokine Growth Factor Rev.* 8:119-128). Additional immunomodulatory proteins further include macrophage inflammatory proteins, including MIP-3. Monocyte chemotatic protein (MCP-3 alpha) may also be used; a preferred embodiment of a heterologous gene is a chimeric gene consisting of a gene that encodes a protein that traverses cell membranes, for example, VP22 or TAT, fused to a gene that encodes a protein that is preferably toxic to cancer but not normal cells.

The chimeric adenoviruses of the invention can also be used as vectors to deliver genes encoding therapeutically useful RNA molecules, i.e. siRNA (Dorsett and Tuschl (2004) *Nature Rev Drug Disc* 3:318-329).

In some cases, genes can be incorporated into a chimeric adenovirus of the invention to further enhance the ability of the oncolytic virus to eradicate the tumor, although not having any direct impact on the tumor itself—these include genes encoding proteins that compromise MHC class I presentation (Hewitt et al. (2003) *Immunology* 110: 163-169), block complement, inhibit IFNs and IFN-induced mechanisms, chemokines and cytokines, NK cell based killing (Orange et al., (2002) *Nature Immunol.* 3:1006-1012; Mireille et al. (2002) *Immunogenetics* 54: 527-542; Alcami (2003) *Nature Rev. Immunol.* 3: 36-50; down regulate the immune response (e.g. IL-10, TGF-Beta, Khong and Restifo (2002) *Nature Immunol.* 3: 999-1005; 2002) and metalloproteases which can breakdown the extracellular matrix and enhance spread of the virus within the tumor (Bosman and Stamenkovic (2003) *J. Pathol.* 2000: 423-428; Visse and Nagase (2003) *Circulation Res.* 92: 827-839).

Kits

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

The present invention is further described by the following examples, which are illustrative of specific embodiments of the invention, and various uses thereof. These exemplifications, which illustrating certain specific aspects of the invention, do not portray the limitations or circumscribe the scope of the disclosed invention.

Unless otherwise Indicated, the practice of the present Invention employs conventional techniques of cell culture, molecular biology, microbiology, recombinant DNA manipulation, immunology science, which are within the skill of the art. Such techniques are explained fully in the literature. See, e.g. Cell Biology: a Laboratory Handbook: J. Celis (Ed) Academic Press. N.Y. (1996); Graham, F. L. and Prevec, L. Adenovirus-based expression vectors and recombinant vaccines. In: Vaccines: New Approaches to Immunological Problems. R. W. Ellis (ed) Butterworth. Pp 363-390; Grahan and Prevec Manipulation of adenovirus vectors. In: Methods in Molecular Biology, Vol. 7: Gene Transfer and Expression Techniques. E. J. Murray and J. M. Walker (eds) Humana Press Inc., Clifton, N.J. pp 109-128, 1991; Sambrook et al. (1989), Molecular Cloning, A Laboratory Manual, 2nd ed., Cold Spring Harbor Laboratory Press; Sambrook et al. (1989), and Ausubel et al. (1995), Short Protocols in Molecular Biology, John Wiley and Sons.

EXAMPLES

Methods

Standard techniques are used for recombinant nucleic acid methods, polynucleotide synthesis, and microbial culture and transformation (e.g., electroporation, lipofection). Generally, enzymatic reactions and purification steps are performed according to the manufacturer's specifications. The techniques and procedures are generally performed according to conventional methods in the art and various general references (see generally, Sambrook et al., Molecular Cloning: A Laboratory Manual, 2nd. edition (1989) Cold Spring Harbor Laboratory Press, Cold Spring Harbor, N.Y.) which are provided throughout this document. The nomenclature used herein and the laboratory procedures in analytical chemistry, organic synthetic chemistry, and pharmaceutical formulation and delivery, and treatment of patients. Methods for the construction of adenoviral mutants are generally known in the art. See, Mittal, S. K., Virus Res., 1993, vol: 28, pages 67-90; and Hermiston, T. et al., Methods in Molecular Medicine: Adenovirus Methods and Protocols, W. S. M. Wold, ed, Humana Press, 1999. Further, the adenovirus 5 genome is registered as Genbank 10 accession #M73260, and the virus is available from the American Type Culture Collection, Rockville, Md., U.S.A., under accession number VR-5.

Viruses and Cell Lines

The Ad serotypes Ad3 (GB strain), Ad4 (RI-67 strain), Ad5 (Adenoid 75 strain), Ad9 (Hicks strain), Ad11p (Slobitski strain), Ad16 (Ch. 79 strain) and all the cell lines, with the exception of the following were all purchased from the ATCC: MDA231-mt1 (a derivative isolated by Dr. Deb Zajchowski from a rapidly growing subcutaneous implanted xenograft of MDA231 cells) and Panc1-sct (derived by Dr. Sandra Biroc from a rapidly growing subcutaneous implanted xenograft of Panc1 cells), HUVEC (Vec Technologies, Rensselaer, N.Y.), and SAEC (Clonetics, Walkersville, Md.). Ad40 was a kind gift from Dr. William S. M. Wold at St. Louis University.

Example 1

Viral Purification and Quantitation

Viral stocks were propagated on 293 cells and purified on CsCl gradients (Hawkins et al., 2001). The method used to quantitate viral particles is based on that of Shabram et al. (1997) *Human Gene Therapy* 8:453-465, with the exception that the anion-exchanger TMAE Fractogel was used instead of Resource Q. In brief, a 1.25 ml column was packed with Fractogel EMD TMAE-650 (S) (catalog #116887-7 EM Science, Gibbstown, N.J. 08027). HPLC separation was performed on an Agilent HP 1100 HPLC using the following conditions: Buffer A=50 mM HEPES, pH 7.5; Buffer B=1.0 M NaCl in Buffer A; flow rate of 1 ml per minute. After column equilibration for not less than 30 minutes in Buffer A, approximately $10^9$-$10^{11}$ viral particles of sample were loaded onto the column in 10-100 ul volume, followed by 4 column volumes of Buffer A. A linear gradient extending over 16 column volumes and ending in 100% Buffer B was applied.

The column effluent was monitored at A260 and A280 nm, peak areas calculated, and the 260 to 280 nm ratio determined. Viral peaks were identified as those peaks having a A260/A280 ratio close to 1.33. A virus standard was included with each sample series. The number of viral particles per ml of the standard had been determined using the method of Lehmberg et al. (1999) *J. Chrom. B,* 732:411-423). In the viral concentration range used, the A260 nm peak area of each sample is directly proportional to the number of viral particles in the sample. The number of viral particles per ml in each test sample was calculated by multiplying the known number of viral particles per ml in the standard by the ratio of the A260 nm viral peak area of the sample to the A260 nm viral peak area of the standard.

The column was regenerated after each sample gradient by washing with two column volumes of 0.5 N NaOH followed by two column volumes of 100% Buffer A, 3 column volumes of 100% Buffer B, and then 4 column volumes of 100% Buffer A.

Example 2

Bioselection

Viral serotypes representing subgroups Ads B-F were pooled and passaged on sub-confluent cultures of the target tumor cell lines at a high particle-per-cell ratio for two rounds to invite recombination to occur between serotypes. Supernatant (1.0, 0.1 0.01, 0.001 ml) from the second round of the high viral particle-per-cell infection, subconfluent cultures, was then used to infect a series of over-confluent T-75 tissue culture flasks of target tumor cell lines PC-3, HT-29, Panc-1 and MDA-231. To achieve over-confluency, each cell line was seeded at split ratios that allowed that cell line to reach confluency between 24 and 40 hours post seeding, and the cells were allowed to grow a total of 72 hours post seeding prior to infection. This was done to maximize the confluency of the cells to mimic growth conditions in human solid tumors.

Cell culture supernatant was harvested from the first flask in the 10-fold dilution series that did not show any sign of CPE at day 3 or 4 post-infection (in the case of HT-29 and PC-3, this was modified for passages 10-20 to harvest of the second flask, i.e. harvest 100-fold below the dilution in which CPE were detectable by day 3 post-infection). Each harvest served as the starting material for the successive passage of the virus. This process was repeated until the viral pool achieved 20 bioselective passages.

Individual viruses from each bioselected pool were isolated by two rounds of plaque purification on A549 cells using standard methods (Tollefson, A., Hermiston, T. W., and Wold, W. S. M.; "Preparation and Titration of CsCl-banded Adenovirus Stock" in *Adenovirus Methods and Protocols*, Humana Press, 1999, pp 1-10, W. S. M. Wold, Ed). In brief, dilutions of the supernatant harvested from the $20^{th}$ passage on each target tumor line were used to infect A549 cells in a standard plaque assay. Well-individuated plaques were harvested, and the same plaque assay method was used to generate a second round of individual plaques from these harvests. Well isolated plaques from the second round of plaque purification were deemed pure, infected cultures were prepared using these purified plaques, and the oncolytic potency of these culture supernatants determined by MTS assay as described.

Example 3

Serotype Characterization

Figure 1B:
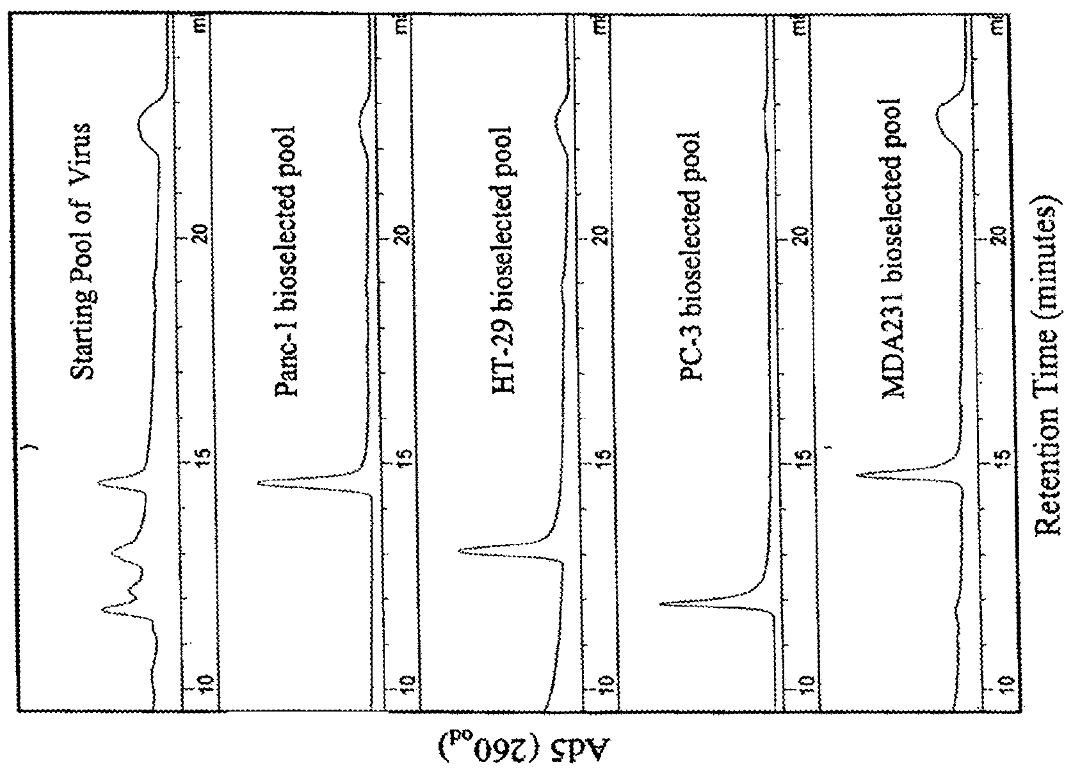

The parental adenoviral serotypes comprising the viral pools or the isolated ColoAd1 adenovirus were identified using anion-exchange chromatography similar to that described in Shabram et al. (1997) *Human Gene Therapy* 8:453:465, with the exception that the anion-exchanger TMAE Fractogel media (EM Industries, Gibbstown, N.J.) was used instead of Resource Q, as described in Example 1 (see FIG. 1).

Adenovirus type 5 eluted at approximately 60% Buffer B during the gradient. The other serotypes (3, 4, 9, 11p, 16, 35, and 40) each eluted at a characteristic retention time consistent with the retention times on Q Sepharose XL published by Blanche et al. (2000) *Gene Therapy* 7:1055-1062.

Example 4

Cytolytic Assay

The viral lytic capacity was measured by using a modification of the MTT assay (Shen et al., 2001). Briefly, the MTS assay (Promega, CellTiter 96$^{00}$ Aqueous Non-Radioactive Cell Proliferation Assay) was used in place of the MTT assay since conversion of MTS by cells Into aqueous, soluble formazan reduces time and eliminates the use of a volatile organic solvent associated with the MTT assay.

To perform the assay, cells were seeded at a defined density for each tumor cell line that generated a confluent monolayer within 24 hr. These densely seeded cells were allowed to grow for 2 additional days prior to exposure to the test virus(es). Infections of both tumor and primary normal cells were carried out in quadruplicate with serial three fold dilutions of the viruses starting at a particle per cell ratio of 100 and ending at a particle per cell ratio of 0.005. Infected cells were incubated at 37° C. and the MTS assay was performed at the time points indicated for the individual primary cells or tumor cell lines. Mock-infected cells served as negative controls and established the 100% survival point for the given assay.

Example 5

DNA Sequencing

DNA sequencing of the Ad11p (SEQ ID NO: 2) and ColoAd1 (SEQ ID NO: 1) genomic DNAs was performed as follows. Briefly, purified adenovirus DNA from ColoAd1 and Ad11p was partially digested with the restriction endonuclease Sau3A1 and shotgun cloned into the plasmid vector pBluescript II (Stratagene, La Jolla, Calif.). Positive clones were propagated and sequenced using the primers M13R and KS (Stratagene, La Jolla, Calif.). Individual sequence reactions were trimmed, edited and assembled using Sequencher™ (Gene Codes Corp., Ann Arbor, Mich.). Gaps in coverage were amplified with custom oligonucleotide primers and sequenced. The ends of the viral genomes were sequenced directly off the adenoviral DNA. In all, each genome was sequenced at 3×+ coverage and 431 bases at 2× coverage.

To determine the origin of the ColoAd1 E2B region, two primer sets were generated, one to the E2B pTP gene (bp9115, 5'GGGAGTTTCGCGCGGACACGG3' (SEQ ID NO: 4) and bp 9350, 5' GCGCCGCCGCCGCG-GAGAGGT3' (SEQ ID NO: 5)) and one to the DNA polymerase gene (bp 7520 5'CGAGAGCCCATTCGTGCAGGT-GAG3' (SEQ ID NO: 6) and bp 7982, 5'GCTGCGACTACTGCGGCCGTCTGT3' (SEQ ID NO: 7) and used to PCR isolate DNA fragments from the various serotypes (Ad3, 4, 5, 9, 11p, 16 and 40) using reagents from the Advantage 2 PCR kit (Clonetics, Walkersville, Md.; Cat #K1910-Y) and run on a PTC-200 thermocycler from MJ Research (Watertown, Mass.). These fragments were subsequently sequenced along with the DNA sequence of Ad3 using dye terminator sequencing on as ABI 3100 genetic analyzer.

The E2B region of Ad3 was sequenced using isolated Ad3 DNA and overlapping primers.

Sequence information was analyzed using the Vector NTI program (Informatix).

Example 6

Construction of Recombinant Viruses

Genomic DNAs of Ad11p (SEQ ID NO: 2) and ColoAd1 (SEQ ID NO: 1) were purified from CsCl gradient-banded virus particles. The genomic DNAs were digested with ParI which cuts each only once within the viral genome. The Pac1 cut occurs at base 18141 on ColoAd1 nucleotide sequence (SEQ ID NO: 1) and at base 18140 on the Ad11 nucleotide sequence (SEQ ID NO: 2). Digested DNAs were mixed in equal amounts and ligated in the presence of T4 DNA ligase at 16° C. overnight. This ligation mixture was transfected into A549 cells using the $CaPO_4$ transfection kit from Invitrogen, Carlsbad, Calif. (Cat #K2780-01). Isolated plaques were picked and screened by restriction enzyme digestion and PCR analysis to distinguish the four viral populations (Ad11p, ColoAd1, left end Ad11p/right end ColoAd1 (ColoAd1.1) and left end ColoAd1/right end Ad11p(ColoAd1.2)).

The viral lytic capacity of each population was determined in several cell lines, including HT29 and HUVEC cell lines, as described in Example 3. The results demonstrated the order of potency, from least potent to most potent, as Ad11p, ColoAd1.2, ColoAd1.1, ColoAd1 (see FIG. 7 for the results in HT29 cells).

Also constructed were chimeric adenoviruses pCJ144 and pCJ146, which contain the full-length ColoAd1 genome in which the wild-type Ad11p E3 and E4 region, respectively, has been restored. These modifications were introduced by homologous recombination into BJ5183 E. Coli (Chartier et al. (1996) *J. Virol.* 70:4805-4810). Both of these chimeric adenoviruses demonstrated reduced lytic capacity in HT29 and HUVEC cells compared to ColoAd1 or ColoAd1.2.

Example 7

In Vivo Efficacy of Adenovirus

In a typical human tumor xenograft nude mouse experiment, animals are injected with $5\times10^6$ cells subcutaneously into the hind flank of the mouse. When the tumors reach 100-200 ul in size, they are injected with vehicle (PBS) or with virus at $2\times10^{10}$ particles for five consecutive days ($1\times10^{11}$ particles total). A reduction in the size of the tumor would be noted relative to the PBS control and additional control viruses (Ad5, ONYX-015).

Example 8

ColoAd1 Selectivity on Primary Human Tissue Explants

Tissue specimens from colorectal tumors and adjacent normal tissues removed during surgery were placed in culture media and infected with equal numbers of either ColoAd1 or Ad5 viruses. Culture supernatants were collected at 24 hours post infection and the number of virus particles produced was determined. ColoAd1 produced more virus particles per input particle than Ad5 on tumor tissue, while it produced fewer particles per input particle than Ad5 on normal tissue.

We claim:

1. A method of inhibiting growth of a cancer cell, comprising infecting said cancer cell with a chimeric adenovirus having a genome comprising an E2B region, wherein:

the E2B region comprises a nucleic acid sequence that encodes the amino acid sequence encoded by SEQ ID NO:3; and the chimeric adenovirus is oncolytic and demonstrates an enhanced therapeutic index for a tumor cell.

2. The method of claim 1, wherein said cancer cell is a colon cancer cell.

3. The method of claim 2, wherein the nucleotide sequence of said adenovirus comprises SEQ ID NO: 1.

4. The method of claim 1 wherein the adenovirus comprises an E2B nucleotide sequence comprising SEQ ID NO:3.

5. The method of claim 1 wherein the adenovirus comprises a nucleotide sequence comprising SEQ ID NO:1.

6. The method of claim 1, wherein the adenovirus further comprises regions encoding fiber, hexon, and penton proteins, wherein the nucleic acid encoding the fiber, hexon, and penton proteins of the adenovirus are from the same adenoviral serotype.

7. The method of claim 1 wherein the tumor cell is a colon, breast, pancreas, lung, prostate, ovarian, or hematopoietic tumor cell.

8. The method of claim 7 wherein the tumor cell is a colon tumor cell.

* * * * *

SEQUENCE LISTING

```
<160> NUMBER OF SEQ ID NOS: 8

<210> SEQ ID NO 1
<211> LENGTH: 32325
<212> TYPE: DNA
<213> ORGANISM: Adenovirus

<400> SEQUENCE: 1

ctatctatat aatatacctt atagatggaa tggtgccaat atgtaaatga ggtgatttta     60

aaaagtgtgg atcgtgtggt gattggctgt ggggttaacg gctaaaaggg gcggtgcgac    120

cgtgggaaaa tgacgttttg tgggggtgga gtttttttgc aagttgtcgc gggaaatgtg    180

acgcataaaa aggctttttt ctcacggaac tacttagttt tcccacggta tttaacagga    240

aatgaggtag ttttgaccgg atgcaagtga aaattgttga ttttcgcgcg aaaactgaat    300

gaggaagtgt ttttctgaat aatgtggtat ttatggcagg gtggagtatt tgttcagggc    360

caggtagact ttgacccatt acgtggaggt ttcgattacc gtgtttttta cctgaatttc    420

cgcgtaccgt gtcaaagtct tctgttttta cgtaggtgtc agctgatcgc tagggtattt    480

atacctcagg gtttgtgtca agaggccact cttgagtgcc agcgagaaga gttttctcct    540

ctgcgccggc agtttaataa taaaaaaatg agagatttgc gatttctgcc tcaggaaata    600

atctctgctg agactggaaa tgaaatattg gagcttgtgg tgcacgccct gatgggagac    660

gatccggagc cacctgtgca gctttttgag cctcctacgc ttcaggaact gtatgattta    720

gaggtagagg gatcggagga ttctaatgag gaagctgtaa atggcttttt taccgattct    780

atgcttttag ctgctaatga agggttagaa ttagatccgc ctttggacac ttttgatact    840

ccaggggtaa ttgtggaaag cggtacaggt gtaagaaaat tacctgattt gagttccgtg    900

gactgtgatt tgcactgcta tgaagacggg tttcctccga gtgatgagga ggaccatgaa    960

aaggagcagt ccatgcagac tgcagcgggt gagggagtga aggctgccaa tgttggtttt   1020

cagttggatt gcccggagct tcctggacat ggctgtaagt cttgtgaatt tcacaggaaa   1080

aatactggag taaaggaact gttatgttcg ctttgttata tgagaacgca ctgccacttt   1140

atttacagta agtgtgttta agttaaaatt taaaggaata tgctgttttt cacatgtata   1200

ttgagtgtga gttttgtgct tcttattata ggtcctgtgt ctgatgctga tgaatcacca   1260

tctcctgatt ctactacctc acctcctgag attcaagcac ctgttcctgt ggacgtgcgc   1320

aagcccattc ctgtgaagct taagcctggg aaacgtccag cagtggaaaa acttgaggac   1380

ttgttacagg gtggggacgg acctttggac ttgagtacac ggaaacgtcc aagacaataa   1440

gtgttccata tccgtgttta cttaaggtga cgtcaatatt tgtgtgacag tgcaatgtaa   1500

taaaaatatg ttaactgttc actggttttt attgcttttt gggcggggac tcaggtatat   1560

aagtagaagc agacctgtgt ggttagctca taggagctgg ctttcatcca tggaggtttg   1620

ggccattttg gaagacctta ggaagactag gcaactgtta gagaacgctt cggacggagt   1680

ctccggtttt tggagattct ggttcgctag tgaattagct agggtagttt ttaggataaa   1740

acaggactat aaacaagaat ttgaaaagtt gttggtagat tgcccaggac tttttgaagc   1800
```

```
tcttaatttg ggccatcagg ttcactttaa agaaaaagtt ttatcagttt tagacttttc   1860
aaccccaggt agaactgctg ctgctgtggc ttttcttact tttatattag ataaatggat   1920
cccgcagact catttcagca ggggatacgt tttggatttc atagccacag cattgtggag   1980
aacatggaag gttcgcaaga tgaggacaat cttaggttac tggccagtgc agcctttggg   2040
tgtagcggga atcctgaggc atccaccggt catgccagcg gttctggagg aggaacagca   2100
agaggacaac ccgagagccg gcctggaccc tccagtggag gaggcggagt agctgacttg   2160
tctcctgaac tgcaacgggt gcttactgga tctacgtcca ctggacggga taggggcgtt   2220
aagagggaga gggcatctag tggtactgat gctagatctg agttggcttt aagtttaatg   2280
agtcgcagac gtcctgaaac catttggtgg catgaggttc agaaagaggg aagggatgaa   2340
gtttctgtat tgcaggagaa atattcactg gaacaggtga aaacatgttg gttggagcct   2400
gaggatgatt gggaggtggc cattaaaaat tatgccaaga tagctttgag gcctgataaa   2460
cagtataaga ttactagacg gattaatatc cggaatgctt gttacatatc tggaaatggg   2520
gctgaggtgg taatagatac tcaagacaag gcagttatta gatgctgcat gatggatatg   2580
tggcctgggg tagtcggtat ggaagcagta actttgtaa atgttaagtt taggggagat   2640
ggttataatg gaatagtgtt tatggccaat accaaactta tattgcatgg ttgtagcttt   2700
tttggtttca acaatacctg tgtagatgcc tggggacagg ttagtgtacg ggatgtagt   2760
ttctatgcgt gttggattgc cacagctggc agaaccaaga gtcaattgtc tctgaagaaa   2820
tgcatatttc aaagatgtaa cctgggcatt ctgaatgaag gcgaagcaag ggtccgccac   2880
tgcgcttcta cagatactgg atgttttatt ttgattaagg gaaatgccag cgtaaagcat   2940
aacatgattt gcggtgcttc cgatgagagg ccttatcaaa tgctcacttg tgctggtggg   3000
cattgtaata tgctggctac tgtgcatatt gtttcccatc aacgcaaaaa atggcctgtt   3060
tttgatcaca atgtgatgac gaagtgtacc atgcatgcag gtgggcgtag aggaatgttt   3120
atgccttacc agtgtaacat gaatcatgtg aaagtgttgt tggaaccaga tgccttttcc   3180
agaatgagcc taacaggaat ttttgacatg aacatgcaaa tctggaagat cctgaggtat   3240
gatgatacga gatcgagggt acgcgcatgc gaatgcggag gcaagcatgc caggttccag   3300
ccggtgtgtg tagatgtgac tgaagatctc agaccggatc atttggttat tgcccgcact   3360
ggagcagagt tcggatccag tggagaagaa actgactaag gtgagtattg ggaaaacttt   3420
ggggtgggat tttcagatgg acagattgag taaaaatttg ttttttctgt cttgcagctg   3480
tcatgagtgg aaacgcttct tttaaggggg gagtcttcag ccccttatctg acagggcgtc   3540
tcccatcctg ggcaggagtt cgtcagaatg ttatgggatc tactgtggat ggaagacccg   3600
tccaacccgc caattcttca acgctgacct atgctacttt aagttcttca cctttggacg   3660
cagctgcagc tgccgccgcc gcttctgttg ccgctaacac tgtgcttgga atgggttact   3720
atggaagcat catggctaat tccacttcct ctaataaccc ttctaccctg actcaggaca   3780
agttacttgt ccttttggcc cagctggagg ctttgaccca acgtctgggt gaactttctc   3840
agcaggtggt cgagttgcga gtacaaactg agtctgctgt cggcacggca aagtctaaat   3900
aaaaaaatcc cagaatcaat gaataaataa acaagcttgt tgttgattta aaatcaagtg   3960
tttttatttc atttttcgcg cacggtatgc cctagaccac cgatctctat cattgagaac   4020
tcggtggatt ttttccagga tcctatagag gtgggattga atgtttagat acatgggcat   4080
taggccgtct ttggggtgga gatagctcca ttgaagggat tcatgctccg ggtagtgtt   4140
gtaaatcacc cagtcataac aaggtcgcag tgcatggtgt tgcacaatat cttttagaag   4200
```

```
taggctgatt gccacagata agcccttggt gtaggtgttt acaaaccggt tgagctggga   4260
tgggtgcatt cggggtgaaa ttatgtgcat tttggattgg atttttaagt tggcaatatt   4320
gccgccaaga tcccgtcttg ggttcatgtt atgaaggacc accaagacgg tgtatccggt   4380
acatttagga aatttatcgt gcagcttgga tggaaaagcg tggaaaaatt tggagacacc   4440
cttgtgtcct ccaagatttt ccatgcactc atccatgata atagcaatgg ggccgtgggc   4500
agcggcgcgg gcaaacacgt tccgtgggtc tgacacatca tagttatgtt cctgagttaa   4560
atcatcataa gccattttaa tgaatttggg gcggagagta ccagattggg gtatgaatgt   4620
tccttcgggc cccggagcat agttcccctc acagatttgc atttcccaag ctttcagttc   4680
cgagggtgga atcatgtcca cctggggggc tatgaaaaac accgtttctg gggcgggggt   4740
gattaattgt gatgatagca aatttctgag caattgagat ttgccacatc cggtggggcc   4800
ataaatgatt ccgattacgg gttgcaggtg gtagtttagg gaacggcaac tgccgtcttc   4860
tcgaagcaag gggccacct cgttcatcat ttcccttaca tgcatatttt cccgcaccaa   4920
atccattagg aggcgctctc ctcctagtga tagaagttct tgtagtgagg aaaagttttt   4980
cagcggtttc agaccgtcag ccatgggcat tttggagaga gtttgctgca aaagttctag   5040
tctgttccac agttcagtga tgtgttctat ggcatctcga tccagcagac ctcctcgttt   5100
cgcgggtttg gacggctcct ggaatagggt atgagacgat gggcgtccag cgctgccagg   5160
gttcggtcct tccagggtct cagtgttcga gtcagggttg tttccgtcac agtgaagggg   5220
tgtgcgcctg cttgggcgct tgccagggtg cgcttcagac tcatcctgct ggtcgaaaac   5280
ttctgtcgct tggcgccctg tatgtcggcc aagtagcagt ttaccatgag ttcgtagttg   5340
agcgcctcgg ctgcgtggcc tttggcgcgg agcttacctt tggaagtttt cttgcatacc   5400
gggcagtata ggcatttcag cgcatacaac ttgggcgcaa ggaaaacgga ttctggggag   5460
tatgcatctg cgccgcagga ggcgcaaaca gtttcacatt ccaccagcca ggttaaatcc   5520
ggttcattgg ggtcaaaaac aagttttccg ccatattttt tgatgcgttt cttacctttg   5580
gtctccatga gttcgtgtcc tcgttgagtg acaaacaggc tgtccgtgtc cccgtagact   5640
gattttacag gcctcttctc cagtggagtg cctcggtctt cttcgtacag gaactctgac   5700
cactctgata caaaggcgcg cgtccaggcc agcacaaagg aggctatgtg ggaggggtag   5760
cgatcgttgt caaccagggg gtccaccttt tccaaagtat gcaaacacat gtcaccctct   5820
tcaacatcca ggaatgtgat tggcttgtag gtgtatttca cgtgacctgg ggtccccgct   5880
gggggggtat aaaagggggc ggttctttgc tcttcctcac tgtcttccgg atcgctgtcc   5940
aggaacgtca gctgttgggg taggtattcc ctctcgaagg cgggcatgac ctctgcactc   6000
aggttgtcag tttctaagaa cgaggaggat ttgatattga cagtgccggt tgagatgcct   6060
ttcatgaggt tttcgtccat ctggtcagaa aacacaattt ttttattgtc aagtttggtg   6120
gcaaatgatc catacagggc gttggataaa agtttggcaa tggatcgcat ggtttggttc   6180
ttttccttgt ccgcgcgctc tttggcggcg atgttgagtt ggacatactc gcgtgccagg   6240
cacttccatt cggggaagat agttgttaat tcatctggca cgattctcac ttgccaccct   6300
cgattatgca aggtaattaa atccacactg gtggccacct cgcctcgaag ggggttcattg   6360
gtccaacaga gcctacctcc tttcctagaa cagaaagggg gaagtgggtc tagcataagt   6420
tcatcgggag ggtctgcatc catggtaaag attcccggaa gtaaatcctt atcaaaatag   6480
ctgatgggag tggggtcatc taaggccatt tgccattctc gagctgccag tgcgcgctca   6540
tatgggttaa ggggactgcc ccatggcatg ggatgggtga gtgcagaggc atacatgcca   6600
```

-continued cagatgtcat agacgtagat gggatcctca aagatgccta tgtaggttgg atagcatcgc 6660
ccccctctga tacttgctcg cacatagtca tatagttcat gtgatggcgc tagcagcccc 6720
ggacccaagt tggtgcgatt gggtttttct gttctgtaga cgatctggcg aaagatggcg 6780
tgagaattgg aagagatggt gggtctttga aaaatgttga aatgggcatg aggtagacct 6840
acagagtctc tgacaaagtg ggcataagat tcttgaagct tggttaccag ttcggcggtg 6900
acaagtacgt ctagggcgca gtagtcaagt gtttcttgaa tgatgtcata acctggttgg 6960
tttttctttt cccacagttc gcggttgaga aggtattctt cgcgatcctt ccagtactct 7020
tctagcggaa acccgtcttt gtctgcacgg taagatccta gcatgtagaa ctgattaact 7080
gccttgtaag ggcagcagcc cttctctacg ggtagagagt atgcttgagc agcttttcgt 7140
agcgaagcgt gagtaagggc aaaggtgtct ctgaccatga ctttgaggaa ttggtatttg 7200
aagtcgatgt cgtcacaggc tccctgttcc cagagttgga agtctacccg tttcttgtag 7260
gcggggttgg gcaaagcgaa agtaacatca ttgaagagaa tcttgccggc cctgggcatg 7320
aaattgcgag tgatgcgaaa aggctgtggt acttccgctc ggttattgat aacctgggca 7380
gctaggacga tctcgtcgaa accgttgatg ttgtgtccta cgatgtataa ttctatgaaa 7440
cgcggcgtgc ctctgacgtg aggtagctta ctgagctcat caaaggttag gtctgtgggg 7500
tcagataagg cgtagtgttc gagagcccat tcgtgcaggt gaggattcgc tttaaggaag 7560
gaggaccaga ggtccactgc cagtgctgtt tgtaactggt cccggtactg acgaaaatgc 7620
cgtccgactg ccatttttc tggggtgacg caatagaagg tttgggggtc ctgccgccag 7680
cgatcccact tgagttttat ggcgaggtca taggcgatgt tgacgagccg ctggtctcca 7740
gagagtttca tgaccagcat gaaggggatt agctgcttgc caaaggaccc catccaggtg 7800
taggtttcca catcgtaggt gagaaagagc ctttctgtgc gaggatgaga gccaatcggg 7860
aagaactgga tctcctgcca ccagttggag gaatggctgt tgatgtgatg gaagtagaac 7920
tccctgcgac gcgccgagca ttcatgcttg tgcttgtaca gacggccgca gtagtcgcag 7980
cgttgcacgg gttgtatctc gtgaatgagt tgtacctggc ttcccttgac gagaaatttc 8040
agtgggaagc cgaggcctgg cgattgtatc tcgtgcttta ctatgttgtc tgcatcggcc 8100
tgttcatctt ctgtctcgat ggtggtcatg ctgacgagcc ctcgcgggag gcaagtccag 8160
acctcggcgc ggcaggggcg gagctcgagg acgagagcgc gcaggctgga gctgtccagg 8220
gtcctgagac gctgcggact caggttagta ggcagtgtca ggagattaac ttgcatgatc 8280
ttttggaggg cgtgcgggag gttcagatag tacttgatct caacgggtcc gttggtggag 8340
atgtcgatgg cttgcagggt tccgtgtccc ttgggcgcta ccaccgtgcc cttgtttttc 8400
attttggacg gcggtggctc tgttgcttct tgcatgttta gaagcggtgt cgagggcgcg 8460
caccgggcgg caggggcggc tcgggacccg gcggcatggc tggcagtggt acgtcggcgc 8520
cgcgcgcggg taggttctgg tactgcgccc tgagaagact cgcatgcgcg acgacgcggc 8580
ggttgacatc ctggatctga cgcctctggg tgaaagctac cggccccgtg agcttgaacc 8640
tgaaagagag ttcaacagaa tcaatctcgg tatcgttgac ggcggcttgc ctaaggattt 8700
cttgcacgtc accagagttg tcctggtagg cgatctccgc catgaactgc tcgatctctt 8760
cctcttgaag atctccgcgg cccgctctct cgacggtggc cgcgaggtcg ttggagatgc 8820
gcccaatgag ttgagagaat gcattcatgc ccgcctcgtt ccagacgcgg ctgtagacca 8880
cggcccccac gggatctctc gcgcgcatga ccacctgggc gaggttgagc tccacgtggc 8940
gggtgaagac cgcatagttg cataggcgct ggaaaaggta gttgagtgtg gtggcgatgt 9000

```
gctcggtgac gaagaaatac atgatccatc gtctcagcgg catctcgctg acatcgccca   9060
gagcttccaa gcgctccatg gcctcgtaga agtccacggc aaaattaaaa aactgggagt   9120
ttcgcgcgga cacggtcaac tcctcttcca gaagacggat aagttcggcg atggtggtgc   9180
gcacctcgcg ctcgaaagcc cctgggattt cttcctcaat ctcttcttct tccactaaca   9240
tctcttcctc ttcaggtggg gctgcaggag gagggggaac gcggcgacgc cggcggcgca   9300
cgggcagacg gtcgatgaat ctttcaatga cctctccgcg gcggcggcgc atggtttcag   9360
tgacggcgcg gccgttctcg cgcggtcgca gagtaaaaac accgccgcgc atctccttaa   9420
agtggtgact gggaggttct ccgtttggga gggagagggc gctgattata cattttatta   9480
attggcccgt agggactgca cgcagagatc tgatcgtgtc aagatccacg ggatctgaaa   9540
acctttcgac gaaagcgtct aaccagtcac agtcacaagg taggctgagt acggcttctt   9600
gtgggcgggg gtggttatgt gttcggtctg ggtcttctgt ttcttcttca tctcgggaag   9660
gtgagacgat gctgctggtg atgaaattaa agtaggcagt tctaagacgg cggatggtgg   9720
cgaggagcac caggtctttg ggtccggctt gctggatacg caggcgattg gccattcccc   9780
aagcattatc ctgacatcta gcaagatctt tgtagtagtc ttgcatgagc cgttctacgg   9840
gcacttcttc ctcacccgtt ctgccatgca tacgtgtgag tccaaatccg cgcattggtt   9900
gtaccagtgc caagtcagct acgactcttt cggcgaggat ggcttgctgt acttgggtaa   9960
gggtggcttg aaagtcatca aaatccacaa agcggtggta agctcctgta ttaatggtgt  10020
aagcacagtt ggccatgact gaccagttaa ctgtctggtg accagggcgc acgagctcgg  10080
tgtatttaag gcgcgaatag gcgcgggtgt caaagatgta atcgttgcag gtgcgcacca  10140
gatactggta ccctataaga aaatgcggcg gtggttggcg gtagagaggc catcgttctg  10200
tagctggagc gccaggggcg aggtcttcca acataaggcg gtgatagccg tagatgtacc  10260
tggacatcca ggtgattcct gcggcggtag tagaagcccg aggaaactcg cgtacgcggt  10320
tccaaatgtt gcgtagcggc atgaagtagt tcattgtagg cacggtttga ccagtgaggc  10380
gcgcgcagtc attgatgctc tatagacacg gagaaaatga aagcgttcag cgactcgact  10440
ccgtagcctg gaggaacgtg aacgggttgg gtcgcggtgt accccggttc gagacttgta  10500
ctcgagccgg ccggagccgc ggctaacgtg gtattggcac tcccgtctcg acccagccta  10560
caaaaatcca ggatacggaa tcgagtcgtt ttgctggttt ccgaatggca gggaagtgag  10620
tcctattttt tttttttgcc gctcagatgc atcccgtgct gcgacagatg cgcccccaac  10680
aacagccccc ctcgcagcag cagcagcagc aatcacaaaa ggctgtccct gcaactactg  10740
caactgccgc cgtgagcggt gcgggacagc ccgcctatga tctggacttg gaagagggcg  10800
aaggactggc acgtctaggt gcgccttcac ccgagcggca tccgcgagtt caactgaaaa  10860
aagattctcg cgaggcgtat gtgccccaac agaacctatt tagagacaga agcggcgagg  10920
agccggagga gatgcgagct tcccgcttta acgcgggtcg tgagctgcgt cacggtttgg  10980
accgaagacg agtgttgcgg gacgaggatt tcgaagttga tgaaatgaca gggatcagtc  11040
ctgccagggc acacgtggct gcagccaacc ttgtatcggc ttacgagcag acagtaaagg  11100
aagagcgtaa cttccaaaag tcttttaata atcatgtgcg aaccctgatt gcccgcgaag  11160
aagttaccct tggtttgatg catttgtggg atttgatgga agctatcatt cagaacccta  11220
ctagcaaacc tctgaccgcc cagctgtttc tggtggtgca acacagcaga gacaatgagg  11280
ctttcagaga ggcgctgctg aacatcaccg aacccgaggg gagatggttg tatgatctta  11340
tcaacattct acagagtatc atagtgcagg agcggagcct gggcctggcc gagaaggtgg  11400
```

```
ctgccatcaa ttactcggtt ttgagcttgg gaaaatatta cgctcgcaaa atctacaaga  11460
ctccatacgt tcccatagac aaggaggtga agatagatgg gttctacatg cgcatgacgc  11520
tcaaggtctt gaccctgagc gatgatcttg ggtgtatcg caatgacaga atgcatcgcg  11580
cggttagcgc cagcaggagg cgcgagttaa gcgacaggga actgatgcac agtttgcaaa  11640
gagctctgac tggagctgga accgagggtg agaattactt cgacatggga gctgacttgc  11700
agtggcagcc tagtcgcagg gctctgagcg ccgcgacggc aggatgtgag cttccttaca  11760
tagaagaggc ggatgaaggc gaggaggaag agggcgagta cttggaagac tgatggcaca  11820
acccgtgttt tttgctagat ggaacagcaa gcaccggatc ccgcaatgcg ggcggcgctg  11880
cagagccagc cgtccggcat taactcctcg gacgattgga cccaggccat gcaacgtatc  11940
atggcgttga cgactcgcaa ccccgaagcc tttagacagc aaccccaggc caaccgtcta  12000
tcggccatca tggaagctgt agtgccttcc cgctctaatc ccactcatga gaaggtcctg  12060
gccatcgtga acgcgttggt ggagaacaaa gctattcgtc cagatgaggc cggactggta  12120
tacaacgctc tcttagaacg cgtggctcgc tacaacagta gcaatgtgca aaccaatttg  12180
gaccgtatga taacagatgt acgcgaagcc gtgtctcagc gcgaaaggtt ccagcgtgat  12240
gccaacctgg gttcgctggt ggcgttaaat gctttcttga gtactcagcc tgctaatgtg  12300
ccgcgtggtc aacaggatta tactaacttt ttaagtgctt tgagactgat ggtatcagaa  12360
gtacctcaga gcgaagtgta tcagtccggt cctgattact tctttcagac tagcagacag  12420
ggcttgcaga cggtaaatct gagccaagct tttaaaaacc tttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgccccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
```

```
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tgtcgcagcg gcgactattg ccgacatggc ccaatcgcga agaggcaatg tatactgggt  15900
gcgtgacgct gccaccggtc aacgtgtacc cgtgcgcacc cgtcccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
```

```
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg ggggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
```

```
attctggtac ggcttacaac tccctggctc ctaaaggcgc tccaaataca tctcagtgga  18660
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg ggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
```

```
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
```

```
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
acacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
```

```
gctgcggaga caagcaacag cgctaccatc tccgctccga gtcgaggaac ccggcggcgt  25860
cccagcagta gatgggacga gaccggacgc ttcccgaacc caaccagcgc ttccaagacc  25920
ggtaagaagg atcggcaggg atacaagtcc tggcgggggc ataagaatgc catcatctcc  25980
tgcttgcatg agtgcggggg caacatatcc ttcacgcggc gctacttgct attccaccat  26040
ggggtgaact ttccgcgcaa tgttttgcat tactaccgtc acctccacag cccctactat  26100
agccagcaaa tcccggcagt ctcgacagat aaagacagcg gcggcgacct ccaacagaaa  26160
accagcagcg gcagttagaa aatacacaac aagtgcagca acaggaggat taaagattac  26220
agccaacgag ccagcgcaaa cccgagagtt aagaaatcgg atctttccaa ccctgtatgc  26280
catcttccag cagagtcggg gtcaagagca ggaactgaaa ataaaaaacc gatctctgcg  26340
ttcgctcacc agaagttgtt tgtatcacaa gagcgaagat caacttcagc gcactctcga  26400
ggacgccgag gctctcttca acaagtactg cgcgctgact cttaaagagt aggcagcgac  26460
cgcgcttatt caaaaaaggc gggaattaca tcatcctcga catgagtaaa gaaattccca  26520
cgccttacat gtggagttat caaccccaaa tgggattggc ggcaggcgcc tcccaggact  26580
actccacccg catgaattgg ctcagcgccg ggccttctat gatttctcga gttaatgata  26640
tacgcgccta ccgaaaccaa atacttttgg aacagtcagc tcttaccacc acgccccgcc  26700
aacaccttaa tcccagaaat tggcccgccg ccctagtgta ccaggaaagt cccgctccca  26760
ccactgtatt acttcctcga gacgcccagg ccgaagtcca aatgactaat gcaggtgcgc  26820
agttagctgg cggctccacc ctatgtcgtc acaggcctcg gcataatata aaacgcctga  26880
tgatcagagg ccgaggtatc cagctcaacg acgagtcggt gagctctccg cttggtctac  26940
gaccagacgg aatctttcag attgccggct gcgggagatc ttccttcacc cctcgtcagg  27000
ctgttctgac tttggaaagt tcgtcttcgc aaccccgctc gggcggaatc gggaccgttc  27060
aatttgtgga ggagtttact ccctctgtct acttcaaccc cttctccgga tctcctgggc  27120
attacccgga cgagttcata ccgaacttcg acgcgattag cgagtcagtg gacggctacg  27180
attgatgtct ggtgacgcgg ctgagctatc tcggctgcga catctagacc actgccgccg  27240
ctttcgctgc tttgcccggg aactcattga gttcatctac ttcgaactcc ccaaggatca  27300
ccctcaaggt ccggcccacg gagtgcggat ttctatcgaa ggcaaaatag actctcgcct  27360
gcaacgaatt ttctcccagc ggcccgtgct gatcgagcga gaccagggaa acaccacggt  27420
ttccatctac tgcatttgta atcaccccgg attgcatgaa agcctttgct gtcttatgtg  27480
tactgagttt aataaaaact gaattaagac tctcctacgg actgccgctt cttcaacccg  27540
gattttacaa ccagaagaac gaaacttttc ctgtcgtcca ggactctgtt aacttcacct  27600
ttcctactca caaactagaa gctcaacgac tacaccgctt ttccagaagc attttcccta  27660
ctaatactac tttcaaaacc ggaggtgagc tccaaggtct tcctacagaa aacccttggg  27720
tggaagcggg ccttgtagtg ctaggaattc ttgcgggtgg gcttgtgatt attctttgct  27780
acctatacac accttgcttc actttcttag tggtgttgtg gtattggttt aaaaaatggg  27840
gcccatacta gtcttgcttg ttttactttc gcttttggaa ccgggttctg ccaattacga  27900
tccatgtcta gacttcgacc cagaaaactg cacacttact tttgcacccg acacaagccg  27960
catctgtgga gttcatcgcc tctcttacga acttggcccc caacgacaaa aatttacctg  28020
catggtggga atcaacccca tagttatcac ccagcaaagt ggagatacta agggttgcat  28080
tcactgctcc tgcgattcca tcgagtgcac ctacaccctg ctgaagaccc tatgcggcct  28140
aagagacctg ctaccaatga attaaaaaat gattaataaa aaatcactta cttgaaatca  28200
```

gcaataaggt ctctgttgaa attttctccc agcagcacct cacttccctc ttcccaactc 28260
tggtattcta aaccccgttc agcggcatac tttctccata ctttaaaggg gatgtcaaat 28320
tttagctcct ctcctgtacc cacaatcttc atgtctttct tcccagatga ccaagagagt 28380
ccggctcagt gactccttca accctgtcta cccctatgaa gatgaaagca cctcccaaca 28440
cccctttata aacccagggt ttatttcccc aaatggcttc acacaaagcc caaacggagt 28500
tcttacttta aaatgtttaa ccccactaac aaccacaggc ggatctctac agctaaaagt 28560
gggaggggga cttacagtgg atgacaccaa cggttttttg aaagaaaaca taagtgccac 28620
cacaccactc gttaagactg gtcactctat aggtttacca ctaggagccg gattgggaac 28680
gaatgaaaat aaactttgta tcaaattagg acaaggactt acattcaatt caaacaacat 28740
ttgcattgat gacaatatta acaccttatg gacaggagtc aaccccaccg aagccaactg 28800
tcaaatcatg aactccagtg aatctaatga ttgcaaatta attctaacac tagttaaaac 28860
tggagcacta gtcactgcat ttgtttatgt tataggagta tctaacaatt ttaatatgct 28920
aactacacac agaaatataa attttactgc agagctgttt ttcgattcta ctggtaattt 28980
actaactaga ctctcatccc tcaaaactcc acttaatcat aaatcaggac aaaacatggc 29040
tactggtgcc attactaatg ctaaaggttt catgcccagc acgactgcct atcctttcaa 29100
tgataattct agagaaaaag aaaactacat ttacggaact tgttactaca cagctagtga 29160
tcgcactgct ttttcccattg acatatctgt catgcttaac cgaagagcaa taaatgacga 29220
gacatcatat tgtattcgta taacttggtc ctggaacaca ggagatgccc cagaggtgca 29280
aacctctgct acaaccctag tcacctcccc atttaccttt tactacatca gagaagacga 29340
ctgacaaata aagtttaact tgtttatttg aaaatcaatt cacaaaatcc gagtagttat 29400
tttgcctccc ccttcccatt taacagaata caccaatctc tccccacgca cagctttaaa 29460
catttggata ccattagata tagacatggt tttagattcc acattccaaa cagtttcaga 29520
gcgagccaat ctggggtcag tgatagataa aaatccatcg ggatagtctt ttaaagcgct 29580
ttcacagtcc aactgctgcg gatgcgactc cggagtctgg atcacggtca tctggaagaa 29640
gaacgatggg aatcataatc cgaaaacggt atcggacgat tgtgtctcat caaacccaca 29700
agcagccgct gtctgcgtcg ctccgtgcga ctgctgttta tgggatcagg gtccacagtg 29760
tcctgaagca tgattttaat agcccttaac atcaactttc tggtgcgatg cgcgcagcaa 29820
cgcattctga tttcactcaa atctttgcag taggtacaac acattattac aatattgttt 29880
aataaaccat aattaaaagc gctccagcca aaactcatat ctgatataat cgcccctgca 29940
tgaccatcat accaaagttt aatataaatt aaatgacgtt ccctcaaaaa cacactaccc 30000
acatacatga tctcttttgg catgtgcata ttaacaatct gtctgtacca tggacaacgt 30060
tggttaatca tgcaacccaa tataaccttc cggaaccaca ctgccaacac cgctccccca 30120
gccatgcatt gaagtgaacc ctgctgatta caatgacaat gaagaaccca attctctcga 30180
ccgtgaatca cttgagaatg aaaaatatct atagtggcac aacatagaca taaatgcatg 30240
catcttctca taatttttaa ctcctcagga tttagaaaca tatcccaggg aataggaagc 30300
tcttgcagaa cagtaaagct ggcagaacaa ggaagaccac gaacacaact tacactatgc 30360
atagtcatag tatcacaatc tggcaacagc gggtggtctt cagtcataga agctcgggtt 30420
tcattttcct cacaacgtgg taactgggct ctggtgtaag ggtgatgtct ggcgcatgat 30480
gtcgagcgtg cgcgcaacct tgtcataatg gagttgcttc ctgacattct cgtattttgt 30540
atagcaaaac gcggccctgg cagaacacac tcttcttcgc cttctatcct gccgcttagc 30600

```
gtgttccgtg tgatagttca agtacaacca cactcttaag ttggtcaaaa gaatgctggc  30660

ttcagttgta atcaaaactc catcgcatct aatcgttctg aggaaatcat ccaagcaatg  30720

caactggatt gtgtttcaag caggagagga gagggaagag acggaagaac catgttaatt  30780

tttattccaa acgatctcgc agtacttcaa attgtagatc gcgcagatgg catctctcgc  30840

ccccactgtg ttggtgaaaa agcacagcta gatcaaaaga aatgcgattt tcaaggtgct  30900

caacggtggc ttccagcaaa gcctccacgc gcacatccaa gaacaaaaga ataccaaaag  30960

aaggagcatt ttctaactcc tcaatcatca tattacattc ctgcaccatt cccagataat  31020

tttcagcttt ccagccttga attattcgtg tcagttcttg tggtaaatcc aatccacaca  31080

ttacaaacag gtcccggagg gcgccctcca ccaccattct taaacacacc ctcataatga  31140

caaaatatct tgctcctgtg tcacctgtag cgaattgaga atggcaacat caattgacat  31200

gcccttggct ctaagttctt ctttaagttc tagttgtaaa aactctctca tattatcacc  31260

aaactgctta gccagaagcc ccccgggaac aagagcaggg gacgctacag tgcagtacaa  31320

gcgcagacct ccccaattgg ctccagcaaa aacaagattg gaataagcat attgggaacc  31380

gccagtaata tcatcgaagt tgctggaaat ataatcaggc agagtttctt gtaaaaattg  31440

aataaaagaa aaatttgcca aaaaaacatt caaaacctct gggatgcaaa tgcaataggt  31500

taccgcgctg cgctccaaca ttgttagttt tgaattagtc tgcaaaaata aaaaaaaaaa  31560

caagcgtcat atcatagtag cctgacgaac agatggataa atcagtcttt ccatcacaag  31620

acaagccaca gggtctccag ctcgaccctc gtaaaacctg tcatcatgat taaacaacag  31680

caccgaaagt tcctcgcggt gaccagcatg aataattctt gatgaagcat acaatccaga  31740

catgttagca tcagttaacg agaaaaaaca gccaacatag cctttgggta taattatgct  31800

taatcgtaag tatagcaaag ccacccctcg cggatacaaa gtaaaaggca caggagaata  31860

aaaaatataa ttatttctct gctgctgttc aggcaacgtc gcccccggtc cctctaaata  31920

cacatacaaa gcctcatcag ccatggctta ccagacaaag tacagcgggc acacaaagca  31980

caagctctaa agtgactctc caacctctcc acaatatata tatacacaag ccctaaactg  32040

acgtaatggg agtaaagtgt aaaaaatccc gccaaaccca acacacaccc cgaaactgcg  32100

tcaccaggga aaagtacagt ttcacttccg caatcccaac aggcgtaact tcctctttct  32160

cacggtacgt gatatcccac taacttgcaa cgtcattttc ccacggtcgc accgcccctt  32220

ttagccgtta accccacagc caatcaccac acgatccaca ctttttaaaa tcacctcatt  32280

tacatattgg caccattcca tctataaggt atattatata gatag                 32325
```

<210> SEQ ID NO 2
<211> LENGTH: 34794
<212> TYPE: DNA
<213> ORGANISM: Adenovirus

<400> SEQUENCE: 2

```
ctatctatat aatatacctt atagatggaa tggtgccaat atgtaaatga ggtgatttta     60

aaaagtgtgg atcgtgtggt gattggctgt ggggttaacg gctaaaaggg gcggtgcgac    120

cgtgggaaaa tgacgttttg tgggggtgga gttttttttgc aagttgtcgc gggaaatgtg    180

acgcataaaa aggctttttt ctcacggaac tacttagttt tcccacggta tttaacagga    240

aatgaggtag ttttgaccgg atgcaagtga aaattgttga ttttcgcgcg aaaactgaat    300

gaggaagtgt ttttctgaat aatgtggtat ttatggcagg gtggagtatt tgttcagggc    360

caggtagact ttgacccatt acgtggaggt ttcgattacc gtgtttttta cctgaatttc    420
```

-continued

```
cgcgtaccgt gtcaaagtct tctgttttta cgtaggtgtc agctgatcgc tagggtattt    480
atacctcagg gtttgtgtca agaggccact cttgagtgcc agcgagaaga gttttctcct    540
ctgcgccggc agtttaataa taaaaaaatg agagatttgc gatttctgcc tcaggaaata    600
atctctgctg agactggaaa tgaaatattg gagcttgtgg tgcacgccct gatgggagac    660
gatccggagc cacctgtgca gctttttgag cctcctacgc ttcaggaact gtatgattta    720
gaggtagagg gatcggagga ttctaatgag gaagctgtaa atggcttttt taccgattct    780
atgcttttag ctgctaatga agggttagaa ttagatccgc ctttggacac ttttgatact    840
ccaggggtaa ttgtggaaag cggtacaggt gtaagaaaat tacctgattt gagttccgtg    900
gactgtgatt tgcactgcta tgaagacggg tttcctccga gtgatgagga ggaccatgaa    960
aaggagcagt ccatgcagac tgcagcgggt gagggagtga aggctgccaa tgttggtttt   1020
cagttggatt gcccggagct tcctggacat ggctgtaagt cttgtgaatt tcacaggaaa   1080
aatactggag taaaggaact gttatgttcg ctttgttata tgagaacgca ctgccacttt   1140
atttacagta agtgtgttta agttaaaatt taaaggaata tgctgttttt cacatgtata   1200
ttgagtgtga gttttgtgct tcttattata ggtcctgtgt ctgatgctga tgaatcacca   1260
tctcctgatt ctactacctc acctcctgag attcaagcac ctgttcctgt ggacgtgcgc   1320
aagcccattc ctgtgaagct taagcctggg aaacgtccag cagtggaaaa acttgaggac   1380
ttgttacagg gtggggacgg acctttggac ttgagtacac ggaaacgtcc aagacaataa   1440
gtgttccata tccgtgttta cttaaggtga cgtcaatatt tgtgtgacag tgcaatgtaa   1500
taaaaatatg ttaactgttc actggttttt attgcttttt gggcggggac tcaggtatat   1560
aagtagaagc agacctgtgt ggttagctca taggagctgg ctttcatcca tggaggtttg   1620
ggccattttg gaagacctta ggaagactag gcaactgtta gagaacgctt cggacggagt   1680
ctccggtttt tggagattct ggttcgctag tgaattagct agggtagttt ttaggataaa   1740
acaggactat aaacaagaat ttgaaaagtt gttggtagat tgcccaggac tttttgaagc   1800
tcttaatttg ggccatcagg ttcactttaa agaaaaagtt ttatcagttt tagacttttc   1860
aaccccaggt agaactgctg ctgctgtggc ttttcttact tttatattag ataaatggat   1920
cccgcagact catttcagca ggggatacgt tttggatttc atagccacag cattgtggag   1980
aacatggaag gttcgcaaga tgaggacaat cttaggttac tggccagtgc agcctttggg   2040
tgtagcggga atcctgaggc atccaccggt catgccagcg gttctggagg aggaacagca   2100
agaggacaac ccgagagccg gcctggaccc tccagtggag gaggcggagt agctgacttg   2160
tctcctgaac tgcaacgggt gcttactgga tctacgtcca ctggacggga taggggcgtt   2220
aagagggaga gggcatctag tggtactgat gctagatctg agttggcttt aagtttaatg   2280
agtcgcagac gtcctgaaac catttggtgg catgaggttc agaaagaggg aagggatgaa   2340
gtttctgtat tgcaggagaa atattcactg gaacaggtga aaacatgttg gttggagcct   2400
gaggatgatt gggaggtggc cattaaaaat tatgccaaga tagctttgag gcctgataaa   2460
cagtataaga ttactagacg gattaatatc cggaatgctt gttacatatc tggaaatggg   2520
gctgaggtgg taatagatac tcaagacaag gcagttatta gatgctgcat gatggatatg   2580
tggcctgggg tagtcggtat ggaagcagta acttttgtaa atgttaagtt taggggagat   2640
ggttataatg gaatagtgtt tatggccaat accaaactta tattgcatgg ttgtagcttt   2700
tttggtttca acaatacctg tgtagatgcc tggggacagg ttagtgtacg ggatgtagt    2760
ttctatgcgt gttggattgc cacagctggc agaaccaaga gtcaattgtc tctgaagaaa   2820
```

```
tgcatatttc aaagatgtaa cctgggcatt ctgaatgaag gcgaagcaag ggtccgccac   2880
tgcgcttcta cagatactgg atgttttatt ttgattaagg gaaatgccag cgtaaagcat   2940
aacatgattt gcggtgcttc cgatgagagg ccttatcaaa tgctcacttg tgctggtggg   3000
cattgtaata tgctggctac tgtgcatatt gtttcccatc aacgcaaaaa atggcctgtt   3060
tttgatcaca atgtgatgac gaagtgtacc atgcatgcag gtgggcgtag aggaatgttt   3120
atgccttacc agtgtaacat gaatcatgtg aaagtgttgt tggaaccaga tgccttttcc   3180
agaatgagcc taacaggaat ttttgacatg aacatgcaaa tctggaagat cctgaggtat   3240
gatgatacga gatcgagggt acgcgcatgc gaatgcggag gcaagcatgc caggttccag   3300
ccggtgtgtg tagatgtgac tgaagatctc agaccggatc atttggttat tgcccgcact   3360
ggagcagagt tcggatccag tggagaagaa actgactaag gtgagtattg ggaaaacttt   3420
ggggtgggat tttcagatgg acagattgag taaaaatttg tttttctgt cttgcagctg    3480
tcatgagtgg aaacgcttct tttaaggggg gagtcttcag cccttatctg acagggcgtc   3540
tcccatcctg ggcaggagtt cgtcagaatg ttatgggatc tactgtggat ggaagacccg   3600
tccaacccgc caattcttca acgctgacct atgctacttt aagttcttca cctttggacg   3660
cagctgcagc tgccgccgcc gcttctgttg ccgctaacac tgtgcttgga atgggttact   3720
atggaagcat catggctaat tccacttcct ctaataaccc ttctaccctg actcaggaca   3780
agttacttgt ccttttggcc cagctggagg ctttgaccca acgtctgggt gaactttctc   3840
agcaggtggt cgagttgcga gtacaaactg agtctgctgt cggcacggca aagtctaaat   3900
aaaaaaatcc cagaatcaat gaataaataa acaagcttgt tgttgattta aaatcaagtg   3960
tttttatttc atttttcgcg cacggtatgc cctagaccac cgatctctat cattgagaac   4020
tcggtggatt ttttccagga tcctatagag gtgggattga atgtttagat acatgggcat   4080
taggccgtct ttggggtgga gatagctcca ttgaagggat tcatgctccg gggtagtgtt   4140
gtaaatcacc cagtcataac aaggtcgcag tgcatggtgt tgcacaatat cttttagaag   4200
taggctgatt gccacagata agcccttggt gtaggtgttt acaaaccggt tgagctggga   4260
tgggtgcatt cggggtgaaa ttatgtgcat tttggattgg atttttaagt tggcaatatt   4320
gccgccaaga tcccgtcttg ggttcatgtt atgaaggacc accaagacgg tgtatccggt   4380
acatttagga aatttatcgt gcagcttgga tggaaaagcg tggaaaaatt tggagacacc   4440
cttgtgtcct ccaagatttt ccatgcactc atccatgata atagcaatgg ggccgtgggc   4500
agcggcgcgg gcaaacacgt tccgtgggtc tgacacatca tagttatgtt cctgagttaa   4560
atcatcataa gccattttaa tgaatttggg gcggagagta ccagattggg gtatgaatgt   4620
tccttcgggc cccggagcat agttcccctc acagatttgc atttcccaag ctttcagttc   4680
cgagggtgga atcatgtcca cctgggggc  tatgaaaaac accgtttctg gggcgggggt   4740
gattaattgt gatgatagca aatttctgag caattgagat ttgccacatc cggtggggcc   4800
ataaatgatt ccgattacgg gttgcaggtg gtagtttagg gaacggcaac tgccgtcttc   4860
tcgaagcaag gggccacct  cgttcatcat ttcccttaca tgcatatttt cccgcaccaa   4920
atccattagg aggcgctctc ctcctagtga tagaagttct tgtagtgagg aaaagttttt   4980
cagcggtttc agaccgtcag ccatgggcat tttggagaga gtttgctgca aaagttctag   5040
tctgttccac agttcagtga tgtgttctat ggcatctcga tccagcagac ctcctcgttt   5100
cgcgggtttg gacggctcct ggaatagggt atgagacgat gggcgtccag cgctgccagg   5160
gttcggtcct tccagggtct cagtgttcga gtcagggttg tttccgtcac agtgaagggg   5220
```

-continued

```
tgtgcgcctg cttgggcgct tgccagggtg cgcttcagac tcatcctgct ggtcgaaaac   5280
ttctgtcgct tggcgccctg tatgtcggcc aagtagcagt ttaccatgag ttcgtagttg   5340
agcgcctcgg ctgcgtggcc tttggcgcgg agcttacctt tggaagtttt cttgcatacc   5400
gggcagtata ggcatttcag cgcatacaac ttgggcgcaa ggaaaacgga ttctggggag   5460
tatgcatctg cgccgcagga ggcgcaaaca gtttcacatt ccaccagcca ggttaaatcc   5520
ggttcattgg ggtcaaaaac aagttttccg ccatattttt tgatgcgttt cttacctttg   5580
gtctccatga gttcgtgtcc tcgttgagtg acaaacaggc tgtccgtgtc cccgtagact   5640
gattttacag gcctcttctc cagtggagtg cctcggtctt cttcgtacag gaactctgac   5700
cactctgata caaaggcgcg cgtccaggcc agcacaaagg aggctatgtg ggaggggtag   5760
cgatcgttgt caaccagggg gtccaccttt tccaaagtat gcaaacacat gtcaccctct   5820
tcaacatcca ggaatgtgat tggcttgtag gtgtatttca cgtgacctgg ggtccccgct   5880
gggggggtat aaaagggggc ggttctttgc tcttcctcac tgtcttccgg atcgctgtcc   5940
aggaacgtca gctgttgggg taggtattcc ctctcgaagg cgggcatgac ctctgcactc   6000
aggttgtcag tttctaagaa cgaggaggat ttgatattga cagtgccggt tgagatgcct   6060
ttcatgaggt tttcgtccat ttggtcagaa aacacaattt ttttattgtc aagtttggtg   6120
gcaaatgatc catacagggc gttggataaa agtttggcaa tggatcgcat ggtttggttc   6180
ttttccttgt ccgcgcgctc tttggcggcg atgttgagtt ggacatactc gcgtgccagg   6240
cacttccatt cggggaagat agttgttaat tcatctggca cgattctcac ttgccaccct   6300
cgattatgca aggtaattaa atccacactg gtggccacct cgcctcgaag ggggttcattg   6360
gtccaacaga gcctacctcc tttcctagaa cagaaagggg gaagtgggtc tagcataagt   6420
tcatcgggag ggtctgcatc catggtaaag attcccggaa gtaaatcctt atcaaaatag   6480
ctgatgggag tggggtcatc taaggccatt tgccattctc gagctgccag tgcgcgctca   6540
tatgggttaa ggggactgcc ccatggcatg ggatgggtga gtgcagaggc atacatgcca   6600
cagatgtcat agacgtagat gggatcctca aagatgccta tgtaggttgg atagcatcgc   6660
cccccctctga tacttgctcg cacatagtca tatagttcat gtgatggcgc tagcagcccc   6720
ggacccaagt tggtgcgatt gggtttttct gttctgtaga cgatctggcg aaagatggcg   6780
tgagaattgg aagagatggt gggtctttga aaaatgttga aatgggcatg aggtagacct   6840
acagagtctc tgacaaagtg ggcataagat tcttgaagct tggttaccag ttcggcggtg   6900
acaagtacgt ctagggcgca gtagtcaagt gtttcttgaa tgatgtcata acctggttgg   6960
tttttctttt cccacagttc gcggttgaga aggtattctt cgcgatcctt ccagtactct   7020
tctagcggaa acccgtcttt gtctgcacgg taagatccta gcatgtagaa ctgattaact   7080
gccttgtaag ggcagcagcc cttctctacg ggtagagagt atgcttgagc agcttttcgt   7140
agcgaagcgt gagtaagggc aaaggtgtct ctgaccatga ctttgagaaa ttggtatttg   7200
aagtcgatgt cgtcacaggc tccctgttcc cagagttgga agtctacccg tttcttgtag   7260
gcggggttgg gcaaagcgaa agtaacatca ttgaagagaa tcttaccggc tctgggcata   7320
aaattgcgag tgatgcgaaa aggctgtggt acttccgctc gattgttgat cacctgggca   7380
gctaggacga tctcgtcgaa accgttgatg ttgtgtccta cgatgtataa ttctatgaaa   7440
cgcggcgtgc ctctgacgtg aggtagctta ctgagctcat caaaggttag gtctgtgggg   7500
tcagataagg cgtagtgttc gagagcccat tcgtgcaggt gaggatttgc atgtaggaat   7560
gatgaccaaa gatctaccgc cagtgctgtt tgtaactggt cccgatactg acgaaaatgc   7620
```

```
cggccaattg ccatttttc tggagtgaca cagtagaagg ttctggggtc ttgttgccat   7680
cgatcccact tgagtttaat ggctagatcg tgggccatgt tgacgagacg ctcttctcct   7740
gagagtttca tgaccagcat gaaaggaact agttgtttgc caaaggatcc catccaggtg   7800
taagtttcca catcgtaggt caggaagagt ctttctgtgc gaggatgaga gccgatcggg   7860
aagaactgga tttcctgcca ccagttggag gattggctgt tgatgtgatg gaagtagaag   7920
tttctgcggc gcgccgagca ttcgtgtttg tgcttgtaca gacggccgca gtagtcgcag   7980
cgttgcacgg gttgtatctc gtgaatgagt tgtacctggc ttcccttgac gagaaatttc   8040
agtgggaagc cgaggcctgg cgattgtatc tcgtgctctt ctatattcgc tgtatcggcc   8100
tgttcatctt ctgtttcgat ggtggtcatg ctgacgagcc cccgcgggag gcaagtccag   8160
acctcggcgc gggagggggcg gagctgaagg acgagagcgc gcaggctgga gctgtccaga   8220
gtcctgagac gctgcggact caggttagta ggtagggaca gaagattaac ttgcatgatc   8280
ttttccaggg cgtgcgggag gttcagatgg tacttgattt ccacaggttc gtttgtagag   8340
acgtcaatgg cttgcagggt tccgtgtcct ttgggcgcca ctaccgtacc tttgtttttt   8400
cttttgatcg gtggtggctc tcttgcttct tgcatgctca gaagcggtga cggggacgcg   8460
cgccgggcgg cagcggttgt tccggacccg agggcatggc tggtagtggc acgtcggcgc   8520
cgcgcacggg caggttctgg tactgcgctc tgagaagact tgcgtgcgcc accacgcgtc   8580
gattgacgtc ttgtatctga cgtctctggg tgaaagctac cggccccgtg agcttgaacc   8640
tgaaagagag ttcaacagaa tcaatttcgg tatcgttaac ggcagcttgt ctcagtattt   8700
cttgtacgtc accagagttg tcctggtagg cgatctccgc catgaactgc tcgatttctt   8760
cctcctgaag atctccgcga cccgctcttt cgacggtggc cgcgaggtca ttggagatac   8820
ggcccatgag ttgggagaat gcattcatgc ccgcctcgtt ccagacgcgg ctgtaaacca   8880
cggccccctc ggagtctctt gcgcgcatca ccacctgagc gaggttaagc tccacgtgtc   8940
tggtgaagac cgcatagttg cataggcgct gaaaaaggta gttgagtgtg gtggcaatgt   9000
gttcggcgac gaagaaatac atgatccatc gtctcagcgg catttcgcta acatcgccca   9060
gagcttccaa gcgctccatg gcctcgtaga agtccacggc aaaattaaaa aactgggagt   9120
ttcgcgcgga cacggtcaat tcctcctcga gaagacggat gagttcggct atggtggccc   9180
gtacttcgcg ttcgaaggct cccgggatct cttcttcctc ttctatctct tcttccacta   9240
acatctcttc ttcgtcttca ggcgggggcg gagggggcac gcggcgacgt cgacggcgca   9300
cgggcaaacg gtcgatgaat cgttcaatga cctctccgcg gcggcggcgc atggtttcag   9360
tgacggcgcg gccgttctcg cgcggtcgca gagtaaaaac accgccgcgc atctccttaa   9420
agtggtgact gggaggttct ccgtttggga gggagagggc gctgattata catttttatta   9480
attggcccgt agggactgca cgcagagatc tgatcgtgtc aagatccacg ggatctgaaa   9540
acctttcgac gaaagcgtct aaccagtcac agtcacaagg taggctgagt acggcttctt   9600
gtgggcgggg gtggttatgt gttcggtctg ggtcttctgt ttcttcttca tctcgggaag   9660
gtgagacgat gctgctggtg atgaaattaa agtaggcagt tctaagacgg cggatggtgg   9720
cgaggagcac caggtctttg ggtccggctt gctggatacg caggcgattg gccattcccc   9780
aagcattatc ctgacatcta gcaagatctt tgtagtagtc ttgcatgagc cgttctacgg   9840
gcacttcttc ctcacccgtt ctgccatgca tacgtgtgag tccaaatccg cgcattggtt   9900
gtaccagtgc caagtcagct acgactcttt cggcgaggat ggcttgctgt acttgggtaa   9960
gggtggcttg aaagtcatca aaatccacaa agcggtggta agctcctgta ttaatggtgt  10020
```

```
aagcacagtt ggccatgact gaccagttaa ctgtctggtg accagggcgc acgagctcgg  10080
tgtatttaag gcgcgaatag gcgcgggtgt caaagatgta atcgttgcag gtgcgcacca  10140
gatactggta ccctataaga aaatgcggcg gtggttggcg gtagagaggc catcgttctg  10200
tagctggagc gccaggggcg aggtcttcca acataaggcg gtgatagccg tagatgtacc  10260
tggacatcca ggtgattcct gcggcggtag tagaagcccg aggaaactcg cgtacgcggt  10320
tccaaatgtt gcgtagcggc atgaagtagt tcattgtagg cacggtttga ccagtgaggc  10380
gcgcgcagtc attgatgctc tatagacacg gagaaaatga aagcgttcag cgactcgact  10440
ccgtagcctg gaggaacgtg aacgggttgg gtcgcggtgt accccggttc gagacttgta  10500
ctcgagccgg ccggagccgc ggctaacgtg gtattggcac tcccgtctcg acccagccta  10560
caaaaatcca ggatacggaa tcgagtcgtt ttgctggttt ccgaatggca gggaagtgag  10620
tcctattttt tttttttgcc gctcagatgc atcccgtgct gcgacagatg cgcccccaac  10680
aacagccccc ctcgcagcag cagcagcagc aatcacaaaa ggctgtccct gcaactactg  10740
caactgccgc cgtgagcggt gcgggacagc ccgcctatga tctggacttg gaagagggcg  10800
aaggactggc acgtctaggt gcgccttcac ccgagcggca tccgcgagtt caactgaaaa  10860
aagattctcg cgaggcgtat gtgccccaac agaacctatt tagagacaga agcggcgagg  10920
agccggagga gatgcgagct tcccgcttta acgcgggtcg tgagctgcgt cacggtttgg  10980
accgaagacg agtgttgcgg gacgaggatt tcgaagttga tgaaatgaca gggatcagtc  11040
ctgccagggc acacgtgtct gcagccaacc ttgtatcggc ttacgagcag acagtaaagg  11100
aagagcgtaa cttccaaaag tcttttaata atcatgtgcg aaccctgatt gcccgcgaag  11160
aagttaccct tggtttgatg catttgtggg atttgatgga agctatcatt cagaacccta  11220
ctagcaaacc tctgaccgcc cagctgtttc tggtggtgca acacagcaga gacaatgagg  11280
ctttcagaga ggcgctgctg aacatcaccg aacccgaggg gagatggttg tatgatctta  11340
tcaacattct acagagtatc atagtgcagg agcggagcct gggcctggcc gagaaggtgg  11400
ctgccatcaa ttactcggtt ttgagcttgg gaaaatatta cgctcgcaaa atctacaaga  11460
ctccatacgt tcccatagac aaggaggtga agatagatgg gttctacatg cgcatgacgc  11520
tcaaggtctt gaccctgagc gatgatcttg ggtgtatcg caatgacaga atgcatcgcg  11580
cggttagcgc cagcaggagg cgcgagttaa gcgacaggga actgatgcac agtttgcaaa  11640
gagctctgac tggagctgga accgagggtg agaattactt cgacatggga gctgacttgc  11700
agtggcagcc tagtcgcagg gctctgagcg ccgcgacggc aggatgtgag cttccttaca  11760
tagaagaggc ggatgaaggc gaggaggaag agggcgagta cttggaagac tgatggcaca  11820
acccgtgttt tttgctagat ggaacagcaa gcaccggatc ccgcaatgcg ggcggcgctg  11880
cagagccagc cgtccggcat taactcctcg gacgattgga cccaggccat gcaacgtatc  11940
atggcgttga cgactcgcaa ccccgaagcc tttagacagc aaccccaggc caaccgtcta  12000
tcggccatca tggaagctgt agtgccttcc cgctctaatc ccactcatga gaaggtcctg  12060
gccatcgtga acgcgttggt ggagaacaaa gctattcgtc cagatgaggc cggactggta  12120
tacaacgctc tcttagaacg cgtggctcgc tacaacagta gcaatgtgca aaccaatttg  12180
gaccgtatga taacagatgt acgcgaagcc gtgtctcagc gcgaaaggtt ccagcgtgat  12240
gccaacctgg gttcgctggt ggcgttaaat gctttcttga gtactcagcc tgctaatgtg  12300
ccgcgtggtc aacaggatta tactaacttt ttaagtgctt tgagactgat ggtatcagaa  12360
gtacctcaga gcgaagtgta tcagtccggt cctgattact tctttcagac tagcagacag  12420
```

```
ggcttgcaga cggtaaatct gagccaagct tttaaaaacc ttaaaggttt gtggggagtg  12480
catgccccgg taggagaaag agcaaccgtg tctagcttgt taactccgaa ctcccgccta  12540
ttattactgt tggtagctcc tttcaccgac agcggtagca tcgaccgtaa ttcctatttg  12600
ggttacctac taaacctgta tcgcgaagcc atagggcaaa gtcaggtgga cgagcagacc  12660
tatcaagaaa ttacccaagt cagtcgcgct ttgggacagg aagacactgg cagtttggaa  12720
gccactctga acttcttgct taccaatcgg tctcaaaaga tccctcctca atatgctctt  12780
actgcggagg aggagaggat ccttagatat gtgcagcaga gcgtgggatt gtttctgatg  12840
caagaggggg caactccgac tgcagcactg gacatgacag cgcgaaatat ggagcccagc  12900
atgtatgcca gtaaccgacc tttcattaac aaactgctgg actacttgca cagagctgcc  12960
gctatgaact ctgattattt caccaatgcc atcttaaacc cgcactggct gcccccacct  13020
ggtttctaca cgggcgaata tgacatgccc gaccctaatg acggatttct gtgggacgac  13080
gtggacagcg atgtttttc acctctttct gatcatcgca cgtggaaaaa ggaaggcggc  13140
gatagaatgc attcttctgc atcgctgtcc ggggtcatgg gtgctaccgc ggctgagccc  13200
gagtctgcaa gtcctttcc tagtctaccc ttttctctac acagtgtacg tagcagcgaa  13260
gtgggtagaa taagtcgccc gagtttaatg ggcgaagagg agtatctaaa cgattccttg  13320
ctcagaccgg caagagaaaa aaatttccca aacaatggaa tagaaagttt ggtggataaa  13380
atgagtagat ggaagactta tgctcaggat cacagagacg agcctgggat catggggatt  13440
acaagtagag cgagccgtag acgccagcgc catgacagac agaggggtct tgtgtgggac  13500
gatgaggatt cggccgatga tagcagcgtg ctggacttgg gtgggagagg aaggggcaac  13560
ccgtttgctc atttgcgccc tcgcttgggt ggtatgttgt aaaaaaaaat aaaaaaaaaa  13620
ctcaccaagg ccatggcgac gagcgtacgt tcgttcttct ttattatctg tgtctagtat  13680
aatgaggcga gtcgtgctag gcggagcggt ggtgtatccg gagggtcctc ctccttcgta  13740
cgagagcgtg atgcagcagc agcaggcgac ggcggtgatg caatccccac tggaggctcc  13800
ctttgtgcct ccgcgatacc tggcacctac ggagggcaga aacagcattc gttattcgga  13860
actggcacct cagtacgata ccaccaggtt gtatctggtg gacaacaagt cggcggacat  13920
tgcttctctg aactatcaga atgaccacag caacttcttg accacggtgg tgcaaaacaa  13980
tgactttacc cctacggaag ccagcaccca gaccattaac tttgatgaac gatcgcggtg  14040
gggcggtcag ctaaagacca tcatgcatac taacatgcca aacgtgaacg agtatatgtt  14100
tagtaacaag ttcaaagcgc gtgtgatggt gtccagaaaa cctcccgacg gtgctgcagt  14160
tggggatact tatgatcaca agcaggatat tttgaaatat gagtggttcg agtttacttt  14220
gccagaaggc aacttttcag ttactatgac tattgatttg atgaacaatg ccatcataga  14280
taattacttg aaagtgggta gacagaatgg agtgcttgaa agtgacattg gtgttaagtt  14340
cgacaccagg aacttcaagc tgggatggga tcccgaaacc aagttgatca tgcctggagt  14400
gtatacgtat gaagccttcc atcctgacat tgtcttactg cctggctgcg gagtggattt  14460
taccgagagt cgtttgagca accttcttgg tatcagaaaa aaacagccat ttcaagaggg  14520
ttttaagatt ttgtatgaag atttagaagg tggtaatatt ccggccctct tggatgtaga  14580
tgcctatgag aacagtaaga aagaacaaaa agccaaaata gaagctgcta cagctgctgc  14640
agaagctaag gcaaacatag ttgccagcga ctctacaagg gttgctaacg ctggagaggt  14700
cagaggagac aattttgcgc caacacctgt tccgactgca gaatcattat tggccgatgt  14760
gtctgaagga acggacgtga aactcactat tcaacctgta gaaaaagata gtaagaatag  14820
```

```
aagctataat gtgttggaag acaaaatcaa cacagcctat cgcagttggt atctttcgta  14880
caattatggc gatcccgaaa aaggagtgcg ttcctggaca ttgctcacca cctcagatgt  14940
cacctgcgga gcagagcagg tctactggtc gcttccagac atgatgaagg atcctgtcac  15000
tttccgctcc actagacaag tcagtaacta ccctgtggtg ggtgcagagc ttatgcccgt  15060
cttctcaaag agcttctaca acgaacaagc tgtgtactcc cagcagctcc gccagtccac  15120
ctcgcttacg cacgtcttca accgctttcc tgagaaccag attttaatcc gtccgccggc  15180
gcccaccatt accaccgtca gtgaaaacgt tcctgctctc acagatcacg ggaccctgcc  15240
gttgcgcagc agtatccggg gagtccaacg tgtgaccgtt actgacgcca gacgccgcac  15300
ctgtccctac gtgtacaagg cactgggcat agtcgcaccg cgcgtccttt caagccgcac  15360
tttctaaaaa aaaaaaaaat gtccattctt atctcgccca gtaataacac cggttggggt  15420
ctgcgcgctc caagcaagat gtacggaggc gcacgcaaac gttctaccca acatcctgtc  15480
cgtgttcgcg gacattttcg cgctccatgg ggcgccctca agggccgcac tcgcgttcga  15540
accaccgtcg atgatgtaat cgatcaggtg gttgccgacg cccgtaatta tactcctact  15600
gcgcctacat ctactgtgga tgcagttatt gacagtgtag tggctgacgc tcgcaactat  15660
gctcgacgta agagccggcg aaggcgcatt gccagacgcc accgagctac cactgccatg  15720
cgagccgcaa gagctctgct acgaagagct agacgcgtgg ggcgaagagc catgcttagg  15780
gcggccagac gtgcagcttc gggcgccagc gccggcaggt cccgcaggca agcagccgct  15840
gtcgcagcgg cgactattgc cgacatggcc caatcgcgaa gaggcaatgt atactgggtg  15900
cgtgacgctg ccaccggtca acgtgtaccc gtgcgcaccc gtcccccctcg cacttagaag  15960
atactgagca gtctccgatg ttgtgtccca gcggcgagga tgtccaagcg caaatacaag  16020
gaagaaatgc tgcaggttat cgcacctgaa gtctacggcc aaccgttgaa ggatgaaaaa  16080
aaaccccgca aaatcaagcg ggttaaaaag gacaaaaaag aagaggaaga tggcgatgat  16140
gggctggcgg agtttgtgcg cgagtttgcc ccacggcgac gcgtgcaatg gcgtgggcgc  16200
aaagttcgac atgtgttgag acctggaact tcggtggtct ttacacccgg cgagcgttca  16260
agcgctactt ttaagcgttc ctatgatgag gtgtacgggg atgatgatat tcttgagcag  16320
gcggctgacc gattaggcga gtttgcttat ggcaagcgta gtagaataac ttccaaggat  16380
gagacagtgt cgataccctt ggatcatgga aatcccaccc ctagtcttaa accggtcact  16440
ttgcagcaag tgttacccgt aactccgcga acaggtgtta aacgcgaagg tgaagatttg  16500
tatcccacta tgcaactgat ggtacccaaa cgccagaagt tggaggacgt tttggagaaa  16560
gtaaaagtgg atccagatat tcaacctgag gttaaagtga gacccattaa gcaggtagcg  16620
cctggtctgg gggtacaaac tgtagacatt aagattccca ctgaaagtat ggaagtgcaa  16680
actgaacccg caaagcctac tgccacctcc actgaagtgc aaacggatcc atggatgccc  16740
atgcctatta caactgacgc cgccggtccc actcgaagat cccgacgaaa gtacggtcca  16800
gcaagtctgt tgatgcccaa ttatgttgta cacccatcta ttattcctac tcctggttac  16860
cgaggcactc gctactatcg cagccgaaac agtacctccc gccgtcgccg caagacacct  16920
gcaaatcgca gtcgtcgccg tagacgcaca agcaaaccga ctcccggcgc cctggtgcgg  16980
caagtgtacc gcaatggtag tgcggaacct ttgacactgc cgcgtgcgcg ttaccatccg  17040
agtatcatca cttaatcaat gttgccgctg cctccttgca gatatggccc tcacttgtcg  17100
ccttcgcgtt cccatcactg gttaccgagg aagaaactcg cgccgtagaa gagggatgtt  17160
gggacgcgga atgcgacgct acaggcgacg gcgtgctatc cgcaagcaat tgcggggtgg  17220
```

```
tttttacca gccttaattc caattatcgc tgctgcaatt ggcgcgatac caggcatagc  17280
ttccgtggcg gttcaggcct cgcaacgaca ttgacattgg aaaaaaacgt ataaataaaa  17340
aaaaaaaaat acaatggact ctgacactcc tggtcctgtg actatgtttt cttagagatg  17400
gaagacatca atttttcatc cttggctccg cgacacggca cgaagccgta catgggcacc  17460
tggagcgaca tcggcacgag ccaactgaac gggggcgcct tcaattggag cagtatctgg  17520
agcgggctta aaaattttgg ctcaaccata aaaacatacg ggaacaaagc ttggaacagc  17580
agtacaggac aggcgcttag aaataaactt aaagaccaga acttccaaca aaaagtagtc  17640
gatgggatag cttccggcat caatggagtg gtagatttgg ctaaccaggc tgtgcagaaa  17700
aagataaaca gtcgtttgga cccgccgcca gcaaccccag gtgaaatgca agtggaggaa  17760
gaaattcctc cgccagaaaa acgaggcgac aagcgtccgc gtcccgattt ggaagagacg  17820
ctggtgacgc gcgtagatga accgccttct tatgaggaag caacgaagct tggaatgccc  17880
accactagac cgatagcccc aatggccacc ggggtgatga aaccttctca gttgcatcga  17940
cccgtcacct tggatttgcc ccctccccct gctgctactg ctgtacccgc ttctaagcct  18000
gtcgctgccc cgaaaccagt cgccgtagcc aggtcacgtc ccgggggcgc tcctcgtcca  18060
aatgcgcact ggcaaaatac tctgaacagc atcgtgggtc taggcgtgca aagtgtaaaa  18120
cgccgtcgct gcttttaatt aaatatggag tagcgcttaa cttgcctatc tgtgtatatg  18180
tgtcattaca cgccgtcaca gcagcagagg aaaaaaggaa gaggtcgtgc gtcgacgctg  18240
agttactttc aagatggcca ccccatcgat gctgccccaa tgggcataca tgcacatcgc  18300
cggacaggat gcttcggagt acctgagtcc gggtctggtg cagttcgccc gcgccacaga  18360
cacctacttc aatctgggaa ataagtttag aaatcccacc gtagcgccga cccacgatgt  18420
gaccaccgac cgtagccagc ggctcatgtt gcgcttcgtg cccgttgacc gggaggacaa  18480
tacatactct tacaaagtgc ggtacaccct ggccgtgggc gacaacagag tgctggatat  18540
ggccagcacg ttctttgaca ttaggggtgt gttggacaga ggtcccagtt tcaaacccta  18600
ttctggtacg gcttacaact ccctggctcc taaaggcgct ccaaatacat ctcagtggat  18660
tgcagaaggt gtaaaaaata caactggtga ggaacacgta acagaagagg aaaccaatac  18720
tactacttac acttttggca atgctcctgt aaaagctgaa gctgaaatta caaaagaagg  18780
actcccagta ggtttggaag tttcagatga agaaagtaaa ccgatttatg ctgataaaac  18840
atatcagcca gaacctcagc tgggagatga aacttggact gaccttgatg gaaaaaccga  18900
aaagtatgga ggcagggctc tcaaacccga tactaagatg aaaccatgct acgggtcctt  18960
tgccaaacct actaatgtga aaggcggtca ggcaaaacaa aaaacaacgg agcagccaaa  19020
tcagaaagtc gaatatgata tcgacatgga gttttttgat gcggcatcgc agaaaacaaa  19080
cttaagtcct aaaattgtca tgtatgcaga aaatgtaaat ttggaaactc cagacactca  19140
tgtagtgtac aaacctggaa cagaagacac aagttccgaa gctaatttgg gacaacaatc  19200
tatgcccaac agacccaact acattggctt cagagataac tttattggac ttatgtacta  19260
taacagtact ggtaacatgg gggtgctggc tggtcaagcg tctcagttaa atgcagtggt  19320
tgacttgcag gacagaaaca cagaactttc ttaccaactc ttgcttgact ctctgggcga  19380
cagaaccaga tactttagca tgtggaatca ggctgtggac agttatgatc ctgatgtacg  19440
tgttattgaa aatcatggtg tggaagatga acttcccaac tactgttttc cactggacgg  19500
cataggtgtt ccaacaacca gttacaaatc aatagttcca aatggagaca atgcgcctaa  19560
ttggaaggaa cctgaagtaa atggaacaag tgagatcgga cagggtaatt tgtttgccat  19620
```

```
ggaaattaac cttcaagcca atctatggcg aagtttcctt tattccaatg tggctctata  19680
tctcccagac tcgtacaaat acaccccgtc caatgtcact cttccagaaa acaaaaacac  19740
ctacgactac atgaacgggc gggtggtgcc gccatctcta gtagacacct atgtgaacat  19800
tggtgccagg tggtctctgg atgccatgga caatgtcaac ccattcaacc accaccgtaa  19860
cgctggcttg cgttaccgat ccatgcttct gggtaacgga cgttatgtgc ctttccacat  19920
acaagtgcct caaaaattct tcgctgttaa aaacctgctg cttctcccag gctcctacac  19980
ttatgagtgg aactttagga aggatgtgaa catggttcta cagagttccc tcggtaacga  20040
cctgcgggta gatggcgcca gcatcagttt cacgagcatc aacctctatg ctactttttt  20100
ccccatggct cacaacaccg cttccaccct tgaagccatg ctgcggaatg acaccaatga  20160
tcagtcattc aacgactacc tatctgcagc taacatgctc taccccattc ctgccaatgc  20220
aaccaatatt cccatttcca ttccttctcg caactgggcg gctttcagag gctggtcatt  20280
taccagactg aaaaccaaag aaactccctc tttggggtct ggatttgacc cctactttgt  20340
ctattctggt tctattccct acctggatgg taccttctac ctgaaccaca cttttaagaa  20400
ggtttccatc atgtttgact cttcagtgag ctggcctgga aatgacaggt tactatctcc  20460
taacgaattt gaaataaagc gcactgtgga tggcgaaggc tacaacgtag cccaatgcaa  20520
catgaccaaa gactggttct tggtacagat gctcgccaac tacaacatcg gctatcaggg  20580
cttctacatt ccagaaggat acaaagatcg catgtattca tttttcagaa acttccagcc  20640
catgagcagg caggtggttg atgaggtcaa ttacaaagac ttcaaggccg tcgccatacc  20700
ctaccaacac aacaactctg gctttgtggg ttacatggct ccgaccatgc gccaaggtca  20760
accctatccc gctaactatc cctatccact cattggaaca actgccgtaa atagtgttac  20820
gcagaaaaag ttcttgtgtg acagaaccat gtggcgcata ccgttctcga gcaacttcat  20880
gtctatgggg gcccttacag acttgggaca gaatatgctc tatgccaact cagctcatgc  20940
tctggacatg acctttgagg tggatcccat ggatgagccc accctgcttt atcttctctt  21000
cgaagttttc gacgtggtca gagtgcatca gccacaccgc ggcatcatcg aggcagtcta  21060
cctgcgtaca ccgttctcgg ccggtaacgc taccacgtaa gaagcttctt gcttcttgca  21120
aatagcagct gcaaccatgg cctgcggatc ccaaaacggc tccagcgagc aagagctcag  21180
agccattgtc caagacctgg gttgcggacc ctatttttg ggaacctacg ataagcgctt  21240
cccggggttc atggcccccg ataagctcgc ctgtgccatt gtaaatacgg ccggacgtga  21300
gacgggggga gagcactggt tggctttcgg ttggaaccca cgttctaaca cctgctacct  21360
ttttgatcct tttggattct cggatgatcg tctcaaacag atttaccagt ttgaatatga  21420
gggtctcctg cgccgcagcg ctcttgctac caaggaccgc tgtattacgc tggaaaaatc  21480
tacccagacc gtgcagggtc cccgttctgc cgcctgcgga cttttctgct gcatgttcct  21540
tcacgccttt gtgcactggc ctgaccgtcc catggacgga aaccccacca tgaaattgct  21600
aactggagtg ccaaacaaca tgcttcattc tcctaaagtc cagcccaccc tgtgtgacaa  21660
tcaaaaagca ctctaccatt ttcttaatac ccattcgcct tattttcgct cccatcgtac  21720
acacatcgaa agggccactg cgttcgaccg tatggatgtt caataatgac tcatgtaaac  21780
aacgtgttca ataaacatca ctttattttt ttacatgtat caaggctctg cattacttat  21840
ttatttacaa gtcgaatggg ttctgacgag aatcagaatg acccgcaggc agtgatacgt  21900
tgcggaactg atacttgggt tgccacttga attcgggaat caccaacttg ggaaccggta  21960
tatcgggcag gatgtcactc cacagctttc tggtcagctg caaagctcca agcaggtcag  22020
```

```
gagccgaaat cttgaaatca caattaggac cagtgctttg agcgcgagag ttgcggtaca  22080
ccggattgca gcactgaaac accatcagcg acggatgtct cacgcttgcc agcacggtgg  22140
gatctgcaat catgcccaca tccagatctt cagcattggc aatgctgaac ggggtcatct  22200
tgcaggtctg cctacccatg gcgggcaccc aattaggctt gtggttgcaa tcgcagtgca  22260
gggggatcag tatcatcttg gcctgatcct gtctgattcc tggatacacg gctctcatga  22320
aagcatcata ttgcttgaaa gcctgctggg ctttactacc ctcggtataa aacatcccgc  22380
aggacctgct cgaaaactgg ttagctgcac agccggcatc attcacacag cagcgggcgt  22440
cattgttagc tatttgcacc acacttctgc cccagcggtt ttgggtgatt ttggttcgct  22500
cgggattctc ctttaaggct cgttgtccgt tctcgctggc cacatccatc tcgataatct  22560
gctccttctg aatcataata ttgccatgca ggcacttcag cttgccctca taatcattgc  22620
agccatgagg ccacaacgca cagcctgtac attcccaatt atggtgggcg atctgagaaa  22680
aagaatgtat cattccctgc agaaatcttc ccatcatcgt gctcagtgtc ttgtgactag  22740
tgaaagttaa ctggatgcct cggtgctcct cgtttacgta ctggtgacag atgcgcttgt  22800
attgttcgtg ttgctcaggc attagtttaa aagaggttct aagttcgtta tccagcctgt  22860
acttctccat cagcagacac atcacttcca tgcctttctc ccaagcagac accaggggca  22920
agctaatcgg attcttaaca gtgcaggcag cagctccttt agccagaggg tcatctttag  22980
cgatcttctc aatgcttctt ttgccatcct tctcaacgat gcgcacgggc gggtagctga  23040
aacccactgc tacaagttgc gcctcttctc tttcttcttc gctgtcttga ctgatgtctt  23100
gcatggggat atgtttggtc ttccttggct tctttttggg gggtatcgga ggaggaggac  23160
tgtcgctccg ttccggagac agggaggatt gtgacgtttc gctcaccatt accaactgac  23220
tgtcggtaga agaacctgac cccacacggc gacaggtgtt tctcttcggg ggcagaggtg  23280
gaggcgattg cgaagggctg cggtccgacc tggaaggcgg atgactggca gaaccccttc  23340
cgcgttcggg ggtgtgctcc ctgtggcggt cgcttaactg atttccttcg cggctggcca  23400
ttgtgttctc ctaggcagag aaacaacaga catggaaact cagccattgc tgtcaacatc  23460
gccacgagtg ccatcacatc tcgtcctcag cgacgaggaa aaggagcaga gcttaagcat  23520
tccaccgccc agtcctgcca ccacctctac cctagaagat aaggaggtcg acgcatctca  23580
tgacatgcag aataaaaaag cgaaagagtc tgagacagac atcgagcaag acccgggcta  23640
tgtgacaccg gtggaacacg aggaagagtt gaaacgcttt ctagagagag aggatgaaaa  23700
ctgcccaaaa caacgagcag ataactatca ccaagatgct ggaaataggg atcagaacac  23760
cgactacctc atagggcttg acggggaaga cgcgctcctt aaacatctag caagacagtc  23820
gctcatagtc aaggatgcat tattggacag aactgaagtg cccatcagtg tggaagagct  23880
cagccgcgcc tacgagctta acctcttttc acctcgtact ccccccaaac gtcagccaaa  23940
cggcacctgc gagccaaatc ctcgcttaaa cttttatcca gcttttgctg tgccagaagt  24000
actggctacc tatcacatct tttttaaaaa tcaaaaaatt ccagtctcct gccgcgctaa  24060
tcgcacccgc gccgatgccc tactcaatct gggacctggt tcacgcttac ctgatatagc  24120
ttccttggaa gaggttccaa agatcttcga gggtctgggc aataatgaga ctcgggccgc  24180
aaatgctctg caaaagggag aaaatggcat ggatgagcat cacagcgttc tggtggaatt  24240
ggaaggcgat aatgccagac tcgcagtact caagcgaagc atcgaggtca cacacttcgc  24300
atatcccgct gtcaacctgc cccctaaagt catgacggcg gtcatggacc agttactcat  24360
taagcgcgca agtccccttt cagaagacat gcatgaccca gatgcctgtg atgagggtaa  24420
```

```
accagtggtc agtgatgagc agctaacccg atggctgggc accgactctc ccagggattt  24480
ggaagagcgt cgcaagctta tgatggccgt ggtgctggtt accgtagaac tagagtgtct  24540
ccgacgtttc tttaccgatt cagaaacctt gcgcaaactc gaagagaatc tgcactacac  24600
ttttagacac ggctttgtgc ggcaggcatg caagatatct aacgtggaac tcaccaacct  24660
ggtttcctac atgggtattc tgcatgagaa tcgcctagga caaagcgtgc tgcacagcac  24720
cctgaagggg gaagcccgcc gtgattacat ccgcgattgt gtctatctgt acctgtgcca  24780
cacgtggcaa accggcatgg gtgtatggca gcaatgttta gaagaacaga acttgaaaga  24840
gcttgacaag ctcttacaga aatctcttaa ggttctgtgg acagggttcg acgagcgcac  24900
cgtcgcttcc gacctggcag acctcatctt cccagagcgt ctcagggtta ctttgcgaaa  24960
cggattgcct gactttatga gccagagcat gcttaacaat tttcgctctt tcatcctgga  25020
acgctccggt atcctgcccg ccacctgctg cgcactgccc tccgactttg tgcctctcac  25080
ctaccgcgag tgcccccgc cgctatggag tcactgctac ctgttccgtc tggccaacta  25140
tctctcctac cactcggatg tgatcgagga tgtgagcgga gacggcttgc tggagtgtca  25200
ctgccgctgc aatctgtgca cgccccaccg gtccctagct tgcaaccccc agttgatgag  25260
cgaaacccag ataataggca cctttgaatt gcaaggcccc agcagccaag gcgatgggtc  25320
ttctcctggg caaagtttaa aactgacccc gggactgtgg acctccgcct acttgcgcaa  25380
gtttgctccg gaagattacc accccctatga aatcaagttc tatgaggacc aatcacagcc  25440
tccaaaggcc gaactttcgg cctgcgtcat cacccagggg gcaattctgg cccaattgca  25500
agccatccaa aaatcccgcc aagaatttct actgaaaaag ggtaaggggg tctaccttga  25560
cccccagacc ggcgaggaac tcaacacaag gttccctcag gatgtcccaa cgacgagaaa  25620
acaagaagtt gaaggtgcag ccgccgcccc cagaagatat ggaggaagat tgggacagtc  25680
aggcagagga ggcggaggag gacagtctgg aggacagtct ggaggaagac agtttggagg  25740
aggaaaacga ggaggcagag gaggtggaag aagtaaccgc cgacaaacag ttatcctcgg  25800
ctgcggagac aagcaacagc gctaccatct ccgctccgag tcgaggaacc cggcggcgtc  25860
ccagcagtag atgggacgag accggacgct tcccgaaccc aaccagcgct tccaagaccg  25920
gtaagaagga tcggcaggga tacaagtcct ggcgggggca taagaatgcc atcatctcct  25980
gcttgcatga gtgcgggggc aacatatcct tcacgcggcg ctacttgcta ttccaccatg  26040
gggtgaactt tccgcgcaat gttttgcatt actaccgtca cctccacagc ccctactata  26100
gccagcaaat cccggcagtc tcgacagata aagacagcgg cggcgacctc caacagaaaa  26160
ccagcagcgg cagttagaaa atacacaaca agtgcagcaa caggaggatt aaagattaca  26220
gccaacgagc cagcgcaaac ccgagagtta agaaatcgga tctttccaac cctgtatgcc  26280
atcttccagc agagtcgggg tcaagagcag gaactgaaaa taaaaaaccg atctctgcgt  26340
tcgctcacca gaagttgttt gtatcacaag agcgaagatc aacttcagcg cactctcgag  26400
gacgccgagg ctctcttcaa caagtactgc gcgctgactc ttaaagagta ggcagcgacc  26460
gcgcttattc aaaaaaggcg ggaattacat catcctcgac atgagtaaag aaattcccac  26520
gccttacatg tggagttatc aaccccaaat gggattggcg gcaggcgcct cccaggacta  26580
ctccacccgc atgaattggc tcagcgccgg gccttctatg atttctcgag ttaatgatat  26640
acgcgcctac cgaaaccaaa tacttttgga acagtcagct cttaccacca cgccccgcca  26700
acaccttaat cccagaaatt ggcccgccgc cctagtgtac caggaaagtc ccgctcccac  26760
cactgtatta cttcctcgag acgcccaggc cgaagtccaa atgactaatg caggtgcgca  26820
```

```
gttagctggc ggctccaccc tatgtcgtca caggcctcgg cataatataa aacgcctgat  26880
gatcagaggc cgaggtatcc agctcaacga cgagtcggtg agctctccgc ttggtctacg  26940
accagacgga atctttcaga ttgccggctg cgggagatct tccttcaccc ctcgtcaggc  27000
tgttctgact ttggaaagtt cgtcttcgca accccgctcg ggcggaatcg ggaccgttca  27060
atttgtggag gagtttactc cctctgtcta cttcaacccc ttctccggat ctcctgggca  27120
ttacccggac gagttcatac cgaacttcga cgcgattagc gagtcagtgg acggctacga  27180
ttgatgtctg gtgacgcggc tgagctatct cggctgcgac atctagacca ctgccgccgc  27240
tttcgctgct ttgcccggga actcattgag ttcatctact tcgaactccc caaggatcac  27300
cctcaaggtc cggcccacgg agtgcggatt tctatcgaag gcaaaataga ctctcgcctg  27360
caacgaattt tctcccagcg gcccgtgctg atcgagcgag accagggaaa caccacggtt  27420
tccatctact gcatttgtaa tcaccccgga ttgcatgaaa gcctttgctg tcttatgtgt  27480
actgagttta ataaaaactg aattaagact ctcctacgga ctgccgcttc ttcaacccgg  27540
attttacaac cagaagaacg aaacttttcc tgtcgtccag gactctgtta acttcacctt  27600
tcctactcac aaactagaag ctcaacgact acaccgcttt tccagaagca ttttccctac  27660
taatactact ttcaaaaccg gaggtgagct ccaaggtctt cctacagaaa acccttgggt  27720
ggaagcgggc cttgtagtgc taggaattct tgcgggtggg cttgtgatta ttctttgcta  27780
cctatacaca ccttgcttca ctttcttagt ggtgttgtgg tattggttta aaaaatgggg  27840
cccatactag tcttgcttgt tttactttcg cttttggaac cgggttctgc caattacgat  27900
ccatgtctag acttcgaccc agaaaactgc acacttactt ttgcacccga cacaagccgc  27960
atctgtggag ttcttattaa gtgcggatgg gaatgcaggt ccgttgaaat tacacacaat  28020
aacaaaacct ggaacaatac cttatccacc acatgggagc caggagttcc cgagtggtac  28080
actgtctctg tccgaggtcc tgacggttcc atccgcatta gtaacaacac tttcattttt  28140
tctgaaatgt gcgatctggc catgttcatg agcaaacagt attctctatg gcctcctagc  28200
aaggacaaca tcgtaacgtt ctccattgct tattgcttgt gcgcttgcct tcttactgct  28260
ttactgtgcg tatgcataca cctgcttgta accactcgca tcaaaaacgc caataacaaa  28320
gaaaaaatgc cttaacctct ttctgtttac agacatggct tctcttacat ctctcatatt  28380
tgtcagcatt gtcactgccg ctcatggaca aacagtcgtc tctatccctc taggacataa  28440
ttacactctc ataggacccc caatcacttc agaggtcatc tggaccaaac tgggaagcgt  28500
tgattacttt gatataatct gcaacaaaac aaaaccaata atagtaactt gcaacataca  28560
aaatcttaca ttgattaatg ttagcaaagt ttacagcggt tactattatg gttatgacag  28620
atacagtagt caatatagaa attacttggt tcgtgttacc cagttgaaaa ccacgaaaat  28680
gccaaatatg gcaaagattc gatccgatga caattctcta gaaactttta catctcccac  28740
cacacccgac gaaaaaaaca tcccagattc aatgattgca attgttgcag cggtggcagt  28800
ggtgatggca ctaataataa tatgcatgct tttatatgct tgtcgctaca aaaagtttca  28860
tcctaaaaaa caagatctcc tactaaggct taacatttaa tttcttttta tacagccatg  28920
gtttccacta ccacattcct tatgcttact agtctcgcaa ctctgacttc tgctcgctca  28980
cacctcactg taactatagg ctcaaactgc acactaaaag gacctcaagg tggtcatgtc  29040
ttttggtgga gaatatatga caatggatgg tttacaaaac catgtgacca acctggtaga  29100
tttttctgca acggcagaga cctaaccatt atcaacgtga cagcaaatga caaaggcttc  29160
tattatggaa ccgactataa aagtagttta gattataaca ttattgtact gccatctacc  29220
```

```
actccagcac cccgcacaac tactttctct agcagcagtg tcgctaacaa tacaatttcc  29280
aatccaacct ttgccgcgct tttaaaacgc actgtgaata attctacaac ttcacataca  29340
acaatttcca cttcaacaat cagcattatc gctgcagtga caattggaat atctattctt  29400
gtttttacca taacctacta cgcctgctgc tatagaaaag acaaacataa aggtgatcca  29460
ttacttagat ttgatattta atttgttctt ttttttttta tttacagtat ggtgaacacc  29520
aatcatggta cctagaaatt tcttcttcac catactcatt tgtgcattta atgtttgcgc  29580
tactttcaca gcagtagcca cagcaacccc agactgtata ggagcatttg cttcctatgc  29640
actttttgct tttgttactt gcatctgcgt atgtagcata gtctgcctgg ttattaattt  29700
tttccaactt atagactgga tccttgtgcg aattgcctac ctgcgccacc atcccgaata  29760
ccgcaaccaa aatatcgcgg cacttcttag actcatctaa aaccatgcag gctatactac  29820
caatattttt gcttctattg cttccctacg ctgtctcaac cccagctgcc tatagtactc  29880
caccagaaca ccttagaaaa tgcaaattcc aacaaccgtg gtcatttctt gcttgctatc  29940
gagaaaaatc agaaattccc ccaaatttaa taatgattgc tggaataatt aatataatct  30000
gttgcaccat aatttcattt ttgatatacc ccctatttga ttttggctgg aatgctccca  30060
atgcacatga tcatccacaa gacccagagg aacacattcc cctacaaaac atgcaacatc  30120
caatagcgct aatagattac gaaagtgaac cacaaccccc actactccct gctattagtt  30180
acttcaacct aaccggcgga gatgactgaa acactcacca cctccaattc cgccgaggat  30240
ctgctcgata tggacggccg cgtctcagaa cagcgactcg cccaactacg catccgccag  30300
cagcaggaac gcgcggccaa agagctcaga gatgtcatcc aaattcacca atgcaaaaaa  30360
ggcatattct gtttggtaaa acaagccaag atatcctacg agatcaccgc tactgaccat  30420
cgcctctctt acgaacttgg cccccaacga caaaaattta cctgcatggt gggaatcaac  30480
cccatagtta tcacccagca aagtggagat actaagggtt gcattcactg ctcctgcgat  30540
tccatcgagt gcacctacac cctgctgaag accctatgcg gcctaagaga cctgctacca  30600
atgaattaaa aaatgattaa taaaaaatca cttacttgaa atcagcaata aggtctctgt  30660
tgaaattttc tcccagcagc acctcacttc cctcttccca actctggtat tctaaacccc  30720
gttcagcggc atactttctc catactttaa aggggatgtc aaattttagc tcctctcctg  30780
tacccacaat cttcatgtct ttcttcccag atgaccaaga gagtccggct cagtgactcc  30840
ttcaaccctg tctacccta tgaagatgaa agcacctccc aacacccctt tataaaccca  30900
gggtttattt ccccaaatgg cttcacacaa agcccaaacg gagttcttac tttaaaatgt  30960
ttaaccccac taacaaccac aggcggatct ctacagctaa aagtgggagg gggacttaca  31020
gtggatgaca ccaacggttt tttgaaagaa aacataagtg ccaccacacc actcgttaag  31080
actggtcact ctataggttt accactagga gccggattgg gaacgaatga aaataaactt  31140
tgtatcaaat taggacaagg acttacattc aattcaaaca acatttgcat tgatgacaat  31200
attaacacct tatggacagg agtcaacccc accgaagcca actgtcaaat catgaactcc  31260
agtgaatcta atgattgcaa attaattcta acactagtta aaactggagc actagtcact  31320
gcatttgttt atgttatagg agtatctaac aattttaata tgctaactac acacagaaat  31380
ataaatttta ctgcagagct gtttttcgat tctactggta atttactaac tagactctca  31440
tccctcaaaa ctccacttaa tcataaatca ggacaaaaca tggctactgg tgccattact  31500
aatgctaaag gtttcatgcc cagcacgact gcctatcctt tcaatgataa ttctagagaa  31560
aaagaaaact acatttacgg aacttgttac tacacagcta gtgatcgcac tgcttttccc  31620
```

```
attgacatat ctgtcatgct taaccgaaga gcaataaatg acgagacatc atattgtatt  31680
cgtataactt ggtcctggaa cacaggagat gccccagagg tgcaaacctc tgctacaacc  31740
ctagtcacct ccccatttac cttttactac atcagagaag acgactgaca aataaagttt  31800
aacttgttta tttgaaaatc aattcacaaa atccgagtag ttattttgcc tcccccttcc  31860
catttaacag aatacaccaa tctctcccca cgcacagctt taaacatttg gataccatta  31920
gatatagaca tggttttaga ttccacattc caaacagttt cagagcgagc caatctgggg  31980
tcagtgatag ataaaaatcc atcgggatag tcttttaaag cgctttcaca gtccaactgc  32040
tgcggatgcg actccggagt ctggatcacg gtcatctgga agaagaacga tgggaatcat  32100
aatccgaaaa cggtatcgga cgattgtgtc tcatcaaacc cacaagcagc cgctgtctgc  32160
gtcgctccgt gcgactgctg tttatgggat cagggtccac agtgtcctga agcatgattt  32220
taatagccct taacatcaac tttctggtgc gatgcgcgca gcaacgcatt ctgatttcac  32280
tcaaatcttt gcagtaggta caacacatta ttacaatatt gtttaataaa ccataattaa  32340
aagcgctcca gccaaaactc atatctgata taatcgcccc tgcatgacca tcataccaaa  32400
gtttaatata aattaaatga cgttccctca aaaacacact acccacatac atgatctctt  32460
ttggcatgtg catattaaca atctgtctgt accatggaca acgttggtta atcatgcaac  32520
ccaatataac cttccggaac cacactgcca acaccgctcc cccagccatg cattgaagtg  32580
aaccctgctg attacaatga caatgaagaa cccaattctc tcgaccgtga atcacttgag  32640
aatgaaaaat atctatagtg gcacaacata gacataaatg catgcatctt ctcataattt  32700
ttaactcctc aggatttaga aacatatccc agggaatagg aagctcttgc agaacagtaa  32760
agctggcaga acaaggaaga ccacgaacac aacttacact atgcatagtc atagtatcac  32820
aatctggcaa cagcgggtgg tcttcagtca tagaagctcg ggtttcattt tcctcacaac  32880
gtggtaactg ggctctggtg taagggtgat gtctggcgca tgatgtcgag cgtgcgcgca  32940
accttgtcat aatggagttg cttcctgaca ttctcgtatt ttgtatagca aaacgcggcc  33000
ctggcagaac acactcttct tcgccttcta tcctgccgct tagcgtgttc cgtgtgatag  33060
ttcaagtaca accacactct taagttggtc aaaagaatgc tggcttcagt tgtaatcaaa  33120
actccatcgc atctaatcgt tctgaggaaa tcatccacgg tagcatatgc aaatcccaac  33180
caagcaatgc aactggattg tgtttcaagc aggagaggag agggaagaga cggaagaacc  33240
atgttaattt ttattccaaa cgatctcgca gtacttcaaa ttgtagatcg cgcagatggc  33300
atctctcgcc cccactgtgt tggtgaaaaa gcacagctag atcaaaagaa atgcgatttt  33360
caaggtgctc aacggtggct tccagcaaag cctccacgcg cacatccaag aacaaaagaa  33420
taccaaaaga aggagcattt tctaactcct caatcatcat attacattcc tgcaccattc  33480
ccagataatt ttcagctttc cagccttgaa ttattcgtgt cagttcttgt ggtaaatcca  33540
atccacacat tacaaacagg tcccggaggg cgccctccac caccattctt aaacacaccc  33600
tcataatgac aaaatatctt gctcctgtgt cacctgtagc gaattgagaa tggcaacatc  33660
aattgacatg cccttggctc taagttcttc tttaagttct agttgtaaaa actctctcat  33720
attatcacca aactgcttag ccagaagccc cccgggaaca agagcagggg acgctacagt  33780
gcagtacaag cgcagacctc cccaattggc tccagcaaaa acaagattgg aataagcata  33840
ttgggaaccg ccagtaatat catcgaagtt gctggaaata taatcaggca gagtttcttg  33900
taaaaattga ataaaagaaa aatttgccaa aaaaacattc aaaacctctg ggatgcaaat  33960
gcaataggtt accgcgctgc gctccaacat tgttagtttt gaattagtct gcaaaaataa  34020
```

```
aaaaaaaaac aagcgtcata tcatagtagc ctgacgaaca gatggataaa tcagtctttc  34080

catcacaaga caagccacag ggtctccagc tcgaccctcg taaaacctgt catcatgatt  34140

aaacaacagc accgaaagtt cctcgcggtg accagcatga ataattcttg atgaagcata  34200

caatccagac atgttagcat cagttaacga gaaaaaacag ccaacatagc ctttgggtat  34260

aattatgctt aatcgtaagt atagcaaagc cacccctcgc ggatacaaag taaaaggcac  34320

aggagaataa aaaatataat tatttctctg ctgctgttca ggcaacgtcg cccccggtcc  34380

ctctaaatac acatacaaag cctcatcagc catggcttac cagacaaagt acagcgggca  34440

cacaaagcac aagctctaaa gtgactctcc aacctctcca caatatatat atacacaagc  34500

cctaaactga cgtaatggga gtaaagtgta aaaaatcccg ccaaacccaa cacacacccc  34560

gaaactgcgt caccagggaa aagtacagtt tcacttccgc aatcccaaca ggcgtaactt  34620

cctctttctc acggtacgtg atatcccact aacttgcaac gtcattttcc cacggtcgca  34680

ccgccccttt tagccgttaa ccccacagcc aatcaccaca cgatccacac tttttaaaat  34740

cacctcattt acatattggc accattccat ctataaggta tattatatag atag        34794
```

<210> SEQ ID NO 3
<211> LENGTH: 5287
<212> TYPE: DNA
<213> ORGANISM: Adenovirus

<400> SEQUENCE: 3

```
ctatggcatc tcgatccagc agacctcctc gtttcgcggg tttggacggc tcctggaata     60

gggtatgaga cgatgggcgt ccagcgctgc cagggttcgg tccttccagg gtctcagtgt    120

tcgagtcagg gttgtttccg tcacagtgaa ggggtgtgcg cctgcttggg cgcttgccag    180

ggtgcgcttc agactcatcc tgctggtcga aaacttctgt cgcttggcgc cctgtatgtc    240

ggccaagtag cagtttacca tgagttcgta gttgagcgcc tcggctgcgt ggcctttggc    300

gcggagctta cctttggaag ttttcttgca taccgggcag tataggcatt tcagcgcata    360

caacttgggc gcaaggaaaa cggattctgg ggagtatgca tctgcgccgc aggaggcgca    420

aacagtttca cattccacca gccaggttaa atccggttca ttggggtcaa aaacaagttt    480

tccgccatat tttttgatgc gtttcttacc tttggtctcc atgagttcgt gtcctcgttg    540

agtgacaaac aggctgtccg tgtccccgta gactgatttt acaggcctct tctccagtgg    600

agtgcctcgg tcttcttcgt acaggaactc tgaccactct gatacaaagg cgcgcgtcca    660

ggccagcaca aaggaggcta tgtgggaggg gtagcgatcg ttgtcaacca gggggtccac    720

cttttccaaa gtatgcaaac acatgtcacc ctcttcaaca tccaggaatg tgattggctt    780

gtaggtgtat ttcacgtgac ctggggtccc cgctgggggg gtataaaagg gggcggttct    840

ttgctcttcc tcactgtctt ccggatcgct gtccaggaac gtcagctgtt ggggtaggta    900

ttccctctcg aaggcgggca tgacctctgc actcaggttg tcagtttcta agaacgagga    960

ggatttgata ttgacagtgc cggttgagat gcctttcatg aggttttcgt ccatctggtc   1020

agaaaacaca attttttat tgtcaagttt ggtggcaaat gatccataca gggcgttgga   1080

taaaagtttg gcaatggatc gcatggtttg gttcttttcc ttgtccgcgc gctctttggc   1140

ggcgatgttg agttggacat actcgcgtgc caggcacttc cattcgggga agatagttgt   1200

taattcatct ggcacgattc tcacttgcca ccctcgatta tgcaaggtaa ttaaatccac   1260

actggtggcc acctcgcctc gaaggggttc attggtccaa cagagcctac ctcctttcct   1320

agaacagaaa gggggaagtg ggtctagcat aagttcatcg ggagggtctg catccatggt   1380
```

```
aaagattccc ggaagtaaat ccttatcaaa atagctgatg ggagtggggt catctaaggc   1440
catttgccat tctcgagctg ccagtgcgcg ctcatatggg ttaaggggac tgccccatgg   1500
catgggatgg gtgagtgcag aggcatacat gccacagatg tcatagacgt agatgggatc   1560
ctcaaagatg cctatgtagg ttggatagca tcgccccct ctgatacttg ctcgcacata   1620
gtcatatagt tcatgtgatg gcgctagcag ccccggaccc aagttggtgc gattgggttt   1680
ttctgttctg tagacgatct ggcgaaagat ggcgtgagaa ttggaagaga tggtgggtct   1740
ttgaaaaatg ttgaaatggg catgaggtag acctacagag tctctgacaa agtgggcata   1800
agattcttga agcttggtta ccagttcggc ggtgacaagt acgtctaggg cgcagtagtc   1860
aagtgtttct tgaatgatgt cataacctgg ttggtttttc ttttcccaca gttcgcggtt   1920
gagaaggtat tcttcgcgat ccttccagta ctcttctagc ggaaacccgt ctttgtctgc   1980
acggtaagat cctagcatgt agaactgatt aactgccttg taagggcagc agcccttctc   2040
tacgggtaga gagtatgctt gagcagcttt tcgtagcgaa gcgtgagtaa gggcaaaggt   2100
gtctctgacc atgactttga ggaattggta tttgaagtcg atgtcgtcac aggctccctg   2160
ttcccagagt tggaagtcta cccgtttctt gtaggcgggg ttgggcaaag cgaaagtaac   2220
atcattgaag agaatcttgc cggccctggg catgaaattg cgagtgatgc gaaaaggctg   2280
tggtacttcc gctcggttat tgataacctg ggcagctagg acgatctcgt cgaaaccgtt   2340
gatgttgtgt cctacgatgt ataattctat gaaacgcggc gtgcctctga cgtgaggtag   2400
cttactgagc tcatcaaagg ttaggtctgt ggggtcagat aaggcgtagt gttcgagagc   2460
ccattcgtgc aggtgaggat tcgctttaag gaaggaggac cagaggtcca ctgccagtgc   2520
tgtttgtaac tggtcccggt actgacgaaa atgccgtccg actgccattt ttctggggt   2580
gacgcaatag aaggtttggg ggtcctgccg ccagcgatcc cacttgagtt ttatggcgag   2640
gtcataggcg atgttgacga gccgctggtc tccagagagt ttcatgacca gcatgaaggg   2700
gattagctgc ttgccaaagg accccatcca ggtgtaggtt tccacatcgt aggtgagaaa   2760
gagcctttct gtgcgaggat gagagccaat cgggaagaac tggatctcct gccaccagtt   2820
ggaggaatgg ctgttgatgt gatggaagta gaactccctg cgacgcgccg agcattcatg   2880
cttgtgcttg tacagacggc cgcagtagtc gcagcgttgc acgggttgta tctcgtgaat   2940
gagttgtacc tggcttccct tgacgagaaa tttcagtggg aagccgaggc ctggcgattg   3000
tatctcgtgc tttactatgt tgtctgcatc ggcctgttca tcttctgtct cgatggtggt   3060
catgctgacg agccctcgcg ggaggcaagt ccagacctcg gcgcggcagg ggcggagctc   3120
gaggacgaga gcgcgcaggc tggagctgtc cagggtcctg agacgctgcg gactcaggtt   3180
agtaggcagt gtcaggagat taacttgcat gatcttttgg agggcgtgcg ggaggttcag   3240
atagtacttg atctcaacgg gtccgttggt ggagatgtcg atggcttgca gggttccgtg   3300
tcccttgggc gctaccaccg tgcccttgtt tttcattttg gacggcggtg gctctgttgc   3360
ttcttgcatg tttagaagcg gtgtcgaggg cgcgcaccgg gcggcagggg cggctcggga   3420
cccggcggca tggctggcag tggtacgtcg gcgccgcgcg cgggtaggtt ctggtactgc   3480
gccctgagaa gactcgcatg cgcgacgacg cggcggttga catcctggat ctgacgcctc   3540
tgggtgaaag ctaccggccc cgtgagcttg aacctgaaag agagttcaac agaatcaatc   3600
tcggtatcgt tgacggcggc ttgcctaagg atttcttgca cgtcaccaga gttgtcctgg   3660
taggcgatct ccgccatgaa ctgctcgatc tcttcctctt gaagatctcc gcggcccgct   3720
ctctcgacgg tggccgcgag gtcgttggag atgcgcccaa tgagttgaga gaatgcattc   3780
```

atgcccgcct cgttccagac gcggctgtag accacggccc ccacgggatc tctcgcgcgc 3840
atgaccacct gggcgaggtt gagctccacg tggcgggtga agaccgcata gttgcatagg 3900
cgctggaaaa ggtagttgag tgtggtggcg atgtgctcgg tgacgaagaa atacatgatc 3960
catcgtctca gcggcatctc gctgacatcg cccagagctt ccaagcgctc catggcctcg 4020
tagaagtcca cggcaaaatt aaaaaactgg gagtttcgcg cggacacggt caactcctct 4080
tccagaagac ggataagttc ggcgatggtg gtgcgcacct cgcgctcgaa agcccctggg 4140
atttcttcct caatctcttc ttcttccact aacatctctt cctcttcagg tggggctgca 4200
ggaggagggg gaacgcggcg acgccggcgg cgcacgggca gacggtcgat gaatctttca 4260
atgacctctc cgcggcggcg gcgcatggtt tcagtgacgg cgcggccgtt ctcgcgcggt 4320
cgcagagtaa aaacaccgcc gcgcatctcc ttaaagtggt gactgggagg ttctccgttt 4380
gggagggaga gggcgctgat tatacatttt attaattggc ccgtagggac tgcacgcaga 4440
gatctgatcg tgtcaagatc cacgggatct gaaaaccttt cgacgaaagc gtctaaccag 4500
tcacagtcac aaggtaggct gagtacggct tcttgtgggc gggggtggtt atgtgttcgg 4560
tctgggtctt ctgtttcttc ttcatctcgg gaaggtgaga cgatgctgct ggtgatgaaa 4620
ttaaagtagg cagttctaag acggcggatg gtggcgagga gcaccaggtc tttgggtccg 4680
gcttgctgga tacgcaggcg attggccatt ccccaagcat tatcctgaca tctagcaaga 4740
tctttgtagt agtcttgcat gagccgttct acgggcactt cttcctcacc cgttctgcca 4800
tgcatacgtg tgagtccaaa tccgcgcatt ggttgtacca gtgccaagtc agctacgact 4860
ctttcggcga ggatggcttg ctgtacttgg gtaagggtgg cttgaaagtc atcaaaatcc 4920
acaaagcggt ggtaagctcc tgtattaatg gtgtaagcac agttggccat gactgaccag 4980
ttaactgtct ggtgaccagg gcgcacgagc tcggtgtatt taaggcgcga ataggcgcgg 5040
gtgtcaaaga tgtaatcgtt gcaggtgcgc accagatact ggtaccctat aagaaaatgc 5100
ggcggtggtt ggcggtagag aggccatcgt tctgtagctg gagcgccagg ggcgaggtct 5160
tccaacataa ggcggtgata gccgtagatg tacctggaca tccaggtgat tcctgcggcg 5220
gtagtagaag cccgaggaaa ctcgcgtacg cggttccaaa tgttgcgtag cggcatgaag 5280
tagttca 5287

<210> SEQ ID NO 4
<211> LENGTH: 21
<212> TYPE: DNA
<213> ORGANISM: artificial sequence
<220> FEATURE:
<223> OTHER INFORMATION: primer

<400> SEQUENCE: 4
gggagtttcg cgcggacacg g 21

<210> SEQ ID NO 5
<211> LENGTH: 21
<212> TYPE: DNA
<213> ORGANISM: artificial sequence
<220> FEATURE:
<223> OTHER INFORMATION: primer

<400> SEQUENCE: 5
gcgccgccgc cgcggagagg t 21

<210> SEQ ID NO 6
<211> LENGTH: 24

<212> TYPE: DNA
<213> ORGANISM: artificial sequence
<220> FEATURE:
<223> OTHER INFORMATION: primer

<400> SEQUENCE: 6
cgagagccca ttcgtgcagg tgag 24

<210> SEQ ID NO 7
<211> LENGTH: 24
<212> TYPE: DNA
<213> ORGANISM: artificial sequence
<220> FEATURE:
<223> OTHER INFORMATION: primer

<400> SEQUENCE: 7
gctgcgacta ctgcggccgt ctgt 24

<210> SEQ ID NO 8
<211> LENGTH: 4195
<212> TYPE: DNA
<213> ORGANISM: Adenovirus

<400> SEQUENCE: 8
tcataagact ctcgtccatc tggtcagaaa acacaatctt cttgttgtcc agcttggtgg 60
caaatgatcc atagagggca ttggatagaa gcttggcgat ggagcgcatg gtttggttct 120
tttccttgtc cgcgcgctcc ttggcggtga tgttaagctg gacgtactcg cgcgccacac 180
atttccattc aggaaagatg gttgtcagtt catccggaac tattctgatt cgccatcccc 240
tattgtgcag ggttatcaga tccacactgg tggccacctc gcctcggagg ggctcattgg 300
tccagcagag tcgacctcct ttcttgaac agaaaggggg gagggggtct agcatgaact 360
catcaggggg gtccgcatct atggtaaata ttcccggtag caaatctttg tcaaaatagc 420
tgatggtggc gggatcatcc aaggtcatct gccattctcg aactgccagc gcgcgctcat 480
aggggttaag aggggtgccc cagggcatgg ggtgggtgag cgcggaggca tacatgccac 540
agatatcgta gacatagagg ggctcttcga ggatgccgat gtaagtggga taacatcgcc 600
cccctctgat gcttgctcgc acatagtcat agagttcatg tgagggggca agaagacccg 660
ggcccagatt ggtgcggttg ggtttttccg ccctgtaaac gatctggcga aagatggcat 720
gggaattgga agagatagta ggtctctgga atatgttaaa atgggcatga ggtaagccta 780
cagagtccct tatgaagtgg gcatatgact cttgcagctt ggctaccagc tcggcggtga 840
tgagtacatc cagggcacag tagtcgagag tttcctggat gatgtcataa cgcggttggc 900
ttttcttttc ccacagctcg cggttgagaa ggtattcttc gtgatccttc cagtactctt 960
cgaggggaaa cccgtctttt tctgcacggt aagagcccaa catgtagaac tgattgactg 1020
ccttgtaggg acagcatccc ttctccactg ggagagagta tgcttgggct gcattgcgca 1080
gcgaggtatg agtgagggca aaagtgtccc tgaccatgac tttgaggaat tgatacttga 1140
agtcgatgtc atcacaggcc ccctgttccc agagttggaa gtccacccgc ttcttgtagg 1200
cggggttggg caaagcgaaa gtaacatcat tgaagaggat cttgccggcc ctgggcatga 1260
aatttcgggt gattttgaaa ggctgaggaa cctctgctcg gttattgata acctgagcgg 1320
ccaagacgat ctcatcaaag ccattgatgt tgtgccccac tatgtacagt tctaagaatc 1380
gaggggtgcc cctgacatga ggcagcttct tgagttcttc aaaagtgaga tctgtagggt 1440
cagtgagagc atagtgttcg agggcccatt cgtgcacgtg agggttcgct ttaaggaagg 1500
aggaccagag gtccactgcc agtgctgttt gtaactggtc ccggtactga cgaaaatgct 1560

```
gtccgactgc catcttttct ggggtgacgc aatagaaggt ttgggggtcc tgccgccagc   1620
gatcccactt gagttttatg gcgaggtcat aggcgatgtt gacgagccgc tggtctccag   1680
agagtttcat gaccagcatg aaggggatta gctgcttgcc aaaggacccc atccaggtgt   1740
aggtttccac atcgtaggtg agaaagagcc tttctgtgcg aggatgagag ccaatcggga   1800
agaactggat ctcctgccac cagttggagg aatggctgtt gatgtgatgg aagtagaact   1860
ccctgcgacg cgccgagcat tcatgcttgt gcttgtacag acggccgcag tactcgcagc   1920
gattcacggg atgcacctta tgaatgagtt gtacctgact tcctttgacg agaaatttca   1980
gtggaaaatt gaggcctggc gcttgtacct cgcgctttac tatgttgtct gcatcggcat   2040
gaccatcttc tgtctcgatg gtggtcatgc tgacgagccc tcgcgggagg caagtccaga   2100
cctcggcgcg gcaggggcgg agctcgagga cgagagcgcg caggccggag ctgtccaggg   2160
tcctgagacg ctgcggagtc aggttagtag gcagtgtcag gagattaact tgcatgatct   2220
tttggagggc gtgagggagg ttcagatagt acttgatctc aacgggtccg ttggtggaga   2280
tgtcgatggc ttgcagggtt ccgtgtccct tgggcgctac caccgtgccc ttgtttttca   2340
ttttggacgg cggtggctct gttgcttctt gcatgtttag aagcggtgtc gagggcgcgc   2400
accgggcggc aggggcggct cgggacccgg cggcatggct ggcagtggta cgtcggcgcc   2460
gcgcgcgggt aggttctggt actgcgccct gagaagactc gcatgcgcga cgacgcggcg   2520
gttgacatcc tggatctgac gcctctgggt gaaagctacc ggccccgtga gcttgaacct   2580
gaaagagagt tcaacagaat caatctcggt atcgttgacg gcggcttgcc taaggatttc   2640
ttgcacgtcg ccagagttgt cctggtaggc gatctcggcc atgaactgct cgatctcttc   2700
ctcttgaaga tctccgcggc ccgctctctc gacggtggcc gcgaggtcgt tggagatgcg   2760
cccaatgagt tgagagaatg cattcatgcc cgcctcgttc cagacgcggc tgtagaccac   2820
agcccccacg ggatctctcg cgcgcatgac cacctgggcg aggttgagct ccacgtggcg   2880
ggtgaagacc gcatagttgc ataggcgctg gaaaaggtag ttgagtgtgg tggcgatgtg   2940
ctcggtgacg aagaaataca tgatccatcg tctcagcggc atctcgctga catcgcccag   3000
cgcttccaag cgctccatgg cctcgtagaa gtccacggca aagttaaaaa actgggagtt   3060
acgcgcggac acggtcaact cctcttccag aagacggata agttcggcga tggtggtgcg   3120
cacctcgcgc tcgaaagccc ctgggatttc ttcctcaatc tcttcttctt ccactaacat   3180
ctcttcctct tcaggtgggg ctgcaggagg agggggaacg cggcgacgcc ggcggcgcac   3240
gggcagacgg tcgatgaatc tttcaatgac ctctccgcgg cggcggcgca tggtctcggt   3300
gacggcacga ccgttctccc tgggtctcag agtgaagacg cctccgcgca tctccctgaa   3360
gtggtgactg ggaggctctc cgttgggcag ggacaccgcg ctgattatgc attttatcaa   3420
ttgccccgta ggtactccgc gcaaggacct gatcgtctca agatccacgg gatctgaaaa   3480
cctttcgacg aaagcgtcta accagtcgca atcgcaaggt aggctgagca ctgtttcttg   3540
cgggcggggg cggctagacg ctcggtcggg gttctctctt tcttctcctt cctcctcttg   3600
ggagggtgag acgatgctgc tggtgatgaa attaaaatag gcagttttga gacggcggat   3660
ggtggcgagg agcaccaggt ctttgggtcc ggcttgttgg atacgcaggc gatgagccat   3720
tccccaagca ttatcctgac atctggccag atctttatag tagtcttgca tgagtcgttc   3780
cacgggcact tcttcttcgc ccgctctgcc atgcatgcga gtgatcccga acccgcgcat   3840
gggctggaca agtgccaggt ccgctacaac cctttcggcg aggatggctt gctgcacctg   3900
ggtgagggtg gcttggaagt cgtcaaagtc cacgaagcgg tggtaggccc cggtgttgat   3960
```

-continued

```
tgtgtaggag cagttggcca tgactgacca gttgactgtc tggtgcccag ggcgcacgag   4020

ctcggtgtac ttgaggcgcg agtatgcgcg ggtgtcaaag atgtaatcgt tgcaggtgcg   4080

caccaggtac tggtagccaa tgagaaagtg tggcggtggc tggcggtaca ggggccatcg   4140

ctctgtagcc ggggctccgg gggcgaggtc ttccagcatg aggcggtggt agccg        4195
```